US009023821B2

(12) United States Patent
Marcet et al.

(10) Patent No.: US 9,023,821 B2
(45) Date of Patent: May 5, 2015

(54) USE OF MICRORNA FOR TREATING DISEASES ASSOCIATED WITH A DYSFUNCTION OF THE CILIA IN MULTICILIATED EPITHELIAL CELLS

(75) Inventors: Brice Marcet, Le Cannet (FR); Pascal Barbry, Nice (FR); Rainer Waldmann, Les Adrets de L'Esterel (FR); Bernard Mari, Nice (FR); Christelle Coraux, Reims (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 13/387,314

(22) PCT Filed: Jul. 26, 2010

(86) PCT No.: PCT/FR2010/000539
§ 371 (c)(1),
(2), (4) Date: Mar. 26, 2012

(87) PCT Pub. No.: WO2011/015720
PCT Pub. Date: Feb. 10, 2011

(65) Prior Publication Data
US 2012/0184599 A1    Jul. 19, 2012

(30) Foreign Application Priority Data

Jul. 29, 2009   (FR) ..................................... 09 03723

(51) Int. Cl.
| | |
|---|---|
| *A61K 48/00* | (2006.01) |
| *C07H 21/04* | (2006.01) |
| *C07H 21/02* | (2006.01) |
| *C12N 15/113* | (2010.01) |
| *C12Q 1/68* | (2006.01) |

(52) U.S. Cl.
CPC ........ *C12N 15/113* (2013.01); *C12N 2310/141* (2013.01); *C12N 2320/10* (2013.01); *C12N 2330/10* (2013.01); *C12Q 1/6886* (2013.01); *C12Q 2600/178* (2013.01)

(58) Field of Classification Search
CPC ........... C12Q 1/6886; C12Q 2600/158; C12Q 2600/178; C12N 15/113
See application file for complete search history.

(56) References Cited

FOREIGN PATENT DOCUMENTS

| WO | WO 2007/021896 | 2/2007 |
| WO | WO 2008/073922 A2 | 6/2008 |
| WO | WO 2008/116267 A1 | 10/2008 |
| WO | WO 2008/137862 A2 | 11/2008 |
| WO | WO 2009/137912 A1 | 11/2009 |
| WO | WO 2009/143379 A2 | 11/2009 |

OTHER PUBLICATIONS

Qian, Shen, et al.; "MicroRNA expression profile of bronchioalveolar stem cells from mouse lung"; Biochemical and Biophysical Research Communications 377 (2008) 668-673.
Perry, Mark M., et al.; "Rapid Changes in MicroRNA-146a Expression Negatively Regulate the IL-12-Induced Inflammatory Response in Human Lung Alveolar Epithelial Cells"; J. Immunol. 2008; 180;5689-5698.
Nana-Sinkam, Serge P., et al.; "Integrating the MicroRNome into the Study of Lung Disease"; American Journal of Respiratory and Critical Care Medicine, vol. 179 (2009), pp. 4-10.
Lu, Yun, et al.; "Epithelial Progenitor Cells of the Embryonic Lung and the Role of MircoRNAs in Their Proliferation"; Proceedings of the American Thoracic Soceity, vol. 5 (2008), pp. 300-304.
Puchelle et al.; Proc. Am. Thorac. Soc. (2006) 3, 726-733.
Hajj, R. et al.; J. Pathol. (2007) 211, 340-350.
Yu, X. et al.; Nat. Genet. (2008) 40, 1445-1453.
Gomperts, B.N., et al.; J. Cell. Sci. (2004) 117, 1329-1337.
Marshall, W.F.; J. Cell. Biol. (2008), 180, 17-21.
Lu, Y. et al. (2007) Dev. Biol. 310, 442-453.
Berezikov, E., et al., Cell (2005) 120, 21-24.
Xie, X. et al.; (2005) Nature 434, 338-345.
Lena, A.M., et al.; (2008) Cell Death. Differ. 15, 1187-1195.
Yi, R. et al.; (2008) Nature 452, 225-229.
Lu, Y. et al. (2007) Dev. Biol. 310, 442-453.
Harris, K.S. et al. (2006) Proc Natl Acad Sci USA 103, 2208-2213.
Lu, Y. et al. (2008) Proc. Am. Thorac. Soc. 5, 300-304.
Triboulet, R. et al.; (2007) Science 315, 1579-1582.
Calin, G.A. & Croce, C.M.; (2006) Nat. Rev. Cancer 6, 857-866.
Grassmann, R. & Jeang, K.T. (2008) Biochim. Biophys. Acta 1779, 706-711.
Latronico, M.V. (2008) Physiol. Genomics 34, 239-242.
Poy, M.N. et al.; (2004) Nature 432, 226-230.
Rana, T.M.; Nature Reviews, 2007, vol. 8: 23-26.
O Van Schayck, et al.; IPAG Diagnosis & Management Handbook; Chronic Airways Disease; A Guide for Primary Care Physicians; pp. 1-34; 2005.
Wu et al.; 1985.
Marcet et al.; 2007.
Lesimple et al.; 2007.
Hajj, R. et al.; Stem Cells 25, 139-148 (2007).
Peter Dalgaard; Statistics and Computing, Introductory Statistics with R. Springer; 2002.
Gentleman, R., et al.; "Statistics for Biology and Health; Bioinformatics and Computational Biology Solutions Using R and Bioconductor"; Springer, 2005.
Marchal, L. et al.; Proc. Natl. Acad. Sci. USA 106 (41), 17437 (2009).
Kloosterman et al.; Nat. Methods 3 (1), 27 (2006).
Deblandre et al.; Development 126 (21), 4715 (1999).
Hayes, et al.; Dev. Biol. 312 (1), 115 (2007).
Pohl et al.; Dev. Genes Evol. 214 (4), 200 (2004).
Krasteva, G. et al.; (2006) Respir. Res. 7, 108.
Yang, G. et al.; (2008) Exp. Mol. Pathol. 84, 131-140.
Le Saux, C.J. et al.; (2008) J. Biol. Chem. 283, 5760-5768.
Norkin, L.C. et al.; (2001) Exp. Cell. Res. 266, 229-238.
Walters, R.W. et al.; (1999) J. Biol. Chem. 274, 10219-10226.
Pickles, R.J. et al.; (1996) Hum. Gene Ther. 7, 921-931.
Morichika et al.; Dev. Growth Differ. 52 (2), 235 (2010).

(Continued)

*Primary Examiner* — Amy Bowman
(74) *Attorney, Agent, or Firm* — Alston & Bird LLP

(57) ABSTRACT

The present invention relates to a method for evaluating the regenerative and/or differentiation capacity of ciliated epithelial tissue in a vertebrate subject, in particular a mammal, preferably a human, and to the use of microRNA in treating illnesses associated with a dysfunction of multiciliated epithelial cells.

23 Claims, 14 Drawing Sheets

(56) References Cited

OTHER PUBLICATIONS

Pottier, et al.; PLoS One 4 (8), e6718 (2009).
Edgar, et al.; Nucleic Acids Res. 30 (1), 201 (2002).
Feng, M. et al.; Cell Cycle 9 (2), 213 (2010).
Lize et al.; Cell Death Differ. (2009).
Noonan et al.; Oncogene 28 (14), 1714 (2009).
Yang, X. et al.; Genes Dev. 23 (20), 2388 (2009).
Tsao, et al.; Development 136 (13), 2297 (2009).
Dunnill, M. S., "The Pathology of Asthma, with Special Reference to Changes in the Bronchial Mucosa," *J. Clin. Path.*, 1960, vol. 13, pp. 27-33.
Song, R., et al., "miR-34/449 miRNAs are required for motile ciliogenesis by repressing *cp110*," *Nature*, 2014, vol. 510, pp. 115-120.
Thomas, B., et al., "Persistent disruption of ciliated epithelium following paediatric lung transplantation," *Eur. Respir. J.*, 2012, vol. 40, pp. 1245-1252.
Thomas, B., et al., "Ciliary dysfunction and ultrastructural abnormalities are features of severe asthma," *J. Allergy Clin. Immunol.*, 2010, vol. 126, pp. 722-729.
Yaghi, A., et al., "Ciliary beating is depressed in nasal cilia from chronic obstructive pulmonary disease subjects," *Respiratory Medicine*, 2012, vol. 106. pp. 1139-1147.

USE OF MICRORNA FOR TREATING DISEASES ASSOCIATED WITH A DYSFUNCTION OF THE CILIA IN MULTICILIATED EPITHELIAL CELLS

FIELD OF THE INVENTION

The present invention relates to the area of the regeneration and differentiation of ciliated epithelia in vertebrates, notably mammals, and in particular humans, leading to a functional ciliogenesis and to involvement of microRNAs in the process of regeneration and differentiation of said epithelia as well as to the genes modulated by said microRNAs.

The present invention relates more particularly to the use of microRNA in the treatment of diseases associated with a dysfunction of the cilia of multiciliated epithelial cells, especially disorders resulting from nonfunctional ciliogenesis, such as chronic respiratory diseases for which regeneration and/or differentiation of the airway epithelium is defective.

BACKGROUND OF THE INVENTION

The ciliated cells coating the apical surface of the epithelia are essential for various physiological processes such as cleaning of the respiratory passages, embryo implantation, or circulation of the cerebrospinal fluid. Defective ciliogenesis is the direct cause of or is associated with a great variety of diseases.

The process of ciliogenesis comprises a sequence of events that begins with acquisition of the identity of the ciliated cell (phase 1). This first step consists of lateral inhibition between two adjacent cells by the Notch signalling system via interaction between Notch and its ligand such as delta-like 1 (DLL1). The cell expressing the DLL1 ligand becomes a progenitor cell of ciliated cells, and simultaneously, activation of Notch in the neighbouring cells prevents transformation of these cells into progenitor cells of ciliated cells. The inventors have shown that the progenitor cell of ciliated cells expresses the microRNAs of the family miR-449 and the transcription factor FOXJ1. During a second phase, the miR-449s inhibit cell division and induce differentiation. Multiplication of the centrioles begins in the progenitor cell of ciliated cells, and this multiplication is followed by anchoring of the basal bodies to the apical pole of the cells; this step is followed by assembly of the axoneme and cilia synthesis proper.

The epithelia perform a barrier function between the internal medium and the external environment. The respiratory passages are coated with a highly differentiated pseudostratified epithelium consisting of mucus-secreting and ciliated basal cells (each ciliated cell having hundreds of cilia). The coordinated movement of these numerous cilia present on the surface of the epithelium permits the removal of waste carried by the mucus during a process called mucociliary clearance. In this connection, the cilia play an important role in the processes of defense against first-line respiratory tract infections (Puchelle et al. *Proc Am Thorac Soc* (2006) 3, 726-733).

The permanent exposure of the airway epithelium to environmental stresses caused by pathogenic microorganisms, allergens, toxic molecules, etc. leads to tissue lesions. Following these lesions, a physiological process of regeneration of the airway epithelium goes into action. This process, when successful, repairs the lesion and restores the integrity of the respiratory tissue, the lesion being replaced with tissue that is differentiated and is functional again.

This regeneration comprises several steps:
1) the epithelial cells proliferate and/or migrate in order to fill the wound bed;
2) these first steps are followed by activation of a step of cellular polarization characterized by the formation of tight junctions and by specific differential addressing of membrane proteins (channels, ion transporters etc.) between the apical pole and the basolateral pole (Puchelle et al. 2006; Hajj, R. et al. *J Pathol* (2007) 211, 340-350);
3) a stage of terminal differentiation leading to the formation of cilia on the surface of the ciliated cells (ciliogenesis) and to the presence of secretory cells responsible for the synthesis and secretion of mucus.

A pseudostratified mucociliary epithelium thus replaces the lesion, reconstituting a functional ciliated tissue having properties identical to those of the original tissue.

Taken together, these biological phenomena are associated with mechanisms of signal transduction and with particular gene expression profiles. Among certain known actors implicated in the differentiation and ciliogenesis of the airway epithelium, the Foxj1 transcription factor is one of the best documented (Yu, X. et al. (2008) *Nat Genet.* 40, 1445-1453). Foxj1 acts in a late phase of ciliogenesis, playing a role in anchoring of the basal bodies (small organelles of structural organization close to the centrioles that are indispensable for formation of the base of the cilia) to the apical membrane during formation of the axoneme (Gomperts, B. N. et al. (2004) *J Cell Sci* 117, 1329-1337 (2004).

In certain chronic respiratory diseases such as chronic obstructive pulmonary disease (COPD), mucoviscidosis, asthma or primary ciliary dyskinesia (PCD), inflammations and chronic infections lead to destruction of the respiratory tissue (Marshall, W. F. (2008) *J Cell Biol* 180, 17-21). For reasons that are still poorly understood, these diseases are associated with defects of epithelial regeneration and differentiation. These defects result in abnormal restructuring of the tissue, fibrosis and irreversible functional loss (Marshall, W. F., 2008). There is still no therapeutic treatment for these various diseases, and only symptomatic treatments are available for combating, with a varying degree of effectiveness, the progressive destruction of the respiratory tissue. In this connection, elucidation of the mechanisms leading to the formation of functional cilia (ciliogenesis) represents a major challenge with obvious therapeutic benefits.

Cellular differentiation involves fine temporal and spatial regulation of the transcription and translation governing the expression of specific genes. These events are controlled by various molecular and mechanical signals. Understanding the physiological mechanisms underlying differentiation and ciliogenesis is therefore an indispensable prelude to the development of therapeutic approaches that are more specific and more effective.

The microRNAs (miRNAs), small noncoding RNAs of about 22 bases discovered in 1993, which have regulatory properties, play a key role in the regulation of cellular phenomena such as survival, apoptosis, proliferation, homeostasis or differentiation (Lu, Y. et al. (2007) *Dev Biol* 310, 442-453).

Their mechanisms of action involve the formation of a complex between several bases of the miRNA and the non-coding 3' portion of the target mRNA. This interaction is said to induce destabilization of the target mRNA and/or inhibition of protein synthesis. Recognition between a miRNA and its target is mainly controlled by a sequence of about 7 bases, situated in the 5' portion of the miRNA (hereinafter, recognition sequence or seed). Accordingly, each miRNA would have the capacity to regulate the stability of a wide range of separate mRNAs.

To date, more than 750 miRNAs have been characterized in humans, where they are said to regulate more than 30% of the transcripts. Regulation by the miRNAs therefore appears to be a major regulation of gene expression, the impact of which has been underestimated until now (Berezikov, E. et al. (2005) Cell 120, 21-24; Xie, X. et al. (2005) Nature 434, 338-345).

The miRNAs are transcribed in the nucleus in the form of long precursors. They undergo a first maturation in the nucleus to give a precursor of miRNA (pre-miRNA) possessing a smaller hairpin structure. This precursor is exported from the nucleus to the cytoplasm where it will undergo a final maturation. Degradation of its loop by the enzyme Dicer generates two single-stranded miRNAs (a 5p strand and a 3p strand); the so-called mature strand is managed by a multiprotein complex (the RISC complex: RNA induced silencing complex) which interacts with the noncoding 3' portion of the target mRNAs, whereas the so-called "star" complementary strand will undergo a degradation; the complementary strand of a miRNA miR-xy, miR-xy-z or let-7x is designated, respectively, miR-xy*, miR-xy-z* or let-7x*.

Recent studies have demonstrated the importance of the microRNAs in the mouse in the mechanisms of differentiation and morphogenesis; in particular in embryonic development and the proliferation of the precursors of the epithelial cells of the epidermis (Lena, A. M. et al. (2008) Cell Death Differ 15, 1187-1195; Yi, R. et al. (2008) Nature 452, 225-229) or in lung development (Lu, Y. et al. (2007) Dev Biol 310, 442-453 (2007); Harris, K. S. et al. (2006) Proc Natl Acad Sci USA 103, 2208-2213; Lu, Y. et al. (2008) Proc Am Thorac Soc 5, 300-304). More precisely, Lena et al. demonstrated the involvement of the miRNAs of the locus miR-17-92 in pulmonary morphogenesis in the mouse. Although there is proof of the involvement of miRNAs during pulmonary morphogenesis in the mouse, their precise role(s) and their mechanisms of action have yet to be investigated.

Finally, several studies suggest a particular role of certain miRNAs in diseases such as cancers, cardiac hypertrophy, diabetes or certain viral infections (Triboulet, R. et al. (2007) Science 315, 1579-1582; Calin, G. A. & Croce, C. M. (2006) Nat Rev Cancer 6, 857-866; Grassmann, R. & Jeang, K. T. (2008) Biochim Biophys Acta 1779, 706-711; Latronico, M. V., (2008) Physiol Genomics 34, 239-242; Poy, M. N. et al. (2004) Nature 432, 226-230).

To date, no study has demonstrated the role or involvement of miRNAs in the regeneration and differentiation of ciliated epithelia, such as the airway epithelium, and the control of ciliogenesis in vertebrates.

SUMMARY OF THE INVENTION

Therefore the inventors have demonstrated for the first time the involvement of certain miRNAs in the control of ciliogenesis of epithelial tissues in vertebrates and, in particular, in the regeneration and differentiation of human airway epithelial cells in a mucociliary surface epithelium.

More particularly, the inventors used different experimental approaches combining high-throughput sequencing of miRNAs, miRNA biochips as well as quantitative RT-PCR and identified the miRNAs involved specifically in different stages of differentiation of the human airway epithelium and of ciliated epidermal cells of embryos of the frog Xenopus laevis, namely signatures of the specific miRNAs 1) of the proliferation step, 2) of cellular polarization and 3) of terminal differentiation and of ciliogenesis.

They also confirmed the role of the miRNAs thus identified in the control of ciliogenesis of epithelial tissues notably via repression of the DLL1 Notch ligand.

They thus showed that the role of the microRNAs demonstrated in regeneration and ciliogenesis of a human airway epithelial tissue could be extrapolated to the mechanism of ciliogenesis of any multiciliated epithelial tissue in vertebrates.

It has thus been demonstrated that 63 miRNAs are expressed or repressed and/or are present in a significant amount in healthy airway epithelial tissue during regeneration and differentiation (see Tables III, IV, V and VI). The finding of a change in expression of one or more miRNAs in a sick individual relative to a healthy individual is an indicator of a defect of regulation of the expression of one or more genes; this change can therefore be compensated by administering the underexpressed miRNA or miRNAs and/or by administering the antagomirs of the overexpressed miRNA or miRNAs.

The present invention thus finds applications for evaluating the capacity for regeneration and differentiation, and thus for leading to functional ciliogenesis, of the ciliated epithelial tissue of a subject; the invention also makes it possible to evaluate the capacity for regeneration and/or differentiation of an airway epithelial tissue of said subject; the method according to the invention is also of particular interest in the area of in vitro and in vivo diagnostics. The present invention thus relates to a method of evaluating the capacity of a ciliated epithelial tissue to lead to functional ciliogenesis in a vertebrate, notably mammalian, subject, preferably human, characterized in that it comprises the steps of:

(i) quantitative measurement of the level of expression of the miRNAs of the ciliated epithelial tissue of said subject;

(ii) establishment of the expression profile of the miRNAs of the ciliated epithelial tissue of said subject;

(iii) comparison of the expression profile of the miRNAs of said subject with the expression profile of miRNAs of healthy ciliated epithelial tissue of one or more other subjects, said profile comprising some or all of the miRNAs in Table I given below;

(iv) identification of at least one miRNA, the level of expression of which by said subject differs by at least a factor of 2 relative to the level of expression of the same miRNA by said other subject(s), i.e. for which any one of the expression levels represents at least twice the other level of expression; and (v) demonstration of a defect in capacity to lead to functional ciliogenesis of a ciliated epithelial tissue connected with an abnormality in expression of at least one miRNA of said subject if at least one miRNA of said profile established in step (ii) has a level of expression that differs by at least a factor of 2 relative to the level of expression of the same miRNA in the expression profile in Table I. When the level of expression is expressed in log 2 (as in Table I), this signifies that a defect in the capacity for regeneration and/or differentiation, and therefore for ciliogenesis, of a ciliated epithelial tissue connected with an abnormality of expression of at least one miRNA is observed when the level of expression in log 2 of the test subject varies by at least one unit relative to the expression profile in one or more other healthy subjects.

Application of the method according to the invention requires establishment of the expression profile of the miRNAs of the ciliated epithelial tissue of a subject for whom we wish to establish a diagnosis relating to the capacity for regeneration and/or differentiation of a ciliated epithelial tissue and of the expression profile of the miRNAs of the ciliated epithelial tissue of one or more healthy subjects, i.e. selected for not having a disorder of differentiation and/or regeneration and of ciliogenesis of the ciliated epithelial tissue.

According to another of its objects, the present invention relates to a method of evaluating the capacity for regeneration and/or differentiation and for leading to functional ciliogenesis of an airway epithelial tissue of a mammalian subject, preferably human, characterized in that it comprises the steps of:

(i) quantitative measurement of the level of expression of the miRNAs of the airway epithelial tissue of said subject;

(ii) establishment of the expression profile of the miRNAs of the airway epithelial tissue of said subject;

(iii) comparison of the expression profile of the miRNAs of said subject with the expression profile of the miRNAs of said healthy airway epithelial tissue of one or more other subjects, said profile comprising some or all of the miRNAs in Table I given below;

(iv) identification of at least one miRNA, the level of expression of which by said subject differs by at least a factor of 2 relative to the level of expression of the same miRNA by said other subject(s), i.e. for which any one of the expression levels represents at least twice the other level of expression; and (v) demonstration of a defect in the capacity for regeneration and/or differentiation of an airway epithelial tissue connected with an abnormality of expression of at least one miRNA of said subject if at least one miRNA of said profile established in step (ii) has a level of expression that differs by at least a factor of 2 relative to the level of expression of the same miRNA in the expression profile in Table I.

DEFINITIONS

"Subject" means a vertebrate individual, in particular mammalian, and preferably human. Preferably, the subject for which we wish to establish a diagnosis relating to the capacity of a ciliated epithelial tissue to lead to functional ciliogenesis, it can more specifically be a matter of diagnosing the capacity for regeneration and/or differentiation of an airway epithelial tissue and the healthy subject or subjects belong to the same species.

In the context of the present invention, the terms "ciliated" and "multiciliated" are used indiscriminately, it being understood that the epithelial tissues in question are such that their cells bear several cilia.

Expression profile of the miRNAs in a given tissue means all of the miRNAs having a level of expression greater than or equal to a selected value.

The level of expression of a miRNA in a cell or a tissue is determined by measuring the miRNAs present in the cell or tissue.

The level of expression of a miRNA can be measured by any technique known by a person skilled in the art; we may notably mention, after a step of RNA extraction, high-throughput sequencing of the miRNAs, sequencing by NASBA (nucleic acid strand based amplification), by primer extension, or DNA chips permitting hybridization of the miRNAs.

The level of expression of the miRNAs can be expressed by different means such as:

the level of intensity of expression in log 2, this value is representative of the amount of miRNA present in a cell or a tissue; for establishment of an expression profile, it is preferable to use the miRNAs that have a level of intensity of expression in log 2 greater than or equal to 3;

This level of intensity of expression can be calculated by different means depending on the technique used for measuring the miRNAs expressed.

In the case of measurement of fluorescence on chips of the Agilent type (see the examples given below), measurement of the level of expression corresponds to an intensity of fluorescence, from which log 2 is then calculated. In the case of high-throughput sequencing, the level of intensity of expression counts the number of times the sequence of a miRNA is sequenced, this number is normalized relative to the total number of sequences, and then its log 2 is calculated.

the abundance, which represents the percentage expression of a miRNA in a cell or a tissue relative to the total amount of miRNAs expressed in the same cell or the same tissue, in this case the miRNAs whose abundance is greater than or equal to 0.1%, preferably 0.5%, more preferably 1%, will be retained.

Preferably, the values characterizing the level of expression are expressed in log 2.

Table I given below describes the expression profile in which the level of expression is expressed as the level of intensity of expression in log 2 of the miRNAs of a healthy human airway epithelial tissue:

| Name of the miRNA | Sequence number of the miRNA (SEQ ID) | Level of intensity of expression in log2 At the differentiated stage (WD) measured in HTS |
|---|---|---|
| hsa-miR-100 | 1 | 9.00 |
| hsa-miR-106b | 2 | 5.39 |
| hsa-miR-125a-5p | 3 | 14.08 |
| hsa-miR-130a | 4 | 11.98 |
| hsa-miR-140-3p | 5 | 13.12 |
| hsa-miR-141 | 6 | 9.75 |
| hsa-miR-148a | 7 | 8.97 |
| hsa-miR-151-5p | 8 | 10.22 |
| hsa-miR-15a | 9 | 7.68 |
| hsa-miR-16 | 10 | 5.35 |
| hsa-miR-17 | 11 | 11.61 |
| hsa-miR-181a | 12 | 0.01 |
| hsa-miR-191 | 13 | 16.82 |
| hsa-miR-193b | 14 | 11.67 |
| Hsa-miR-1975 | 15 | 11.22 |
| hsa-miR-200a | 16 | 10.96 |
| hsa-miR-200b | 17 | 10.64 |
| hsa-miR-200c | 18 | 14.57 |
| hsa-miR-203 | 19 | 14.55 |
| hsa-miR-205 | 20 | 15.24 |
| hsa-miR-21 | 21 | 8.09 |
| Hsa-miR-21* | 73 | 10.49 |
| hsa-miR-210 | 22 | 9.29 |
| hsa-miR-22 | 23 | 11.22 |
| hsa-miR-224 | 24 | 14.10 |
| hsa-miR-23a | 25 | 15.35 |
| hsa-miR-23b | 26 | 9.35 |
| hsa-miR-25 | 27 | 3.52 |
| hsa-miR-26a | 28 | 7.75 |
| hsa-miR-26b | 29 | 6.81 |
| hsa-miR-27b | 30 | 14.81 |
| hsa-miR-29a | 31 | 14.53 |
| hsa-miR-29c | 32 | 9.74 |
| hsa-miR-30b | 33 | 0.01 |
| hsa-miR-30c | 34 | 10.87 |
| hsa-miR-30d | 35 | 8.76 |
| hsa-miR-30e | 36 | 12.74 |
| hsa-miR-31 | 37 | 11.83 |
| hsa-miR-31* | 89 | 11.18 |
| hsa-miR-34a | 38 | 13.75 |
| hsa-miR-34b | 39 | 10.65 |
| Hsa-miR-34b* | 91 | 14.29 |
| hsa-miR-34c-5p | 40 | 0.01 |
| hsa-miR-365 | 41 | 2.78 |
| hsa-miR-374a | 42 | 11.87 |

-continued

| Name of the miRNA | Sequence number of the miRNA (SEQ ID) | Level of intensity of expression in log2 At the differentiated stage (WD) measured in HTS |
|---|---|---|
| hsa-miR-378 | 43 | 11.70 |
| hsa-miR-425 | 44 | 9.53 |
| hsa-miR-429 | 45 | 15.11 |
| hsa-miR-449a | 46 | 12.24 |
| hsa-miR-449b | 47 | 14.56 |
| hsa-miR-449c | 201 | 10.98 |
| hsa-miR-574-3p | 48 | 13.42 |
| hsa-miR-92b | 49 | 0.01 |
| hsa-miR-939 | 50 | 5.43 |
| hsa-miR-96 | 51 | 12.65 |
| hsa-miR-99a | 52 | 9.00 |
| hsa-let-7a | 157 | 4.31 |
| hsa-let-7b | 158 | 11.28 |
| hsa-let-7c | 159 | 7.86 |
| hsa-let-7e | 160 | 7.60 |
| hsa-let-7f | 161 | 5.35 |
| hsa-let-7g | 162 | 12.40 |

The method according to the invention can have an additional step consisting of comparing the expression profile of microRNAs of ciliated epithelial tissue, notably respiratory, of the subject for which we desire to establish a diagnosis relating to the capacity to control functional ciliogenesis of said tissue, notably the capacity for regeneration and/or differentiation, with an expression profile of miRNAs of healthy ciliated epithelial tissue of one or more subjects established at a particular stage of differentiation, such a profile can be established with Table IV.

The present invention thus relates to at least one miRNA identified by the method according to the invention selected from hsa-miR-100, hsa-miR-106b, hsa-miR-125a-5p, hsa-miR-130a, hsa-miR-140-3p, hsa-miR-141, hsa-miR-151-5p, hsa-miR-15a, hsa-miR-16, hsa-miR-17, hsa-miR-181a, hsa-miR-191, hsa-miR-193b, hsa-miR-1975, hsa-miR-200a, hsa-miR-200b, hsa-miR-200c, hsa-miR-203, hsa-miR-205, hsa-miR-21, hsa-miR-210, hsa-miR-22, hsa-miR-224, hsa-miR-23a, hsa-miR-23b, hsa-miR-25, hsa-miR-26a, hsa-miR-26b, hsa-miR-27b, hsa-miR-29a, hsa-miR-29c, hsa-miR-30b, hsa-miR-30c, hsa-miR-30d, hsa-miR-30e, hsa-miR-31, hsa-miR-34a, hsa-miR-34b, hsa-miR-34c-5p, hsa-miR-365, hsa-miR-374a, hsa-miR-378, hsa-miR-425, hsa-miR-429, hsa-miR-449a, hsa-miR-449b, hsa-miR-449c, hsa-miR-574-3p, hsa-miR-92b, hsa-miR-939, hsa-miR-96, hsa-miR-99a, hsa-let-7a, hsa-let-7b, hsa-let-7c, hsa-let-7e, hsa-let-7f and hsa-let-7g of sequence SEQ ID No. 1 to 6, 8 to 52, 157 to 162 and 201 (see Table I below), their "star" complementary strand of sequence SEQ ID No. 53 to 58, 60 to 104, 163 to 168 and 202, or the complementary sequence strand optionally modified chemically, and their precursor of sequence SEQ ID No. 105 to 110, 112 to 156, 169 to 174, 193 to 200 and 203 for use for the prevention and/or treatment of disorders associated with a dysfunction of the cilia of ciliated epithelial tissue.

Ciliated epithelial tissue means a tissue whose cells bear cilia on their apical surface; in mammals, it is notably the airway epithelium or the epithelium of the Fallopian tubes and the endometrium of the uterus, of the choroid plexus and ependymal cells in the brain, and of the spermatozoa, rete testis and vas deferens in the male.

Complementary sequence strand of a given first single-stranded nucleic acid fragment means the single-stranded nucleic acid fragment whose sequence is the complement of the sequence of said first fragment and is capable of pairing with said first fragment.

In the context of the invention, chemically modified complementary-sequence strands can be used, i.e. their sequence comprises one or more bases that have been modified chemically, in order to improve their intracellular and extracellular stability and make them less sensitive to hydrolysis in acid or basic conditions as well as under the action of nucleases; the modifications that are conceivable are notably those listed for the interfering RNAs (siRNA) in the review of T. M. Rana (Nature Reviews, 2007, Vol. 8: 23-36) or as described in application WO 2007/021896; in particular, complementary-sequence strands can comprise a chemically modified nucleotide selected from the nucleotides modified in 2' such as a 2'-deoxy, 2'-deoxy-2'-fluoro, 2'-O-methyl, 2'-O-methoxyethyl (2'-O-MOE), 2'-O-aminopropyl (2'-OAP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE) or 2'-O—N-methylacetamido (2'-O-NMA) base.

TABLE II miRNAs according to the invention and reference of their nucleotide sequence, of the nucleotide sequence of their complementary strand and of that of their precursor

| Name and Sequence (SEQ ID number) of the miRNAs | Name and sequence (SEQ ID number) of the complementary strand | | Sequence of the precursor (SEQ ID number) |
|---|---|---|---|
| hsa-miR-100 | 1 | hsa-miR-100* | 53 | 105 |
| hsa-miR-106b | 2 | hsa-miR-106b* | 54 | 106 |
| hsa-miR-125a-5p | 3 | hsa-miR-125a-3p | 55 | 107 |
| hsa-miR-130a | 4 | hsa-miR-130a* | 56 | 108 |
| hsa-miR-140-3p | 5 | hsa-miR-140-5p | 57 | 109 |
| hsa-miR-141 | 6 | hsa-miR-141* | 58 | 110 |
| hsa-miR-148a | 7 | hsa-miR-148a* | 59 | 111 |
| hsa-miR-151-5p | 8 | hsa-miR-151-3p | 60 | 112 |
| hsa-miR-15a | 9 | hsa-miR-15a* | 61 | 113 |
| hsa-miR-16 | 10 | hsa-miR-16* | 62 | 114, 193 |
| hsa-miR-17 | 11 | hsa-miR-17* | 63 | 115 |
| hsa-miR-181a | 12 | hsa-miR-181a* | 64 | 116, 194 |
| hsa-miR-191 | 13 | hsa-miR-191* | 65 | 117 |
| hsa-miR-193b | 14 | hsa-miR-193b* | 66 | 118 |
| Hsa-miR-1975 | 15 | Hsa-miR-1975* | 67 | 119 |
| hsa-miR-200a | 16 | hsa-miR-200a* | 68 | 120 |
| hsa-miR-200b | 17 | hsa-miR-200b* | 69 | 121 |
| hsa-miR-200c | 18 | hsa-miR-200c* | 70 | 122 |
| hsa-miR-203 | 19 | hsa-miR-203* | 71 | 123 |
| hsa-miR-205 | 20 | hsa-miR-205* | 72 | 124 |
| hsa-miR-21 | 21 | hsa-miR-21* | 73 | 125 |
| hsa-miR-210 | 22 | hsa-miR-210* | 74 | 126 |
| hsa-miR-22 | 23 | hsa-miR-22* | 75 | 127 |
| hsa-miR-224 | 24 | hsa-miR-224* | 76 | 128 |
| hsa-miR-23a | 25 | hsa-miR-23a* | 77 | 129 |
| hsa-miR-23b | 26 | hsa-miR-23b* | 78 | 130 |
| hsa-miR-25 | 27 | hsa-miR-25* | 79 | 131 |
| hsa-miR-26a | 28 | hsa-miR-26a* | 80 | 132, 195 |
| hsa-miR-26b | 29 | hsa-miR-26b* | 81 | 133 |
| hsa-miR-27b | 30 | hsa-miR-27b* | 82 | 134 |
| hsa-miR-29a | 31 | hsa-miR-29a* | 83 | 135 |
| hsa-miR-29c | 32 | hsa-miR-29c* | 84 | 136 |
| hsa-miR-30b | 33 | hsa-miR-30b* | 85 | 137 |
| hsa-miR-30c | 34 | hsa-miR-30c* | 86 | 138, 196 |
| hsa-miR-30d | 35 | hsa-miR-30d* | 87 | 139 |
| hsa-miR-30e | 36 | hsa-miR-30e* | 88 | 140 |
| hsa-miR-31 | 37 | hsa-miR-31* | 89 | 141 |
| hsa-miR-34a | 38 | hsa-miR-34a* | 90 | 142 |
| hsa-miR-34b | 39 | hsa-miR-34b* | 91 | 143 |
| hsa-miR-34c-5p | 40 | hsa-miR-34c-3p | 92 | 144 |
| hsa-miR-365 | 41 | hsa-miR-365* | 93 | 145, 197 |
| hsa-miR-374a | 42 | hsa-miR-374a* | 94 | 146 |
| hsa-miR-378 | 43 | hsa-miR-378* | 95 | 147 |
| hsa-miR-425 | 44 | hsa-miR-425* | 96 | 148 |
| hsa-miR-429 | 45 | hsa-miR-429* | 97 | 149 |
| hsa-miR-449a | 46 | hsa-miR-449a* | 98 | 150 |
| hsa-miR-449b | 47 | hsa-miR-449b* | 99 | 151 |
| hsa-miR-449c | 201 | hsa-miR-449c* | 202 | 203 |

TABLE II-continued miRNAs according to the invention and reference of their nucleotide sequence, of the nucleotide sequence of their complementary strand and of that of their precursor

| Name and Sequence (SEQ ID number) of the miRNAs | | Name and sequence (SEQ ID number) of the complementary strand | | Sequence of the precursor (SEQ ID number) |
|---|---|---|---|---|
| hsa-miR-574-3p | 48 | hsa-miR-574-5p | 100 | 152 |
| hsa-miR-92b | 49 | hsa-miR-92b* | 101 | 153 |
| hsa-miR-939 | 50 | hsa-miR-939* | 102 | 154 |
| hsa-miR-96 | 51 | hsa-miR-96* | 103 | 155 |
| hsa-miR-99a | 52 | hsa-miR-99a* | 104 | 156 |
| hsa-let-7a | 157 | hsa-let-7a* | 163 | 169, 198, 199 |
| hsa-let-7b | 158 | hsa-let-7b* | 164 | 170 |
| hsa-let-7c | 159 | hsa-let-7c* | 165 | 171 |
| hsa-let-7e | 160 | hsa-let-7e* | 166 | 172 |
| hsa-let-7f | 161 | hsa-let-7f* | 167 | 173, 200 |
| hsa-let-7g | 162 | hsa-let-7g* | 168 | 174 |

The miRNAs according to the present invention are thus of particular interest for the prevention and/or treatment of so-called primary ciliopathies, i.e. which are directly associated with a dysfunction of the cilia, these primary ciliopathies are notably:
- primary ciliary dyskinesia or Kartagener syndrome;
- situs invertus;
- male infertility (motility of the spermatozoa) and female infertility (e.g. ectopic pregnancies);
- Alstrom syndrome;
- Bardet-Biedl syndrome;
- Meckel-Gruber syndrome;
- polycystic kidney;
- retinal degeneration;
- Senior-Løken syndrome.

The miRNAs according to the present invention are also of interest for the prevention and/or treatment of so-called secondary ciliopathologies, i.e. which are associated with a defect of function of the cilia such as:
- mucoviscidosis;
- chronic obstructive pulmonary disease (COPD);
- asthma;
- bronchiolitis;
- respiratory infections of viral origin.

The use according to the present invention therefore finds applications more particularly in the prevention and/or treatment of pathologies involving a disorder of regeneration and/or of differentiation of the airway epithelium; these pathologies are notably chronic and/or hereditary respiratory diseases such as chronic obstructive pulmonary disease (COPD), mucoviscidosis, asthma, primary ciliary dyskinesia, chronic inflammations and infections of the respiratory passages and respiratory failure.

The chronic and/or hereditary respiratory diseases (e.g. COPD, mucoviscidosis, asthma, PCD, allergic rhinitis etc.) represent a major public health problem, the fourth cause of mortality in the industrialized countries, and with rapidly increasing prevalence, hence the urgent need for better understanding of the causes and mechanisms of these diseases so that their treatments can be better targeted.

Asthma is the commonest of the chronic respiratory diseases in children (5 to 20%) and represents one of the major causes of hospitalization. The upsurge in respiratory allergies and the increase in industrial pollution contribute to the large increase in cases of asthma in the general population (0 van Schayck, et al. IPAG DIAGNOSIS & MANAGEMENT HANDBOOK. Chronic Airways Diseases. A Guide for Primary Care Physicians. 1-34, 2005).

The COPDs are a group of respiratory diseases associated with high morbidity and high mortality. COPDs are caused by inhaled toxic particles, tobacco being the most representative, which will lead to inflammation and to chronic infections that weaken the respiratory tissue. About 15% of smokers are likely to develop a COPD in their life. The World Health Organization estimates that there are nearly 1.1 billion smokers in the world, with a prevalence of COPD from 0.8 to 6% of the world population. Studies predict that in 2020, COPDs will represent the third cause of mortality in the world. Although the causes and mechanisms of these diseases are still largely unknown, it is probable that other factors (genetic, epigenetic) are likely to influence the development of COPD (0 van Schayck, et al. 2005).

Mucoviscidosis is the commonest hereditary genetic disease in the Caucasian population (1 birth out of 2500), affecting the exocrine glands and therefore all of the secretory epithelial tissue of the various organs (lungs, pancreas, liver, sweat glands, intestines). Defects of ion transport through the epithelia lead to a thickening of the mucus, notably responsible for inflammation and chronic respiratory infections, resulting in irreversible tissue destruction and to severe respiratory failure. There is no treatment for curing this disease, but advances in scientific and medical knowledge have made it possible to establish symptomatic treatments that have increased patients' life expectancy from 3 years in the 1960s to about 45 years today.

Primary ciliary dyskinesia (PCD) is a rare recessive autosomal disease (1 birth out of 15000) causing a defect of mobility of the cilia of the airway epithelium leading to defective mucociliary clearance, inflammations and chronic infections and irreversible tissue destruction.

The interest of these miRNAs with a view to treatment of diseases involving a disorder of regeneration and/or of differentiation of the airway epithelium is confirmed by the fact that these miRNAs regulate genes that are known to be involved in the regeneration and/or differentiation of the airway epithelium (see example III below).

In the context of the invention, it is preferable to use miRNAs that are present in significant quantity within the ciliated epithelial tissue during the process of ciliogenesis (preferably, the abundance of which is at least 1% of the total miRNAs, see Table III). Thus, it is preferable to use at least one miRNA selected from hsa-miR-34a (SEQ ID No. 38), hsa-miR-34b (SEQ ID No. 39), hsa-miR-34c-5p (SEQ ID No. 40), hsa-miR-449a (SEQ ID No. 46), hsa-miR-449b (SEQ ID No. 47), hsa-miR-449b* (SEQ ID No. 99), hsa-miR-449c (SEQ ID No. 201), hsa-miR-92b (SEQ ID No. 49), hsa-miR-1975 (SEQ ID No. 15), hsa-miR-99a (SEQ ID No. 52), hsa-miR-191 (SEQ ID No. 13), hsa-miR-378 (SEQ ID No. 43), hsa-miR-23b (SEQ ID No. 26), hsa-miR-125a-5p (SEQ ID No. 3), hsa-miR-203 (SEQ ID No. 19), hsa-miR-574-3p (SEQ ID No. 48), hsa-miR-29c (SEQ ID No. 32), hsa-miR-140-3p (SEQ ID No. 5), hsa-miR-205 (SEQ ID No. 20), hsa-miR-23a (SEQ ID No. 25), hsa-miR-31 (SEQ ID No. 37), hsa-miR-31* (SEQ ID No. 89), hsa-miR-21 (SEQ ID No. 21), hsa-miR-17 (SEQ ID No. 11), hsa-miR-29a (SEQ ID No. 31), hsa-miR-193b (SEQ ID No. 14), hsa-miR-210 (SEQ ID No. 22) and hsa-miR-130a (SEQ ID No. 4), their "star" complementary strand of sequence SEQ ID No. 55 to 57, 63, 65 to 67, 71 to 74, 77, 78, 83, 84, 90 to 92, 95, 98, 100, 101, 104 and 202, their complementary sequence strand optionally chemically modified, and their precursors of SEQ ID No. 107 to 109, 115, 117 to 119, 123 to 126, 129, 130, 135, 136, 141 to 144, 147, 151 to 153, 156 and 203.

Among these miRNAs, those whose expression is induced can be distinguished from those whose expression is repressed (Table IV); in order to reproduce a miRNA expression profile comparable to that of a healthy individual, it appears to be advantageous to use one or more miRNAs whose expression is induced and/or one or more miRNA antagomirs whose expression is repressed during the process of ciliogenesis of the ciliated epithelial tissues and, notably, of regeneration and of differentiation of the airway epithelial tissue. Thus, according to an advantageous variant of the invention, at least one miRNA is used according to the invention, selected from hsa-miR-34a (SEQ ID No. 38), hsa-miR-34b (SEQ ID No. 39), hsa-miR-34c-5p (SEQ ID No. 40), hsa-miR-449a (SEQ ID No. 46), hsa-miR-449b (SEQ ID No. 47), hsa-miR-449b* (SEQ ID No. 99), hsa-miR-449c (SEQ ID No. 201), hsa-miR-92b (SEQ ID No. 49), hsa-miR-1975 (SEQ ID No. 15), hsa-miR-99a (SEQ ID No. 52), hsa-miR-191 (SEQ ID No. 13), hsa-miR-378 (SEQ ID No. 43), hsa-miR-23b (SEQ ID No. 26), hsa-miR-125a-5p (SEQ ID No. 3), hsa-miR-203 (SEQ ID No. 19), and their precursors of sequence SEQ ID No. 107, 117, 119, 123, 130, 142 to 144, 147, 150, 151, 153, 156 and 203 and/or at least one "star" complementary strand of the miRNAs selected from hsa-miR-205, hsa-miR-31, hsa-miR-21, hsa-miR-17, hsa-miR-29a, hsa-miR-193b, hsa-miR-31*, hsa-miR-210 and hsa-miR-130a; these "star" complementary strands are hsa-miR-205* (SEQ ID No. 72), hsa-miR-31 and hsa-miR-31* (SEQ ID No. 37 and 89), hsa-miR-21* (SEQ ID No. 73), hsa-miR-17* (SEQ ID No. 63), hsa-miR-29a* (SEQ ID No. 83), hsa-miR-193b* (SEQ ID No. 66), hsa-miR-210* (SEQ ID No. 74), hsa-miR-130a* (SEQ ID No. 56) and their precursors of sequence SEQ ID No. 108, 115, 118, 124 to 126, 135 and 141.

Among said miRNAs whose expression is modulated during the process of ciliogenesis of the ciliated epithelial tissues, and notably of regeneration and/or differentiation of the airway epithelial tissue, those whose expression is induced are preferably used according to the invention: hsa-miR-34a (SEQ ID No. 38), hsa-miR-34b (SEQ ID No. 39), hsa-miR-34c-5p (SEQ ID No. 40), hsa-miR-449a (SEQ ID No. 46), hsa-miR-449b (SEQ ID No. 47), hsa-miR-449c (SEQ ID No. 201), hsa-miR-449b* (SEQ ID No. 99), hsa-miR-92b (SEQ ID No. 49), hsa-miR-1975 (SEQ ID No. 15), hsa-miR-99a (SEQ ID No. 52), hsa-miR-191 (SEQ ID No. 13), hsa-miR-378 (SEQ ID No. 43), hsa-miR-23b (SEQ ID No. 26), hsa-miR-125a-5p (SEQ ID No. 3), hsa-miR-203 (SEQ ID No. 19), and their precursors of sequence SEQ ID No. 107, 117, 119, 123, 130, 142 to 144, 147, 150, 151, 153, 156 and 203.

The present invention also relates to the use of expression vectors expressing at least one miRNA whose expression is induced during the process of ciliogenesis of an epithelial tissue or during the process of regeneration and/or differentiation of the airway epithelial tissue. Any expression vector capable of expressing RNAs in a eukaryotic cell and into which an expression cassette of a miRNA is cloned can be used in the context of the present invention.

The invention also relates to the use of miRNAs having the recognition sequence GGCAGUG (SEQ ID No. 175) positioned in region 2-7 of the miRNA, i.e. from the 2nd to the 7th nucleotide of the miRNA, or in region 3-8 of the miRNA, i.e. from the 3rd to the 8th nucleotide of the miRNA; they are notably the miRNAs hsa-miR-34a (SEQ ID No. 38), hsa-miR-34c-5p (SEQ ID No. 40), hsa-miR-449a (SEQ ID No. 46), hsa-miR-449b (SEQ ID No. 47) and hsa-miR-449c (SEQ ID No. 201).

The invention also relates to the use of miRNAs having the recognition sequence AAUCACU (SEQ ID No. 176) positioned in region 2-7 or in region 3-7 of the miRNA; it is notably the miRNA hsa-miR-34b (SEQ ID No. 39).

The invention further relates to the use of miRNAs having the recognition sequence AUCACUA (SEQ ID No. 177) positioned in region 2-7 or in region 3-7 of the miRNA; it is notably the miRNA hsa-miR-34c-3p (SEQ ID No. 40).

The invention finally relates to the use of at least one miRNA described above selected from the miRNAs of sequence SEQ ID No. 3-5, 8, 9, 11-15, 17, 19, 20, 23-26, 28-32, 35-37, 39-44, 46-52 and 201, their complementary strand or antagomir of sequence SEQ ID No. 55-57, 60, 61, 63-67, 69, 71, 72, 7578, 80-84, 87-89, 91-96, 98-104 and 202, optionally modified chemically, and their precursor of sequence SEQ ID No. 107-109, 112, 113, 115-119, 121, 123, 124, 127-130, 132-136, 139-141, 143-148, 150-156, 194, 195, 197 and 203 for use as a medicinal product.

BRIEF DESCRIPTION OF THE DRAWINGS

Besides the arrangements given above, the invention further comprises other arrangements which will become clear from the description presented below, which refer to examples of implementing the present invention, as well as to the appended drawings in which:

FIGURES

Figure 1:
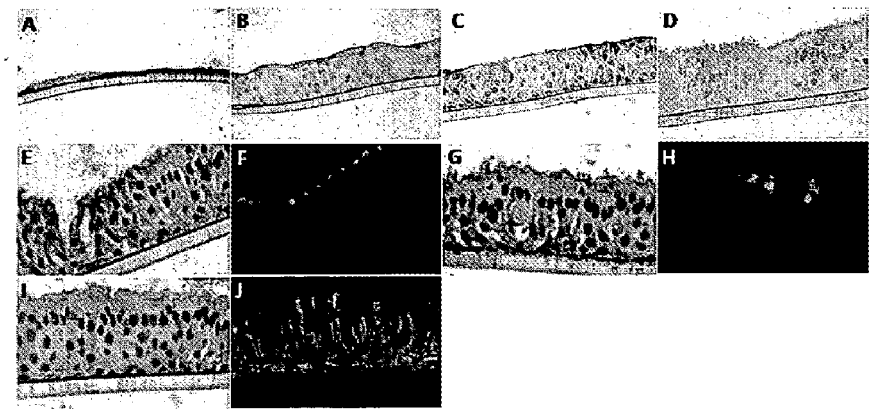

FIG. 1 shows micrographs of primary cultures of human airway epithelial cells observed by confocal and electron microscopy, revealing the morphology of the cells marked with hematoxylin and with eosin. The cells were also immunolabeled in order to examine the expression of epithelial markers of differentiation (tubulin-β4 for the ciliated cells (FIGS. 1E-F), mucin MUC5AC for the mucus-secreting cells (FIGS. 1G-H), and cytokeratin 13 for the basal cells (FIGS. 1I-J)). The states of differentiation were evaluated.

Figure 2A:
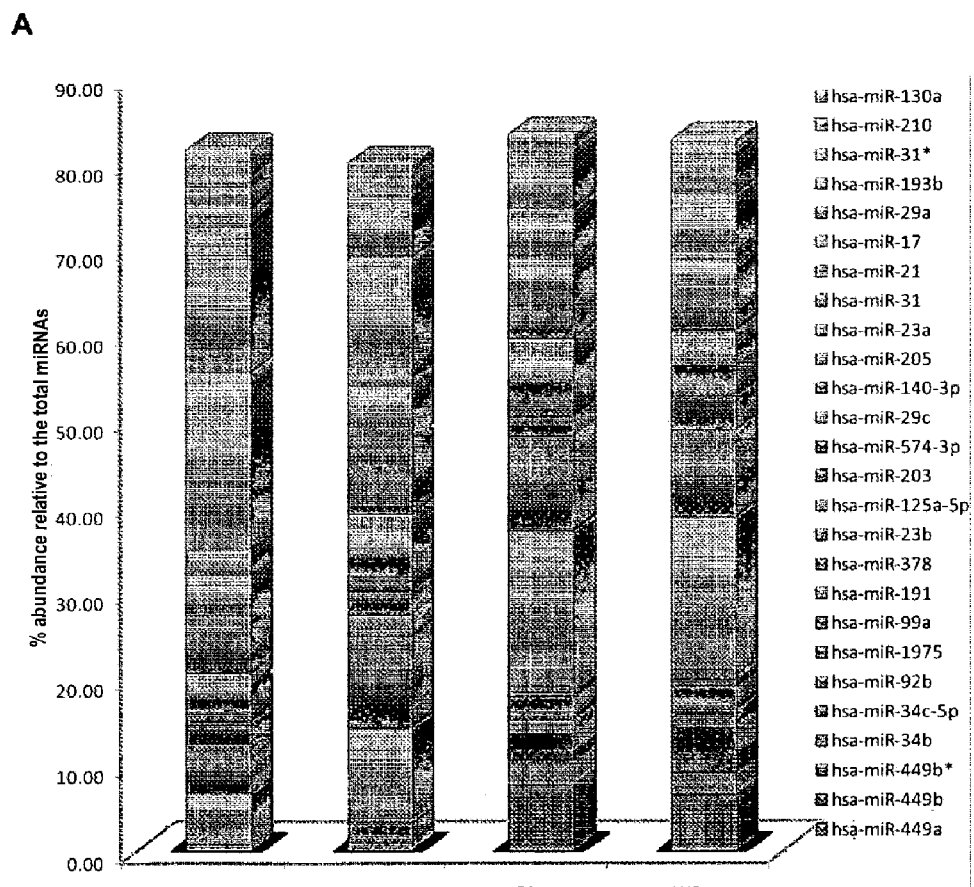
Figure 2B:
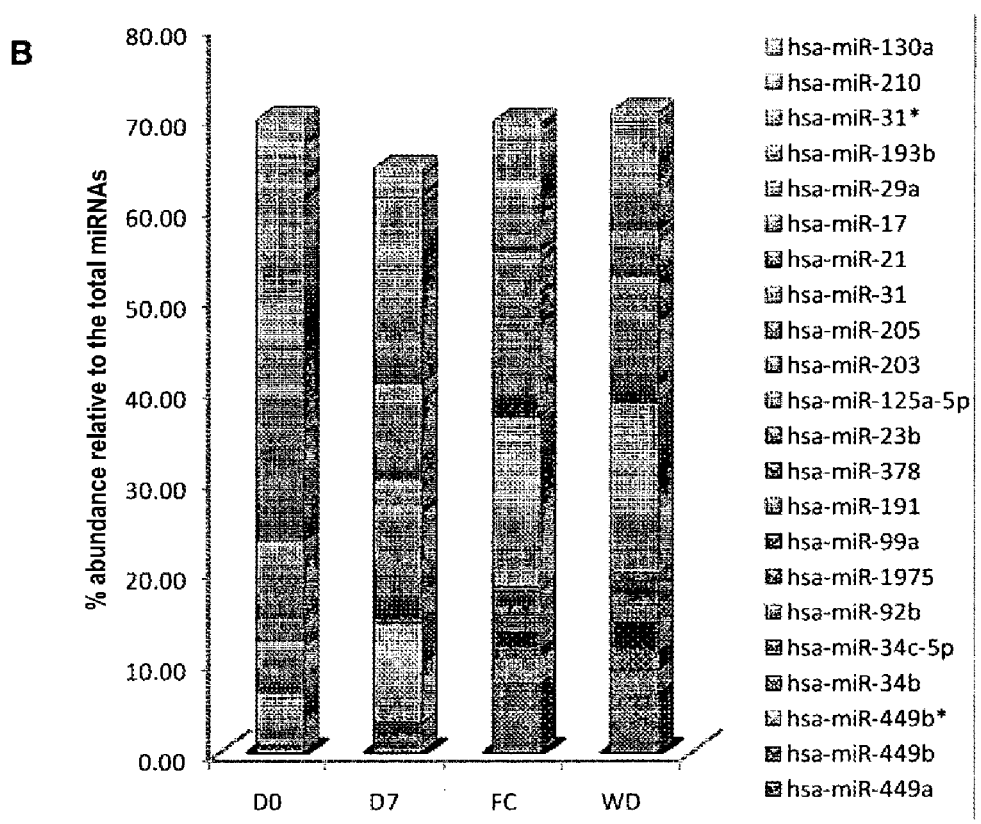

FIG. 2A presents cumulative histograms showing the 26 miRNAs having the strongest expression in at least one of the different stages of differentiation of the human airway epithelium in 3 separate patients: ALI-D0 (D0, proliferation), ALI-D7 (D7, proliferation and polarization), ALI-FC (FC, start of ciliogenesis), ALI-WD (WD, wholly differentiated epithelium). FIG. 2B presents cumulative histograms showing the 22 miRNAs that have the strongest expression and are significantly modulated in at least one of the different stages of differentiation of the human airway epithelium in 3 separate patients: ALI-D0 (D0, proliferation), ALI-D7 (D7, proliferation and polarization), ALI-FC (FC, start of ciliogenesis), ALI-WD (WD, wholly differentiated epithelium).

Figure 3:
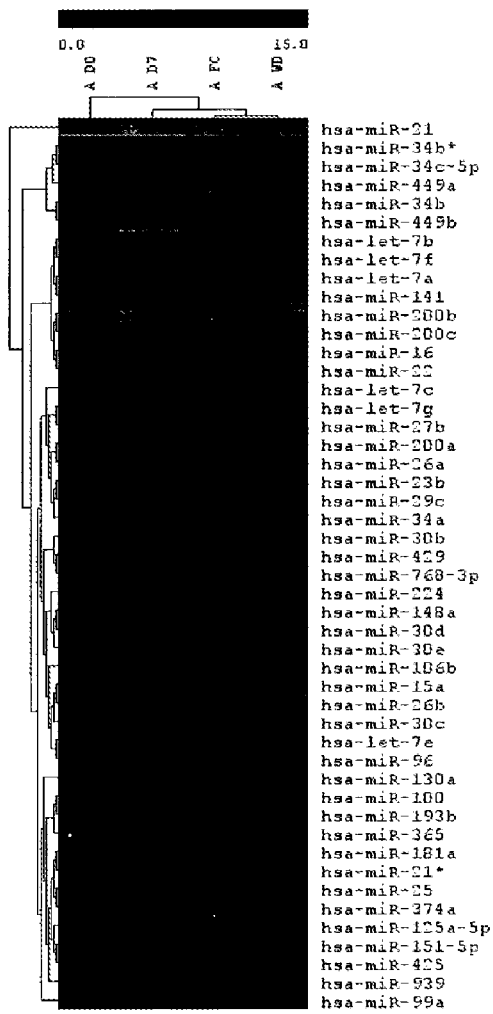

FIG. 3 shows a hierarchic cluster obtained by Agilent® miRNA chips showing the variations in intensity of expression of the miRNAs expressed statistically (A>8, P<0.05) and modulated in at least one condition of cellular culture (1<M<−1) (the darker the boxes, the less the miRNAs are expressed) as a function of the states of differentiation of the cellular cultures.

Figure 4:
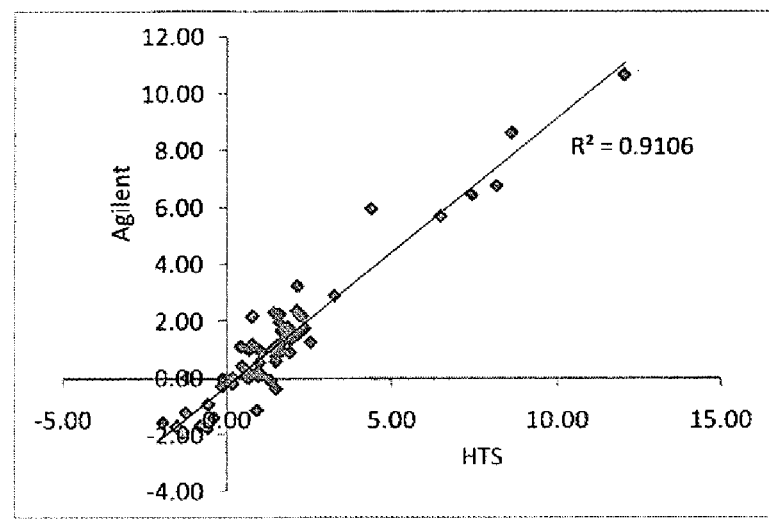

FIG. 4 is a graph showing the correlation between the results obtained in high-throughput sequencing (HTS) and in miRNA chips (Agilent®).

Figure 5:
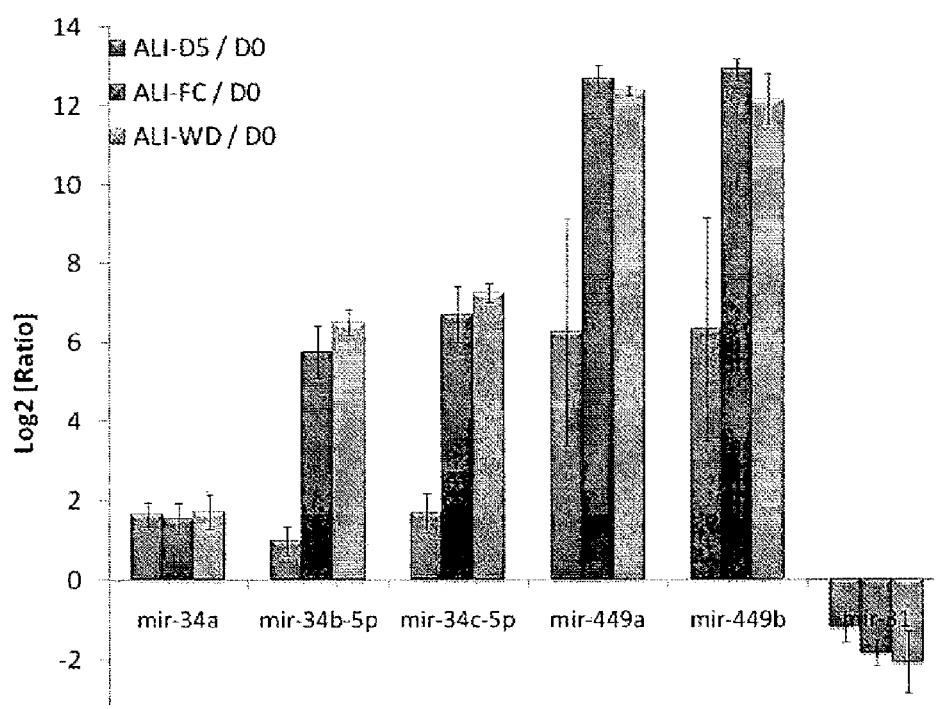

FIG. 5 shows a histogram of the variations observed by quantitative PCR of the 5p strands of each of the miRNAs tested at each stage of differentiation as indicated on the diagram. The results show the average of 3 separate donors.

Figure 6:
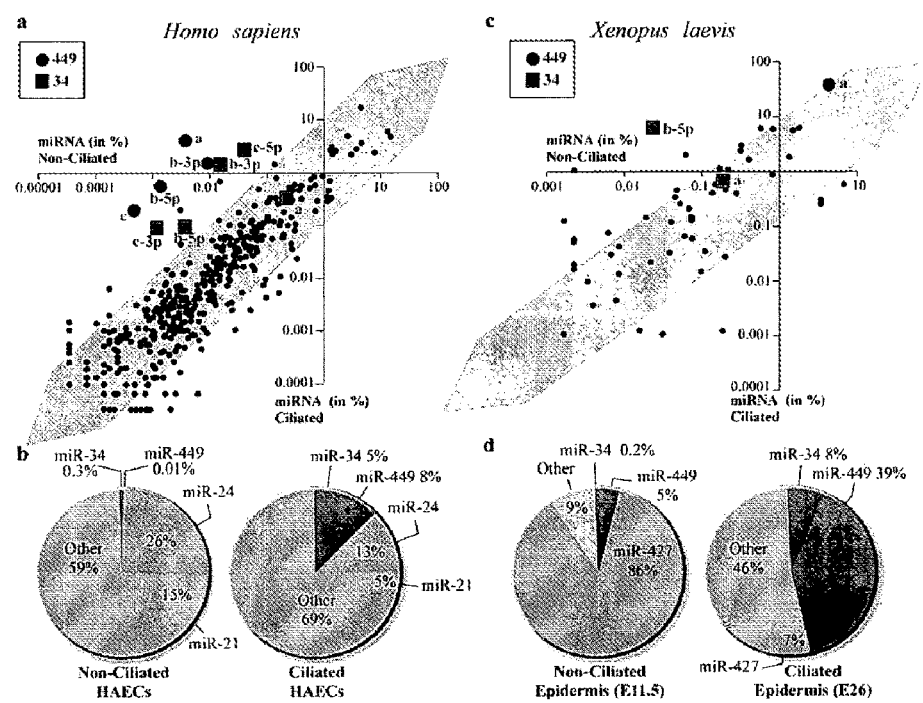

FIG. 6 combines two graphs showing the microRNAs regulated during ciliogenesis. Diagrams a and c show the abundance of the microRNAs as a percentage relative to the total microRNAs in undifferentiated HAEC cells (not ciliated, stage ALI-D0) (diagram a) and in an epidermal explant of Xenopus embryo before embryonic stage E11.5 (gastrula)

and after stage E26 (tail bud) (diagram c). Diagrams b and d repeat the same data and illustrate the quantitative abundance of the miRNAs.

Figure 7:
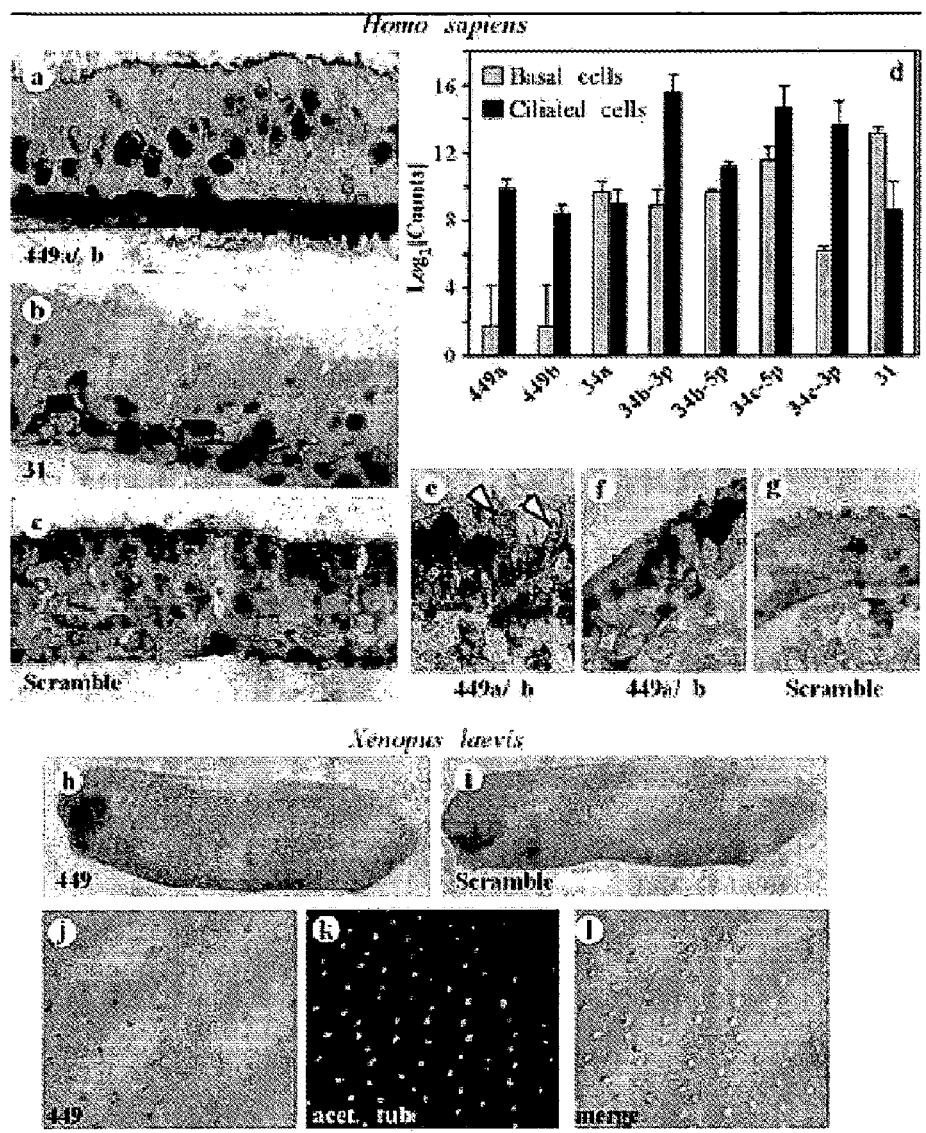

FIG. 7 presents micrographs for visualizing the specific localization of miR-449 in the ciliated cells. These tests were performed by hybridization in situ on frozen sections from culture of HAEC cells at 21 days (stage ALI-D21) (micrographs a, b, c), of human bronchial tissues (micrographs e, f, g) or from *Xenopus* embryos at the tail bud stage (micrographs h, i, j, k, l) using LNA probes labeled with digoxigenin and directed against miR-449 (micrographs a, e, f, h, i, j, l) or against miR-31 (micrograph b) and random probes ("scramble") as negative control (micrographs c, g, i). The ciliated cells of *Xenopus* embryo were identified by immunocytolabeling with a primary antibody directed against acetylated tubulin. The LNA probes directed against miR-449 label the ciliated cylindrical cells (micrographs a, e, h). Conversely, the probes directed against miR-31 labeled the basal cells preferentially (micrograph b). The mucus-secreting cells were labeled with anti-mucin antibody MUC5AC (indicated by arrows in panel e). Diagram d illustrates the levels of expression of miR-449, miR-31 and miR-34 in the basal cells of the epithelial tissue of human respiratory passages and in ciliated cylindrical cells.

Figure 8:
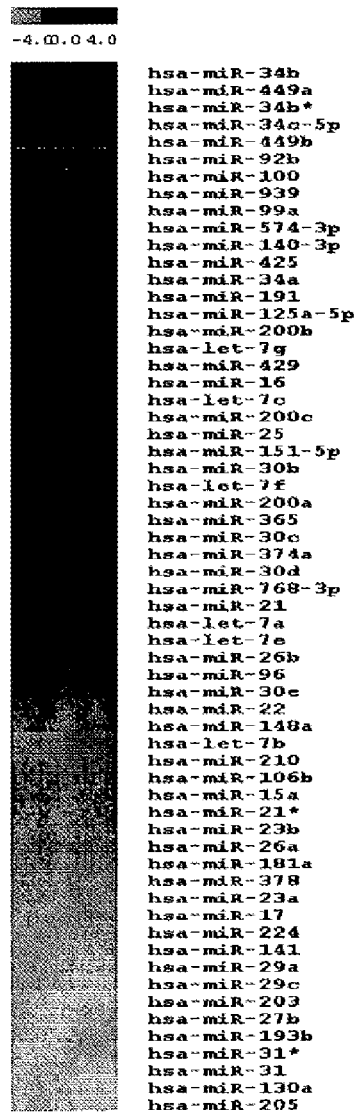

FIG. 8 shows a mapping (heat-map) of the microRNAs significantly regulated between pyramidal cells (ciliated+ secretory) versus basal cells. The 5 microRNAs located at the top of the column are specific to pyramidal cells (ciliated+ secretory); below these, the lighter the appearance of the miRNAs, the more they are specific to the basal cells.

Figure 9:
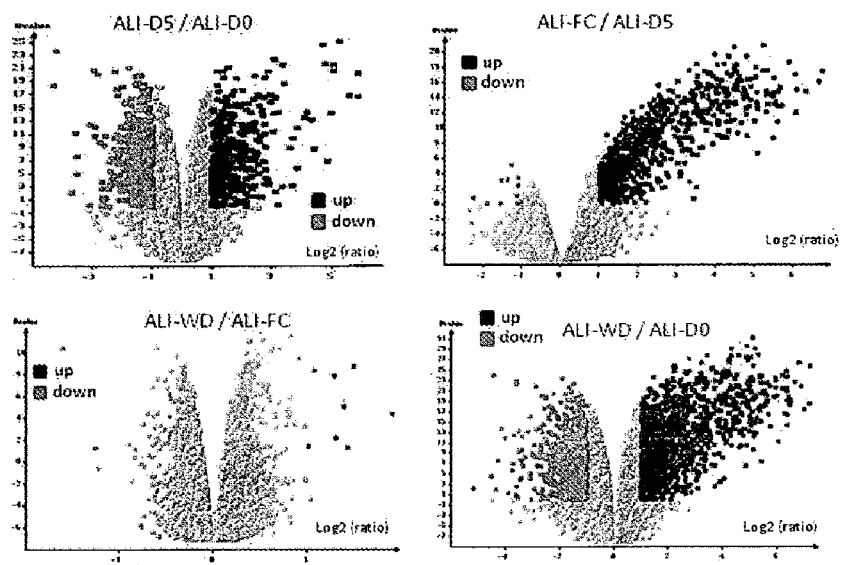

FIG. 9 is a graph showing the relations between $\log_2$ of the ratio at two stages of differentiation (abscissa) and the value of statistical significance (ordinate) for each of the 2 by 2 comparisons indicated on the diagram. The genes that are significantly overexpressed are shown in dark gray (right-hand side of the graph) and the genes that are significantly repressed are shown in medium gray (left-hand side of the graph).

Figure 10:
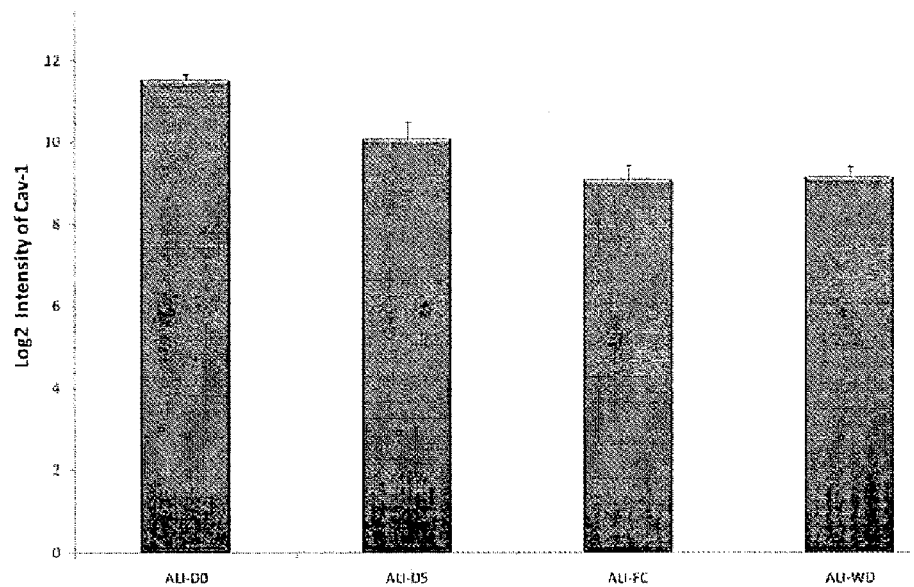

FIG. 10 is a histogram showing the $\log_2$ of the intensity of expression of the mRNA of caveolin-1 in each of the culture conditions investigated, as indicated on the diagram.

Figure 11:
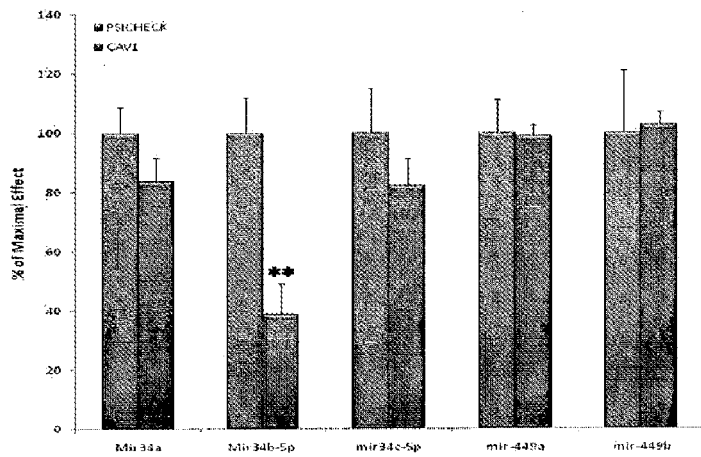

FIG. 11 is a histogram showing the effect of each of the miRNAs selected on the activity of luciferase (expressed relative to the % of the maximum effect obtained with the control vector PSICHECK) when the reporter gene of luciferase is fused to the noncoding 3' portion of the mRNA of Cav-1 versus the control (PSICHECK). The data were normalized relative to the results obtained with a negative control miRNA.

Figure 12:
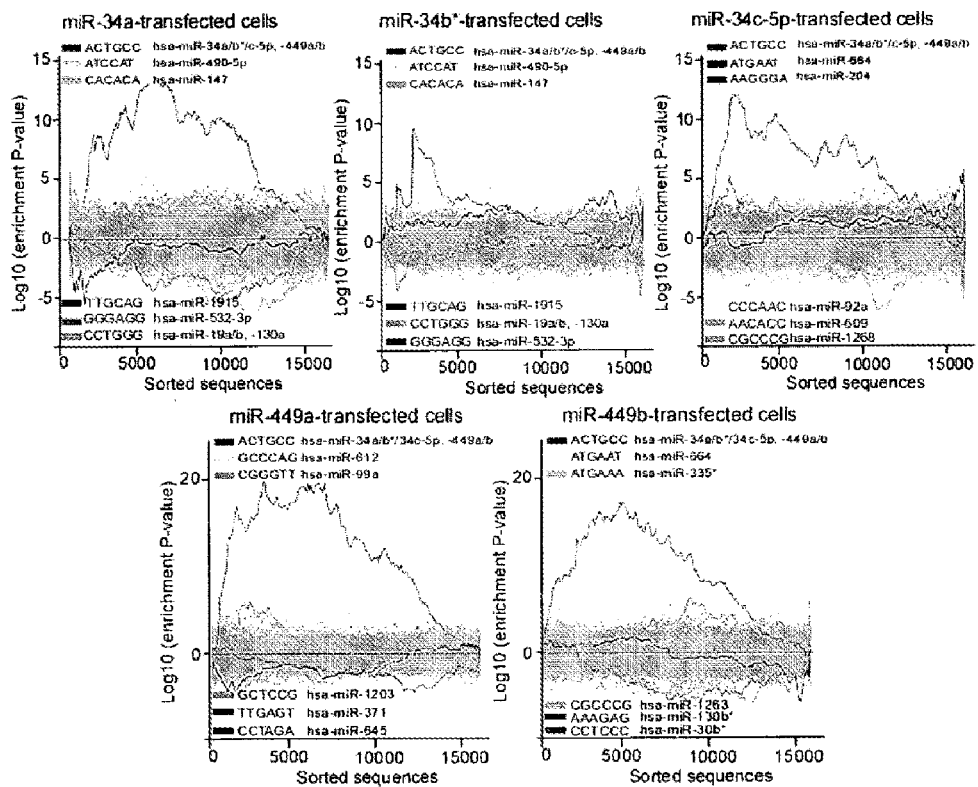

FIG. 12 combines graphs illustrating the enrichment of genes containing the sequence of the recognition sequence ("seed") common to mir-449a, mir-449b, mir-34a, mir-34b* and mir-34c. The number of genes analyzed (about 25000) is shown on the abscissa; these genes are positioned according to their level of repression or expression: the genes are shown from left to right, from the most repressed to the most induced. The ordinate represents the statistical value in log 10 of the level of enrichment (the enrichment score shown on the ordinate corresponds to the absolute value of log 10 of the value P, calculated according to a hypergeometric, binomial cumulative model described by van Dongen S et al. Nat. Methods. 2008 December; 5(12): 1023-5). The miRNA that was transfected into the HAEC cells is indicated on each graph.

Figure 13:
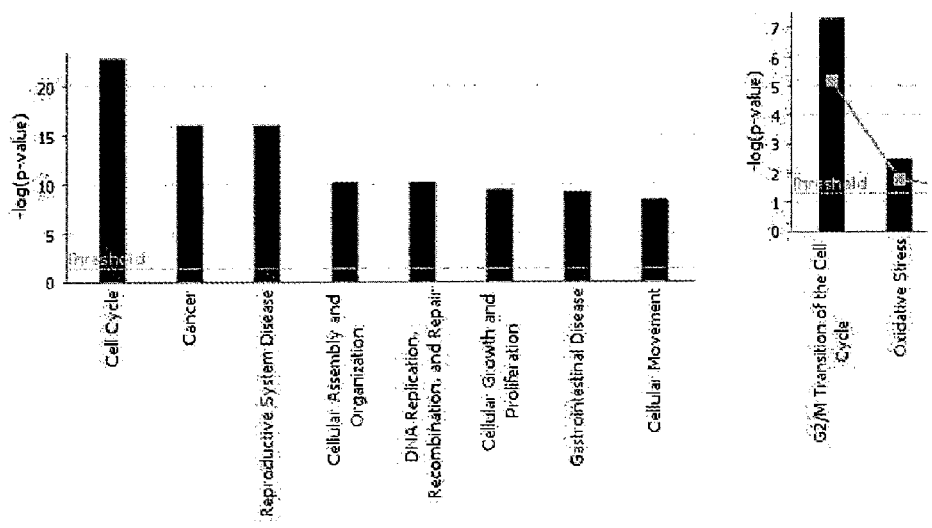

FIG. 13 shows the result of identification, using the IPA software, of biological functions and diseases in relation to the genes that were modulated by expression of the miRNAs according to the invention.

Figure 14:
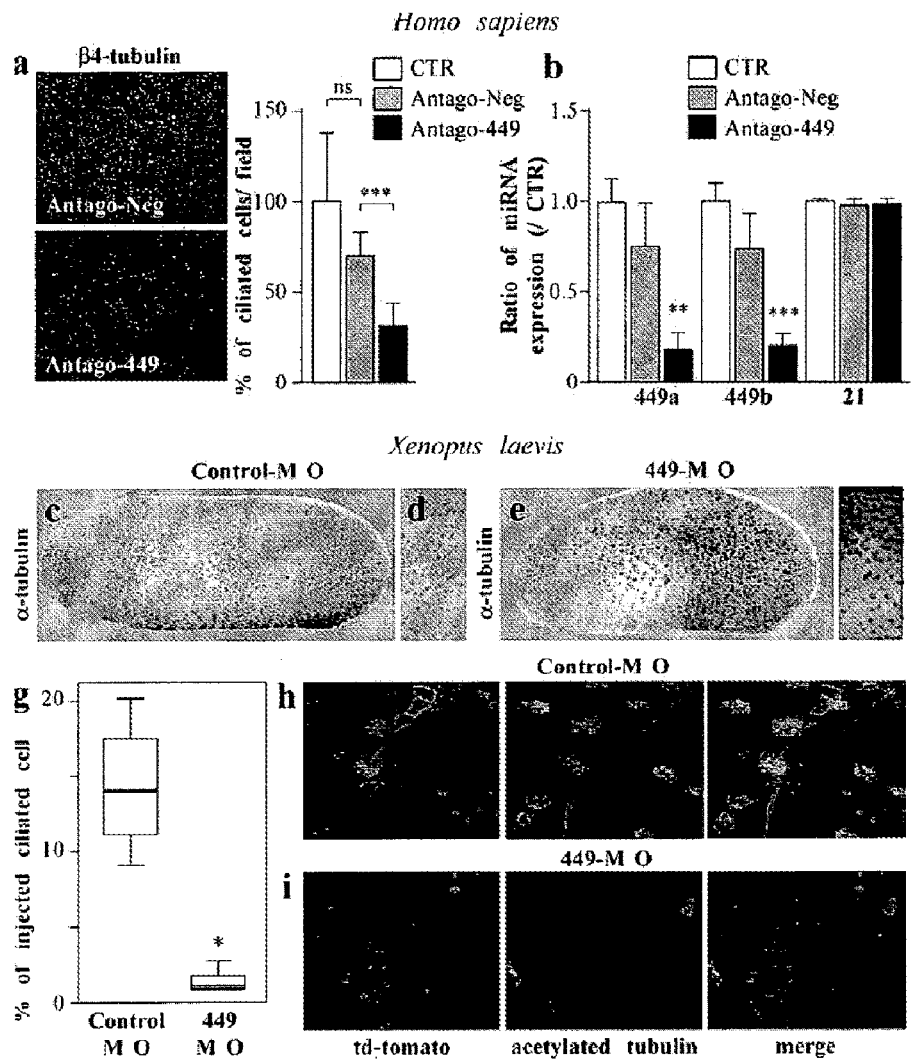

FIG. 14 illustrates the inhibition of ciliogenesis by suppression of the expression of miR-449.

(a,b) the HEAC cells are treated several times with anti-miR-449 antagomirs or a control antagomir (20 nM) during their regeneration (generally 21 days). The percentage of ciliated cells was defined as the ratio of the number of cells positive to +tubulin-β4 relative to the number of nuclei (20 fields/filter and 3 filters/donor). Micrograph (a) shows an immunolabeling typical of HAEC cells treated with a control antagomir (Antago-Neg) or an anti-miR-449 antagomir (Antago-449). The histogram indicates the percentage of ciliated cells per field for each experimental condition (n=6, *, P<0.001, Student test). Micrograph (b) shows that the anti-miR-449 antagomir suppresses the expression of miR449a and miR-449b, but it has no effect on the expression of miR-21 (n=6, ns=not significant, , P<0.01, ***, P<0.001, Student test).

Tests on *Xenopus*: a mixture comprising 30 ng of control morpholino oligonucleotides (MO) (micrographs c, d, h) or of MO miR-449a/b/c (10 ng each) and 2.5 ng of fluorescent lysine-dextran (FLDx, colored orange/brown, micrographs c and f) or 500 pg of mRNA of TD-tomato-CAAX for tracing the cells injected (micrographs g, i) is injected into the epidermis of *Xenopus* embryos at the segmentation stage.

Micrographs e and f permit detection of progenitors of ciliated cells by labeling with tubulin-α with the technique of hybridization in situ.

Micrograph f: region depleted of miR-449 (top) shows an excess of cells positive to tubulin-α relative to the region not injected (bottom). Micrographs h and show the detection of cilia in embryos at the tadpole stage with an anti-acetylated tubulin antibody. The image is obtained in the region of the tail fin. No cilium is detected in the cells co-injected with MO miR-449 and mRNA TD-tomato-CAAX. Graph g shows the percentage of cells injected (positive for red fluorescence TD-tomato) which develop cilia in the control explant (225 cells, 8 tails) and in that modified with MO miR-449 (242 cells, 8 tails, p=0.036, Kruskall-Wallis test).

Figure 15:
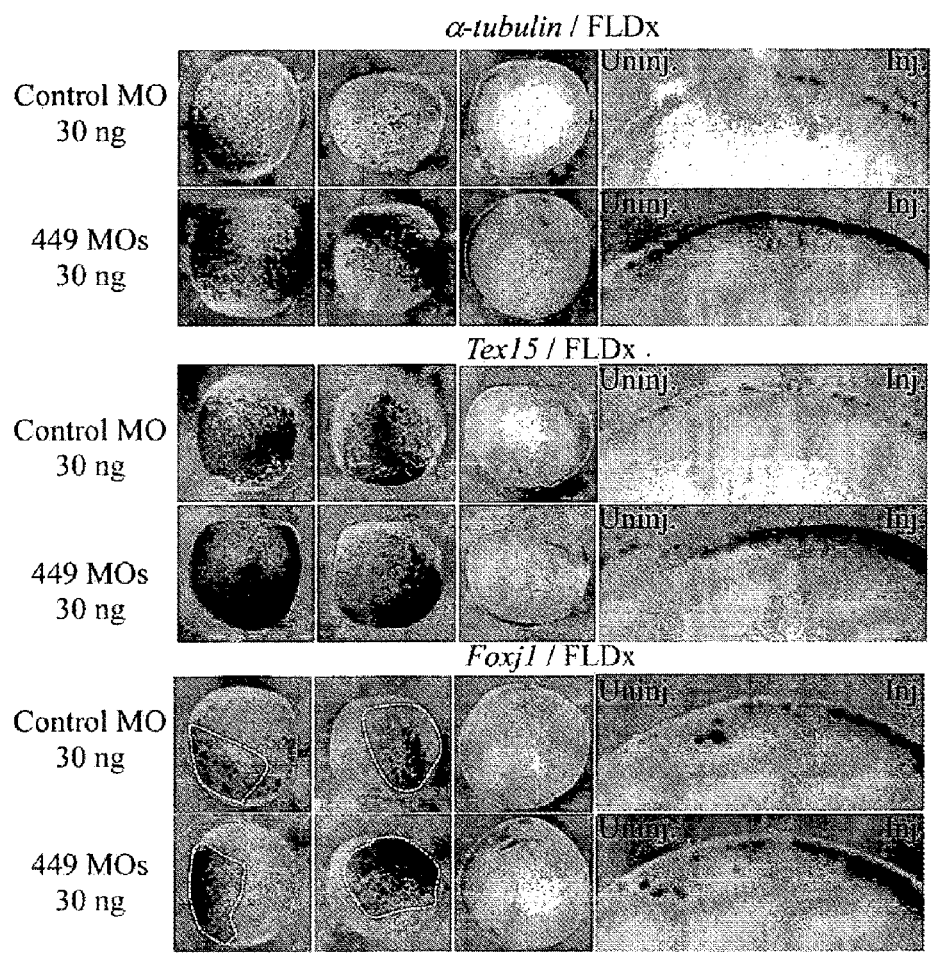

FIG. 15 illustrates the induction of specialization of the ciliated cells by suppression of miR-449. A mixture of MO anti-miR-449 or of control MO and of FLDx is injected in the epidermis of embryos at the segmentation stage. The embryos are fixed at the early neurula stage and then submitted to hybridization in situ with riboprobes of tubulin-α, Tex15 and Foxj1, they are then immunolabeled to reveal the presence of FLDx (fluorescent lysine-dextran). The embryos were then sectioned for better visualization of the density of progenitors of the ciliated cells in the injected areas. For the three markers, suppression of expression of the miR-449s led to an increase in progenitors of the ciliated cells.

Figure 16:
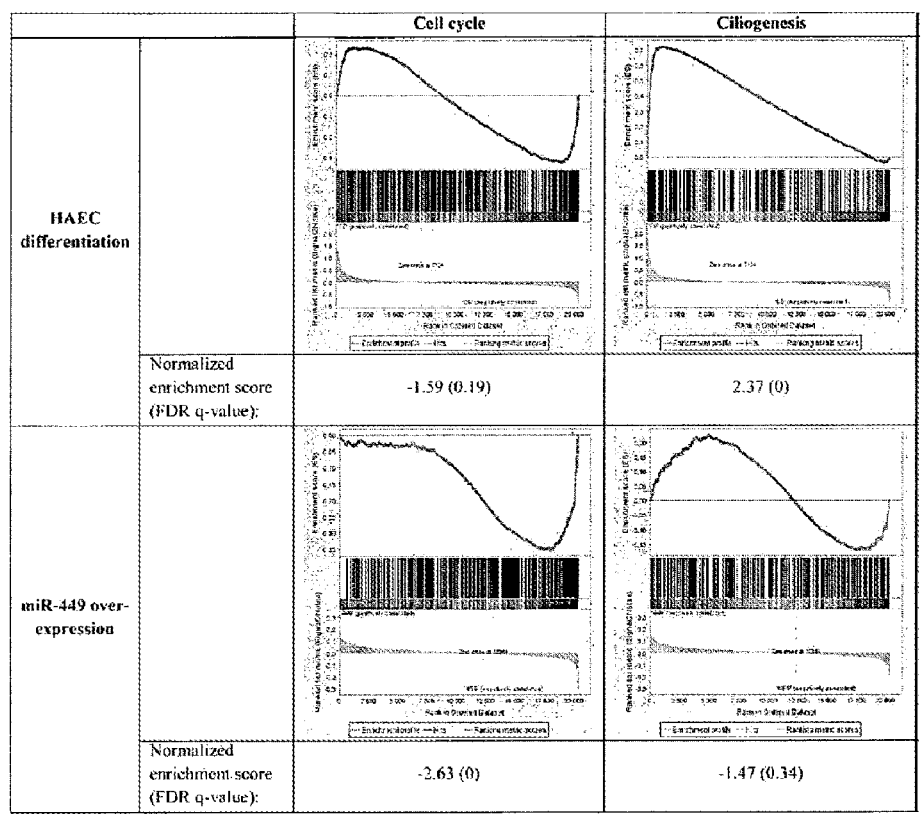

The four sections of FIG. 16 illustrate results of enrichment of the genes as explained on the website http://www.broadinstitute.org/gsea/doc/GSEAUserGuideFrame. html. The GSEA calculates an enrichment score (ES) which reflects the degree to which a gene is overexpressed within a list of given genes. A positive ES indicates enrichment of a gene on the left of the ensemble of genes (corresponding to an over-regulated gene), a negative ES indicates enrichment of a gene on the right of said ensemble of genes (corresponding to an under-regulated gene). For each section, the top panel is a graphical representation of the enrichment score of an ensemble of genes as indicated on the left. The middle part of the panel shows where the members of the ensemble of genes appear in the list ("cell cycle" or "ciliogenesis"). The bottom part of the panel shows the value of metric scheduling which measures the correlation between the expression of a gene and the cellular phenotype; a positive value indicates a correlation with the first phenotype (differentiation or overexpression of the miR-449s) and a negative value indicates a correlation with the second phenotype (not differentiated or control). All these experimental data are stored in the Base Gene Expression Omnibus under accession number GSE22147.

Figure 17:
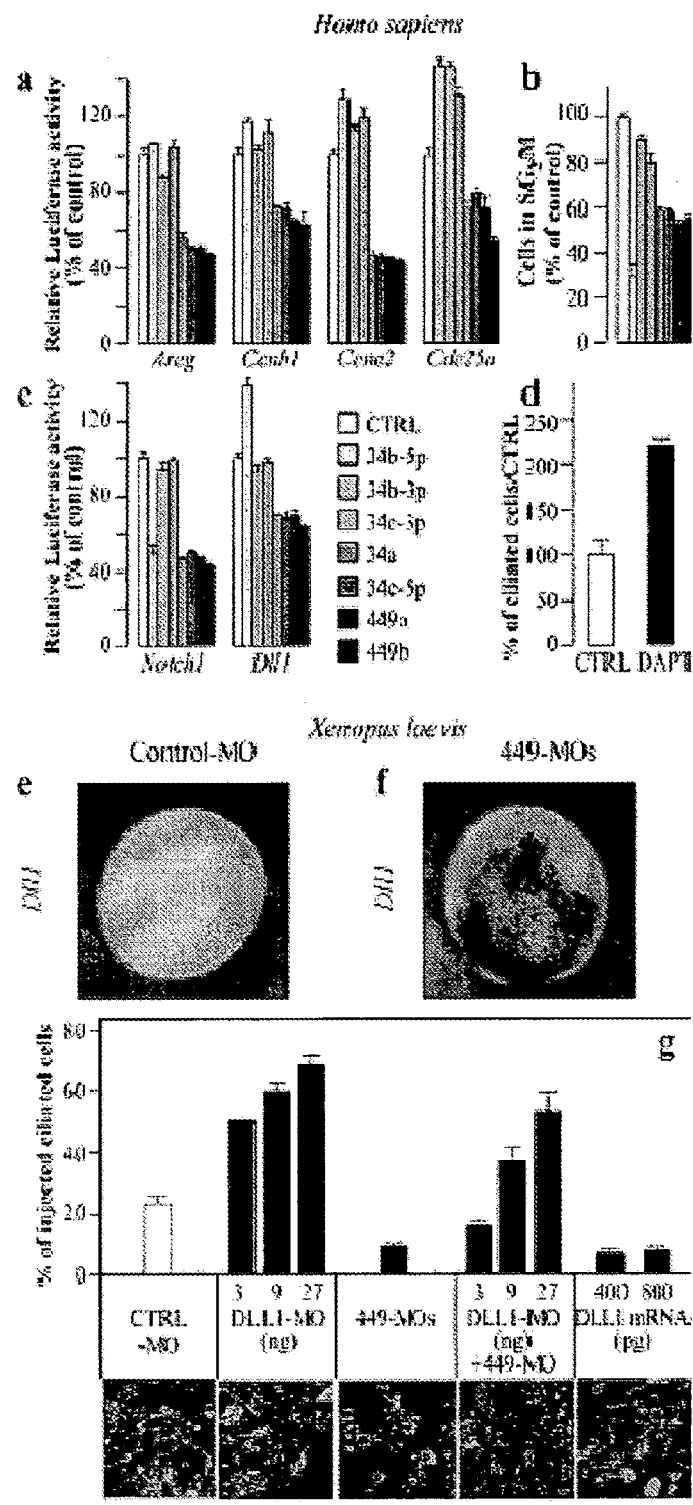

FIG. 17 presents the results showing that miR-449 targets the cell cycle and the Notch pathway.

Cell cycle: graph (a) shows the modulation of the activity of the reporter gene of luciferase fused to the noncoding 3' part of the mRNA of Areg, Ccnb1, Ccne2, Cdc25a by miR-449a/b and miR-34a/c5-p.

Notch signalling pathway: Graph (c) shows the modulation of the activity of the reporter gene of luciferase fused to the noncoding 3' part of the mRNA of DLL1 and Notch 1 by miR-449a/b and miR-34a/c5-p.

All the experiments were carried out at least twice in triplicate. The values were normalized to the internal control of *Renilla* luciferase. The error bars indicate the standard deviation.

Graph (b) shows the blocking of the cell cycle in phase G1 by miR-449 and miR-34.

Graph (d) shows the effect of inhibition of the Notch pathway by DAPT (10 µM) on the ciliogenesis of the HAEC cells.

Micrographs (e) and (f) show embryos at the segmentation stage, where the epidermis received an injection of a mixture of MO anti-miR-449 and of fluorescent lysine-dextran (FLDx).

Staining by hybridization in situ reveals the sustained expression of DLL1 in the epidermis deficient in miR-449.

Panel (g) shows embryos at the segmentation stage, where the epidermis received an injection of control MO, of MO anti-miR-449 and of MO Dll1 or of mRNA DLL1. The cilia were stained with an anti-acetylated tubulin antibody (in red). For each condition, at least 200 cells positive to FLDx (in green), on 6 to 8 tails, have cilia (P<0.03). It should be noted that the injection of mRNA of Dll1 suppresses ciliogenesis, although it increases the number of progenitors of ciliated cells. Extinction of the expression of Dll1 induces ciliogenesis.

DETAILED DESCRIPTION OF THE INVENTION

Examples

I—Preparation of the Biological Cellular Model

I-A. Human Airway Epithelial Cells

The tests were conducted with primary cultures of healthy human airway epithelial cells isolated from nasal conchae or polyps collected from patients undergoing septoplasty, turbinectomy or polypectomy. The cells were then cultivated on a porous substrate covered with type IV collagen (Transwell® clear, polyester, 0.4 µm, Costar) at the air-liquid interface (ALI) for the purpose of inducing differentiation (Puchelle, E et al., 2006). The morphological and physiological characteristics of the airway epithelium were described in detail (Puchelle, E. et al., 2006).

I-A.1. Material and Methods

Patients and Tissue Samples

Inferior conchae or nasal polyps were collected from 3 patients who were to undergo turbinectomies or polypectomies for nasal obstruction or septoplasty (Dr. Castillo, ORL Department, Pasteur Hospital, Nice, France). Patients with asthma, mucoviscidosis or allergies were excluded from the study. All the procedures were approved by the ethical committee of the University of Nice-Sophia-Antipolis.

Isolation and Culture of Healthy Human Airway Epithelial Cells (HAECs)

The primary cultures of healthy HAECs derived from nasal mucosa were conducted by a method adapted from previous studies (Wu et al., 1985; Marcet et al., 2007; LeSimple et al., 2007). After excision, the tissue is immersed immediately in an equilibrated solution of salts (HBSS (without $Ca^{2+}/Mg^{2+}$) Invitrogen) containing HEPES (25 mM, Invitrogen), 100 U/ml penicillin (Gibco, Invitrogen), 100 mg/ml streptomycin (Gibco, Invitrogen), 100 mg/ml of gentamicin sulfate (Gibco, Invitrogen), and 2.5 mg/ml of amphotericin B (Gibco, Invitrogen). After rinsing 3 times with the medium HBSS-HEPES-antibiotics, the tissue is digested with 0.1% of pronase (Sigma) at 4° C., overnight. The tissue is then carefully withdrawn from the digestion medium, and the airway epithelial cells on the surface of the nasal mucosa are detached from the stroma by gentle stirring with the medium HBSS-HEPES-antibiotics containing 10% of fetal calf serum (FCS). The cellular suspension is centrifuged at 150 g, 10 min at 4° C. and the cellular pellet is resuspended in 10% FCS-HBSS-HEPES-antibiotics and centrifuged again. The second cellular pellet is then resuspended in a medium of 10% FCS-antibiotics-Dulbecco's modified Eagle's medium (DMEM, Invitrogen) using a needle (0.8 mm) and a 10-ml syringe for dissociating the cellular aggregates. The cells are then seeded ($10^4/cm^2$) on permeable porous supports (Transwell®, Costar, Sigma) covered with type IV collagen (Sigma) and incubated in a humidified atmosphere at 37° C., 5% $CO_2$. On the next day, the culture medium is replaced with proliferation medium (BEGM) reconstituted using BEBM medium (Lonza) containing the following hormonal supplements and other growth factors: insulin, apotransferrin, epidermal growth factor (EGF), epinephrine, hydroxycortisone, 3,30,5-triiodothyronine, endothelial cell growth supplement, retinoic acid (at low concentration, about 10 nM), amphotericin B (2.5 mg/ml), streptomycin (100 mg/ml), penicillin (100 U/ml), gentamicin sulfate (50 mg/ml) and L-glutamine (2 mM).

Confluence of the monolayer of airway epithelial cells is typically reached after 7 days of culture. The apical surface medium is then withdrawn in order to put the cells at the air-liquid interface and the basolateral medium is replaced with differentiation medium: BEBM/DMEM of ratio (1:1) and containing the same supplements as stated above apart from the retinoic acid, which is added this time at high concentration, about 300 nM, to induce mucociliary differentiation of the airway epithelium. The experiments are then conducted on differentiated cultures having a transepithelial resistance above 500 ohm/$cm^2$.

Immunocytochemical Labeling and Confocal and Electron Microscopy

The sections of membranes from airway cell cultures grown at the air-liquid interface are fixed in acetone or in methanol (10 min, −20° C.). After rinsing in PBS, the non-specific sites are blocked in PBS-BSA 3%, then the primary antibody is incubated in PBS-BSA-1% from 1 h at room temperature to 16 h at 4° C. depending on the antibody used. After rinsing, the coupled secondary antibody, dissolved in PBS-BSA 1%, is incubated for 1 h at room temperature. After rinsing, the nuclei are labeled with DAPI and counterstained with Harris hematoxylin. After rinsing, the slides are mounted and are observed in the confocal microscope. In the case of double sequential labeling involving two mouse antibodies, a step of blocking the free sites of the primary antibodies is performed using anti-mouse anti-Fab (H+L) antibodies for 30 minutes at room temperature.

For electron microscopy, the cells are fixed in monosodium phosphate buffer 0.1 M containing 1.6% of glutaraldehyde.

Sorting of the Airway Epithelial Cells

After dissociation of the stroma of nasal polyps, the epithelial cells (about $20.10^6$) are incubated in PBS-BSA-EDTA for 30 min and then incubated with labeled antibody CD151-PE and anti-TF (tissue factor)-FITC for 20 min, 4° C. (see Hajj, R. et al., Stem Cells 25, 139-148 (2007)). After washing twice, the cells are taken up in PBS-EDTA and incubated with DAPI for labeling the cells whose integrity has been altered.

Cell sorting was carried out on the FACSAria sorter (BD Biosciences) equipped with 3 lasers, blue, red and violet. Dead cells, aggregates and double cells were excluded. The doubly positive population of basal cells (CD151+/FT+) and the negative population of cylindrical cells (containing ciliated cells and mucus-secreting cells) (CD151−/FT−) were selected and sorted at a rate of 5000 events/s (30 MHz frequency). The purity and identity of the sorted cells were then verified by cytometry and immunocytochemistry.

I-A.2. Observation of the Morphology of the Cells Labeled with Hematoxylin and with Eosin Immunolabeling was performed in order to examine the expression of epithelial markers of differentiation (tubulin-β4 for ciliated cells (FIGS. 1E-F), mucin MUC5AC for mucus-secreting cells (FIGS. 1G-H), and cytokeratin 13 for basal cells (FIGS. 1I-J)).

The states of differentiation were evaluated by confocal and electron microscopy. It was decided to study four key times in differentiation:

(1) during the first days of establishment of the air-liquid interface (ALI-D0), the cells proliferate and form a stratified squamous epithelium;

(2) after 5-7 days of air-liquid interface (ALI-D7), cellular polarization begins;

(3) after about 14 days of air-liquid interface, the cells form a pseudostratified epithelium where the first cilia appear on the surface of the cells (ALI-FC), as well as cellular elongation, indicating the start of ciliogenesis (FIG. 1C);

(4) after about 21 days of air-liquid interface (ALI-WD), the airway epithelium becomes pseudostratified, a wholly differentiated stage in which most cells are cylindrical and ciliated, with an underlying layer of basal cells, as well as mucus-secreting cells (FIG. 1D).

After 3-4 weeks of culture, the morphological criteria and the specific markers of differentiation of the 3 cellular types of the surface airway epithelium (i.e. basal (FIGS. 1I-J), secreting (FIGS. 1G-H), and ciliated (FIGS. 1E-F) can be observed.

II—Measurement of Expression of the miRNAs in the Cells Selected During Ciliogenesis The techniques of high-throughput sequencing make it possible to establish the abundance of certain miRNAs in a complex mixture.

Based on the number of specific sequences of a miRNA within an experimental condition, it is possible to evaluate the abundance of said miRNA within all of the miRNAs.

II-1. Material and Methods

Ciliated Epidermal Cells of Embryos of Xenopus laevis

The ciliated epidermis of embryos of Xenopus laevis is used as a model of mucociliary epithelium as described by Hayes et al. (Dev Biol 312 (1), 115 (2007)).

Extraction of Total RNAs and Quality Controls

The total RNAs were extracted from HAECs cultivated at the air-liquid interface at four stages of differentiation: ALI-D0 (0 day), ALI-D7 (7 days), ALI-FC (during appearance of the first cilia at about 14 days) and ALI-WD (wholly differentiated at about 21 days). The cells are lysed in reagent with Trizol® (Invitrogen). The total RNAs containing small RNAs and microRNAs are purified on Qiagen RNEasy columns (Qiagen) according to the supplier's instructions.

The purity and concentration of the samples of total RNAs are first evaluated using the Nanodrop spectrophotometer. The ratios 260/280 (ratio of the values of absorbance at 260 and 280 nm of a sample measured with a spectrophotometer) and 260/230 (ratio of the values of absorbance at 260 and 230 nm of a sample measured with a spectrophotometer); these ratios reflect RNA purity when they are between 1.5 and 2; they are verified and must have a value close to 2.

The total RNAs of embryonic cells of Xenopus were purified with a Qiagen RNeasy kit (Qiagen).

The RNAs are then loaded on an RNAnano chip (Agilent Technologie, France) and their quality (integrity and level of degradation of the RNAs) is analyzed using the Bioanalyzer System (Agilent Technologies, France).

High-Throughput Sequencing of microRNA

The total RNAs containing small RNAs and microRNAs are isolated as before. The procedure is based on the Applied Biosystems Ligase-Enhanced Genome Detection technology (LEGenD™); the SOLiD™ Small RNA Expression kit (Applied Biosystems, France) was used. With this method it is possible to convert the small RNAs of a sample into a library of double-stranded DNA; it was developed by Applied Biosystems SOLiD™ System for a new generation of high-throughput sequencing.

The high-throughput sequencing of the microRNAs was carried out according to the supplier's recommendations. Briefly, the total RNAs containing the small RNAs are hybridized (65° C., 10 min, then at 16° C., 5 min) and ligated (16° C., 2-16 h in a thermocycler) with the Adaptor Mix A for producing a matrix for sequencing the 5' end of the small RNAs, or with the Adaptor Mix B for sequencing the 3' end. The samples are then reverse-transcribed (42° C., 30 min) to synthesize the complementary DNA (cDNA). The library of small RNAs is amplified by PCR and after migration on polyacrylamide gel the amplified small RNAs are cut out and extracted from the gel according to their size (length of about 105-150 bases, according to the supplier's instructions), eluted and resuspended in nuclease-free water. The concentration of nucleic acids is then measured and normalized before proceeding with preparation of the samples for sequencing.

Statistical Analyses of the Data from High-Throughput Sequencing

The statistical analyses are performed using software R from Bioconductor® (Peter Dalgaard, Statistics and computing, Introductory statistics with R. Springer, 2002; R. Gentleman, V. J. Carey, W. Huber, R. A. Irizarry, S. Dudoit. Statistics for biology and health. Bioinformatics and computational biology solutions using R and bioconductor. Springer, 2005).

For each microRNA sequenced, the number of sequences of the 5p strand and of the 3p strand of the microRNA was normalized to $10^6$ sequences and converted to percentage abundance of expression for each of the microRNAs. The data were then normalized according to a linear model and an empirical Bayesian method using software R. For subsequent analyses, only the microRNAs were retained for which the percentage expression (or abundance) is greater than 1% of the total of the microRNAs in at least one culture condition, with a |Log$_2$ Ratio| below 0.5 and an adjusted P-value below 0.05.

Analysis of the microRNAome by microRNA Chips (Agilent Technologies)

In parallel with the high-throughput sequencing of the microRNAs, the repertoire of expression of the microRNAs (microRNAome) is investigated using the technology of Agilent® microRNA chips. For this, RNA samples from the same patients as before were used, labeled and hybridized on Agilent® miRNA chips (Human miRNA Microarray v2, containing 866 human miRNAs and 89 human viral miRNAs, i.e. all the human miRNAs contained and referenced in Sanger miRBase v.12.0, Agilent Technologies, France) using the "miRNA labeling and hybridization" kit, following the supplier's instructions (Agilent Technologies).

Analyses of the Transcriptome by DNA Chips (Affymetrix®)

For the analyses of the transcriptome, the total RNAs are purified and their quality is verified as before.

The analysis is then performed on DNA chips, GeneChip® Human Gene 1.0 ST Array (Affymetrix®). Each of the 28869 genes is represented on the chip by about 26 probes covering the entire length of the gene. The total RNAs are labeled and hybridized using "whole Transcript (WT) Sense Target Labeling and Control Reagents, fluidics and scanning instrumentation and basic analysis software".

Analyses of the Transcriptome Data Obtained by DNA Chips (Affymetrix®)

The data analyses are performed using the software R Bioconductor developed by the statistical consortium R. Then the data are visualized by means of the Mediante interface, an information system developed for large-scale analysis and storage of information obtained during analyses of chips (Le Brigand and Barbry, 2007).

For the Affymetrix® chips, the data are analyzed using the RMA (Robust Multi-Chip Average) algorithm, which performs a correction for background noise, a normalization step, and reporting of the levels of the probes. This method displays high accuracy, particularly for low values of expression, and displays higher specificity and sensitivity than many other known methods (Irizarry et al., 2003). The data are normalized according to a linear model and an empirical Bayesian method using the R Bioconductor software. Graphics in the form of Volcano plots (FIG. 7) are used for showing the quantitative level of regulation of the genes expressed in log 2 as a function of their statistical significance relative to experimental replicas.

Hybridization In Situ

After fixation in 4% paraformaldehyde (Electron Microscopy Sciences), frozen sections of cellular cultures at stage ALI-D21 or of human airway tissues were acetylated, incubated overnight at 55° C. with 0.3 ng/µl of LNA probes labeled with digoxigenin targeting microRNAs (Exiqon, Woburn, Mass.) in deionized formamide 50%, 0.3 M NaCl, 20 mM Tris-HCl pH 8.0, 5 mM EDTA, 10 mM NaPO4 pH 8.0, 10% dextran sulfate, 1× of Denhardt solution, and 0.5 mg/ml of yeast RNA.

The sequences of the probes are:

for miR-449: ccagctaacaatacactgcc (SEQ. ID. No. 204)

for miR-31: agctatgccagcatcttgcct (SEQ. ID. No. 205) for the negative control microRNA ("scramble"): gtgtaacacgtctatacgccca (SEQ. ID. No. 206).

The probes were detected by sequential incubations with peroxidase conjugated with anti-digoxigenin antibodies (Roche) with the signal amplification kit "Tyramide Signal Aplificatin Plus DNP ASystem" (Perkin Elmer) on the BCIP/NBT substrate (DakoCytomation).

Some slides were then exposed to anti-MUC5AC mouse antibodies and detected with the "LSAB2 System-HRP" kit (Dako). The sections were counterlabeled with the eosin/saffron dye "Nuclear Fast Red", and mounted using the Eukitt mounting medium (Electron Microscopy Sciences).

In *Xenopus*, eggs obtained from NASCO females are fertilized in vitro, cultivated and injected as described by Marchal, L et al. (*Proc Natl Acad Sci USA* 106 (41), 17437 (2009)). The cRNAs of DII1 and of centrin-2-GFP are prepared with the "Ambion mMessage Machine" kit. The membrane-bound vector Td-tomato-CAAX (donated by Chenbei Chang) is linearized with AseI and the cRNA is synthesized with Sp6 polymerase. The fluorescent lysine-dextran (FLDx, 2.5 ng/cell) is co-injected with the morpholino (MO) oligonucleotides for labeling the live embryos and an anti-fluorescein immunodetection is performed for monitoring the distribution of the MOs in the embryos. All the injections are duplicated.

An anti-miR-449a LNA probe labeled with mono-digoxigenin (Exiqon) was used for the hybridization in situ which was performed as described by Kloosterman et al. (*Nat Methods* 3 (1), 27 (2006)). Antisense ribosomal probes of tubulin-α, DII1, Tex15 and Foxj1 were prepared as described by: Deblandre et al. (*Development* 126 (21), 4715 (1999)) for tubulin-α and DII1; Hayes et al. (*Dev Biol* 312 (1), 115 (2007)) for Tex15 and Pohl et al. (*Dev Genes Evol* 214 (4), 200 (2004)) for Foxj1.

II-2. Expression of the miRNAs in the Selected Cells

II-2.A. HAEC Cells

For all the human miRNAs currently known (about 750), the inventors thus found firstly by means of the technique of high-throughput sequencing (HTS) of miRNAs that 115 miRNAs were expressed during differentiation with an intensity value above 8 (corresponding to the Log 2 of the normalized number of miRNAs sequenced).

Using the sequencing technique, it is possible to determine the percentage abundance of each of the miRNAs sequenced. The inventors were thus able to establish, surprisingly, that 26 miRNAs were present in the different stages of differentiation of the human airway epithelium with an abundance above 1% (shown in FIG. 2 and in Table IIIA given below).

The 26 miRNAs identified cover just by themselves of the order of 80% of all the miRNAs expressed in the human airway epithelium; this quantity shows that they are involved in the process of regeneration and/or differentiation of the airway epithelial tissue.

A more detailed analysis of these 26 miRNAs shows that 22 are significantly regulated in at least one of the four stages of differentiation of the human airway epithelium and represent about 70% of the total of the miRNAs: 13 miRNAs are overexpressed whereas 9 miRNAs are repressed (see FIG. 2B and Table IV below).

The value of modulation (also denoted as the ratio of the level of intensity of expression in log 2 at two stages of differentiation) is calculated as the difference between the levels of intensity of expression in log 2 at the two stages of differentiation indicated at the top of each column.

TABLE IIIA

MiRNAs significantly expressed in human airway epithelium and with an abundance greater than 1% in at least one stage of differentiation, identified by high-throughput sequencing (HTS) of miRNA.

| Name | Pre-mir | strands | Level of intensity of expression in log2 | | | | Abundance (%) | | | | Modulation (ratio of the level of intensity of expression in log2 in two stages of differentiation) | | | |
|---|---|---|---|---|---|---|---|---|---|---|---|---|---|---|
| | | | D0 | D7 | FC | WD | D0 | D7 | FC | WD | D7 – D0 | FC – D7 | WD – FC | WD – D0 |
| hsa-miR-449a | hsa-mir-449a | 5p | 4.48 | 9.69 | 14.90 | 15.11 | 0.00 | 0.18 | 6.49 | 5.70 | 5.21 | 5.21 | 0.21 | 10.63 |
| hsa-miR-449b | hsa-mir-449b | 5p | 3.64 | 6.96 | 12.36 | 12.24 | 0.00 | 0.03 | 1.12 | 0.78 | 3.32 | 5.40 | −0.12 | 8.60 |
| hsa-miR-449b* | hsa-mir-449b | 3p | 6.40 | 10.23 | 13.59 | 13.84 | 0.02 | 0.26 | 2.62 | 2.37 | 3.83 | 3.36 | 0.26 | 7.45 |
| hsa-miR-449c | hsa-mir-449c | | 1.54 | 4.13 | 11.57 | 10.98 | 0.00 | 0.00 | 0.32 | 0.20 | 2.59 | 7.44 | −0.59 | 9.44 |
| hsa-miR-34b | hsa-mir-34b | 3p | 7.01 | 8.26 | 12.43 | 13.75 | 0.03 | 0.07 | 1.17 | 2.22 | 1.25 | 4.17 | 1.32 | 6.74 |
| hsa-miR-34c-5p | hsa-mir-34c | 5p | 7.88 | 9.21 | 13.23 | 14.29 | 0.05 | 0.13 | 2.05 | 3.23 | 1.33 | 4.02 | 1.06 | 6.41 |
| hsa-miR-92b | hsa-mir-92b | 3p | 7.49 | 8.70 | 12.82 | 13.42 | 0.04 | 0.09 | 1.54 | 1.77 | 1.21 | 4.12 | 0.60 | 5.93 |
| hsa-miR-1975 | hsa-mir-1975 | 3p | 11.08 | 13.22 | 13.55 | 14.01 | 0.48 | 2.09 | 2.56 | 2.67 | 2.13 | 0.34 | 0.46 | 2.93 |
| hsa-miR-99a | hsa-mir-99a | 5p | 9.77 | 11.19 | 11.96 | 12.65 | 0.19 | 0.52 | 0.85 | 1.03 | 1.43 | 0.77 | 0.69 | 2.88 |
| hsa-miR-191 | hsa-mir-191 | 5p | 14.67 | 15.57 | 16.40 | 16.82 | 5.71 | 10.68 | 18.46 | 18.69 | 0.90 | 0.84 | 0.42 | 2.15 |
| hsa-miR-378 | hsa-mir-378 | 3p | 10.37 | 12.53 | 12.26 | 11.87 | 0.29 | 1.30 | 1.04 | 0.61 | 2.15 | −0.26 | −0.39 | 1.50 |
| hsa-miR-23b | hsa-mir-23b | 3p | 14.06 | 15.35 | 15.18 | 15.35 | 3.73 | 9.19 | 7.92 | 6.72 | 1.30 | −0.17 | 0.16 | 1.29 |
| hsa-miR-125a-5p | hsa-mir-125a | 5p | 12.92 | 13.55 | 13.29 | 14.08 | 1.69 | 2.64 | 2.13 | 2.79 | 0.64 | −0.27 | 0.79 | 1.16 |
| hsa-miR-203 | hsa-mir-203 | 3p | 13.49 | 13.60 | 13.39 | 14.57 | 2.53 | 2.73 | 2.29 | 3.92 | 0.11 | −0.21 | 1.18 | 1.08 |
| hsa-miR-574-3p | hsa-mir-574 | 3p | 13.64 | 14.12 | 14.24 | 14.56 | 2.80 | 3.92 | 4.12 | 3.90 | 0.48 | 0.12 | 0.32 | 0.92 |
| hsa-miR-29c | hsa-mir-29c | 3p | 13.66 | 14.48 | 14.50 | 14.53 | 2.84 | 5.03 | 4.95 | 3.82 | 0.82 | 0.02 | 0.03 | 0.87 |
| hsa-miR-140-3p | hsa-mir-140 | 3p | 12.39 | 12.72 | 13.08 | 13.12 | 1.17 | 1.48 | 1.85 | 1.44 | 0.33 | 0.37 | 0.04 | 0.73 |
| hsa-miR-205 | hsa-mir-205 | 5p | 14.61 | 15.23 | 14.11 | 14.55 | 5.48 | 8.43 | 3.76 | 3.87 | 0.62 | −1.12 | 0.44 | −0.06 |
| hsa-miR-23a | hsa-mir-23a | 3p | 14.42 | 14.47 | 13.67 | 14.10 | 4.79 | 4.99 | 2.77 | 2.83 | 0.06 | −0.80 | 0.43 | −0.31 |
| hsa-miR-31 | hsa-mir-31 | 5p | 13.69 | 13.31 | 12.40 | 12.74 | 2.89 | 2.24 | 1.15 | 1.10 | −0.37 | −0.91 | 0.34 | −0.95 |
| hsa-miR-21 | hsa-mir-21 | 5p | 16.40 | 15.66 | 14.50 | 15.24 | 19.01 | 11.41 | 4.94 | 6.26 | −0.74 | −1.16 | 0.74 | −1.16 |
| hsa-miR-17 | hsa-mir-17 | 5p | 12.85 | 12.68 | 11.81 | 11.61 | 1.61 | 1.44 | 0.76 | 0.50 | −0.17 | −0.87 | −0.20 | −1.24 |
| hsa-miR-29a | hsa-mir-29a | 3p | 16.24 | 14.90 | 14.79 | 14.81 | 17.01 | 6.72 | 6.02 | 4.64 | −1.34 | −0.11 | 0.02 | −1.43 |
| hsa-miR-193b | hsa-mir-193b | 3p | 13.26 | 12.09 | 11.19 | 11.67 | 2.16 | 0.96 | 0.50 | 0.52 | −1.17 | −0.90 | 0.48 | −1.60 |
| hsa-miR-31* | hsa-mir-31 | 3p | 13.56 | 12.91 | 11.60 | 11.83 | 2.64 | 1.69 | 0.66 | 0.59 | −0.65 | −1.31 | 0.24 | −1.73 |
| hsa-miR-210 | hsa-mir-210 | 3p | 12.29 | 11.33 | 10.60 | 10.49 | 1.10 | 0.57 | 0.33 | 0.23 | −0.96 | −0.74 | −0.10 | −1.80 |
| hsa-miR-130a | hsa-mir-130a | 3p | 13.91 | 12.51 | 12.71 | 11.98 | 3.38 | 1.28 | 1.42 | 0.65 | −1.40 | 0.19 | −0.73 | −1.94 |

TABLE IV

MiRNAs significantly expressed and modulated during differentiation of the airway epithelium, with an abundance greater than 1% identified by high-throughput sequencing (HTS) of miRNA.

| Name | Pre-mir | strands | Level of intensity of expression in log2 | | | | Abundance (%) | | | | Modulation (ratio of the level of intensity of expression in log2 in two stages of differentiation) | | | |
|---|---|---|---|---|---|---|---|---|---|---|---|---|---|---|
| | | | D0 | D7 | FC | WD | D0 | D7 | FC | WD | D7 − D0 | FC − D7 | WD − FC | WD − D0 |
| hsa-miR-449a | hsa-mir-449a | 5p | 4.48 | 9.69 | 14.90 | 15.11 | 0.00 | 0.18 | 6.49 | 5.70 | 5.21 | 5.21 | 0.21 | 10.63 |
| hsa-miR-449b | hsa-mir-449b | 5p | 3.64 | 6.96 | 12.36 | 12.24 | 0.00 | 0.03 | 1.12 | 0.78 | 3.32 | 5.40 | −0.12 | 8.60 |
| hsa-miR-449b* | hsa-mir-449b | 3p | 6.40 | 10.23 | 13.59 | 13.84 | 0.02 | 0.26 | 2.62 | 2.37 | 3.83 | 3.36 | 0.26 | 7.45 |
| hsa-miR-449c | hsa-mir-449c | | 1.54 | 4.13 | 11.57 | 10.98 | 0.00 | 0.00 | 0.32 | 0.20 | 2.59 | 7.44 | −0.59 | 9.44 |
| hsa-miR-34b | hsa-mir-34b | 3p | 7.01 | 8.26 | 12.43 | 13.75 | 0.03 | 0.07 | 1.17 | 2.22 | 1.25 | 4.17 | 1.32 | 6.74 |
| hsa-miR-34c-5p | hsa-mir-34c | 5p | 7.88 | 9.21 | 13.23 | 14.29 | 0.05 | 0.13 | 2.05 | 3.23 | 1.33 | 4.02 | 1.06 | 6.41 |
| hsa-miR-92b | hsa-mir-92b | 3p | 7.49 | 8.70 | 12.82 | 13.42 | 0.04 | 0.09 | 1.54 | 1.77 | 1.21 | 4.12 | 0.60 | 5.93 |
| hsa-miR-1975 | hsa-mir-1975 | 3p | 11.08 | 13.22 | 13.55 | 14.01 | 0.48 | 2.09 | 2.56 | 2.67 | 2.13 | 0.34 | 0.46 | 2.93 |
| hsa-miR-99a | hsa-mir-99a | 5p | 9.77 | 11.19 | 11.96 | 12.65 | 0.19 | 0.52 | 0.85 | 1.03 | 1.43 | 0.77 | 0.69 | 2.88 |
| hsa-miR-191 | hsa-mir-191 | 5p | 14.67 | 15.57 | 16.40 | 16.82 | 5.71 | 10.68 | 18.46 | 18.69 | 0.90 | 0.84 | 0.42 | 2.15 |
| hsa-miR-378 | hsa-mir-378 | 3p | 10.37 | 12.53 | 12.26 | 11.87 | 0.29 | 1.30 | 1.04 | 0.61 | 2.15 | −0.26 | −0.39 | 1.50 |
| hsa-miR-23b | hsa-mir-23b | 3p | 14.06 | 15.35 | 15.18 | 15.35 | 3.73 | 9.19 | 7.92 | 6.72 | 1.30 | −0.17 | 0.16 | 1.29 |
| hsa-miR-125a-5p | hsa-mir-125a | 5p | 12.92 | 13.55 | 13.29 | 14.08 | 1.69 | 2.64 | 2.13 | 2.79 | 0.64 | −0.27 | 0.79 | 1.16 |
| hsa-miR-203 | hsa-mir-203 | 3p | 13.49 | 13.60 | 13.39 | 14.57 | 2.53 | 2.73 | 2.29 | 3.92 | 0.11 | −0.21 | 1.18 | 1.08 |
| hsa-miR-205 | hsa-mir-205 | 5p | 14.61 | 15.23 | 14.11 | 14.55 | 5.48 | 8.43 | 3.76 | 3.87 | 0.62 | −1.12 | 0.44 | −0.06 |
| hsa-miR-31 | hsa-mir-31 | 5p | 13.69 | 13.31 | 12.40 | 12.74 | 2.89 | 2.24 | 1.15 | 1.10 | −0.37 | −0.91 | 0.34 | −0.95 |
| hsa-miR-21 | hsa-mir-21 | 5p | 16.40 | 15.66 | 14.50 | 15.24 | 19.01 | 11.41 | 4.94 | 6.26 | −0.74 | −1.16 | 0.74 | −1.16 |
| hsa-miR-17 | hsa-mir-17 | 5p | 12.85 | 12.68 | 11.81 | 11.61 | 1.61 | 1.44 | 0.76 | 0.50 | −0.17 | −0.87 | −0.20 | −1.24 |
| hsa-miR-29a | hsa-mir-29a | 3p | 16.24 | 14.90 | 14.79 | 14.81 | 17.01 | 6.72 | 6.02 | 4.64 | −1.34 | −0.11 | 0.02 | −1.43 |
| hsa-miR-193b | hsa-mir-193b | 3p | 13.26 | 12.09 | 11.19 | 11.67 | 2.16 | 0.96 | 0.50 | 0.52 | −1.17 | −0.90 | 0.48 | −1.60 |
| hsa-miR-31* | hsa-mir-31 | 3p | 13.56 | 12.91 | 11.60 | 11.83 | 2.64 | 1.69 | 0.66 | 0.59 | −0.65 | −1.31 | 0.24 | −1.73 |
| hsa-miR-210 | hsa-mir-210 | 3p | 12.29 | 11.33 | 10.60 | 10.49 | 1.10 | 0.57 | 0.33 | 0.23 | −0.96 | −0.74 | −0.10 | −1.80 |
| hsa-miR-130a | hsa-mir-130a | 3p | 13.91 | 12.51 | 12.71 | 11.98 | 3.38 | 1.28 | 1.42 | 0.65 | −1.40 | 0.19 | −0.73 | −1.94 |

The inventors then used the Agilent miRNA chips to investigate the repertoire of expression of the miRNAs of the human airway epithelium and compare the results obtained in high-throughput sequencing with those obtained with Agilent® commercial miRNA chips. Using this technique, 48 miRNAs were found to be significantly expressed and modulated (Log 2 of the level of intensity of expression>8; $1 < \log_2$ (ratio)<−1 and an adjusted P value<0.05) in at least one of the four stages of differentiation (see FIG. 3 and Table V).

TABLE V miRNAs significantly expressed and modulated during differentiation of the airway epithelium identified by Agilent® miRNA chips

| Name | Level of intensity of expression in log2 | | | | Modulation (ratio of the level of intensity of expression in log2 at two stages of differentiation) | | | |
|---|---|---|---|---|---|---|---|---|
| | D0 | D7 | FC | WD | D7 − D0 | FC − D7 | WD − FC | WD − D0 |
| hsa-miR-449a | 1.47 | 8.00 | 13.70 | 13.54 | 6.53 | 5.70 | −0.15 | 12.08 |
| hsa-miR-449b | 0.47 | 3.08 | 9.33 | 9.11 | 2.61 | 6.25 | −0.22 | 8.64 |
| hsa-miR-34b | 0.77 | 3.65 | 8.13 | 8.94 | 2.88 | 4.48 | 0.81 | 8.17 |
| hsa-miR-34c-5p | 3.94 | 6.29 | 10.56 | 11.39 | 2.35 | 4.27 | 0.82 | 7.44 |

TABLE V-continued miRNAs significantly expressed and modulated
during differentiation of the airway epithelium
identified by Agilent ® miRNA chips

| Name | Level of intensity of expression in log2 | | | | Modulation (ratio of the level of intensity of expression in log2 at two stages of differentiation) | | | |
|---|---|---|---|---|---|---|---|---|
| | D0 | D7 | FC | WD | D7 – D0 | FC – D7 | WD – FC | WD – D0 |
| hsa-miR-34b* | 5.96 | 7.98 | 11.35 | 12.44 | 2.02 | 3.36 | 1.10 | 6.48 |
| hsa-miR-99a | 5.02 | 7.35 | 8.12 | 8.31 | 2.33 | 0.77 | 0.19 | 3.28 |
| hsa-miR-30b | 7.62 | 9.98 | 10.03 | 10.17 | 2.36 | 0.05 | 0.15 | 2.55 |
| hsa-miR-768-3p | 7.43 | 9.51 | 9.81 | 9.96 | 2.08 | 0.30 | 0.14 | 2.53 |
| hsa-miR-30e | 6.73 | 9.50 | 9.25 | 9.12 | 2.76 | −0.25 | −0.13 | 2.38 |
| hsa-miR-200a | 8.64 | 10.58 | 10.79 | 10.84 | 1.94 | 0.20 | 0.06 | 2.20 |
| hsa-miR-26a | 8.50 | 10.70 | 10.59 | 10.65 | 2.20 | −0.11 | 0.06 | 2.15 |
| hsa-miR-200b | 9.93 | 11.94 | 11.87 | 12.04 | 2.01 | −0.07 | 0.17 | 2.11 |
| hsa-miR-429 | 7.97 | 9.68 | 9.82 | 9.93 | 1.71 | 0.14 | 0.10 | 1.95 |
| hsa-miR-34a | 8.58 | 10.89 | 10.35 | 10.49 | 2.31 | −0.54 | 0.13 | 1.91 |
| hsa-miR-141 | 11.15 | 13.31 | 13.03 | 13.03 | 2.16 | −0.28 | 0.00 | 1.88 |
| hsa-miR-15a | 7.74 | 10.10 | 9.71 | 9.61 | 2.36 | −0.39 | −0.10 | 1.87 |
| hsa-miR-30d | 7.06 | 8.94 | 8.88 | 8.92 | 1.88 | −0.06 | 0.05 | 1.86 |
| hsa-miR-23b | 8.92 | 10.88 | 10.61 | 10.64 | 1.96 | −0.27 | 0.04 | 1.72 |
| hsa-miR-224 | 6.84 | 9.40 | 8.52 | 8.52 | 2.55 | −0.87 | 0.00 | 1.68 |
| hsa-miR-26b | 7.97 | 9.91 | 9.54 | 9.62 | 1.94 | −0.37 | 0.08 | 1.65 |
| hsa-miR-148a | 7.35 | 9.41 | 8.91 | 8.95 | 2.06 | −0.50 | 0.04 | 1.60 |
| hsa-miR-16 | 9.47 | 11.54 | 11.18 | 11.06 | 2.07 | −0.36 | −0.11 | 1.59 |
| hsa-miR-29c | 9.04 | 10.66 | 10.38 | 10.62 | 1.61 | −0.28 | 0.24 | 1.57 |
| hsa-miR-425 | 6.61 | 8.21 | 8.39 | 8.18 | 1.59 | 0.19 | −0.21 | 1.57 |
| hsa-miR-30c | 7.80 | 9.77 | 9.43 | 9.31 | 1.97 | −0.34 | −0.12 | 1.51 |
| hsa-let-7g | 9.30 | 11.12 | 10.59 | 10.80 | 1.83 | −0.54 | 0.21 | 1.50 |
| hsa-miR-151-5p | 6.71 | 8.54 | 8.17 | 8.17 | 1.83 | −0.37 | 0.00 | 1.46 |
| hsa-miR-200c | 10.20 | 12.01 | 11.54 | 11.64 | 1.82 | −0.47 | 0.09 | 1.44 |
| hsa-miR-27b | 9.26 | 11.03 | 10.57 | 10.62 | 1.77 | −0.47 | 0.05 | 1.36 |
| hsa-let-7f | 11.11 | 12.75 | 12.01 | 12.19 | 1.63 | −0.73 | 0.17 | 1.08 |
| hsa-let-7c | 9.10 | 10.71 | 10.00 | 10.15 | 1.61 | −0.71 | 0.14 | 1.05 |
| hsa-let-7a | 11.54 | 13.16 | 12.47 | 12.55 | 1.62 | −0.69 | 0.08 | 1.01 |
| hsa-let-7b | 11.00 | 12.66 | 11.89 | 11.96 | 1.67 | −0.77 | 0.07 | 0.97 |
| hsa-let-7e | 8.53 | 9.91 | 9.34 | 9.48 | 1.38 | −0.57 | 0.15 | 0.95 |
| hsa-miR-21 | 14.27 | 15.83 | 15.15 | 15.20 | 1.56 | −0.69 | 0.06 | 0.93 |
| hsa-miR-374a | 7.04 | 8.45 | 7.91 | 7.83 | 1.41 | −0.54 | −0.08 | 0.79 |
| hsa-miR-125a-5p | 7.37 | 8.66 | 8.20 | 8.15 | 1.29 | −0.46 | −0.04 | 0.79 |
| hsa-miR-939 | 6.64 | 8.04 | 7.41 | 7.34 | 1.40 | −0.63 | −0.07 | 0.70 |
| hsa-miR-106b | 8.08 | 9.47 | 8.94 | 8.77 | 1.39 | −0.53 | −0.18 | 0.69 |
| hsa-miR-25 | 7.15 | 8.50 | 7.85 | 7.80 | 1.35 | −0.65 | −0.05 | 0.66 |
| hsa-miR-96 | 8.52 | 9.71 | 9.21 | 9.16 | 1.19 | −0.50 | −0.04 | 0.64 |
| hsa-miR-22 | 10.67 | 11.75 | 11.10 | 11.15 | 1.09 | −0.66 | 0.05 | 0.48 |
| hsa-miR-181a | 7.05 | 8.47 | 7.62 | 7.25 | 1.41 | −0.84 | −0.37 | 0.20 |
| hsa-miR-21* | 7.28 | 8.49 | 7.75 | 7.46 | 1.21 | −0.74 | −0.29 | 0.18 |
| hsa-miR-365 | 8.44 | 8.41 | 7.21 | 7.25 | −0.02 | −1.21 | 0.05 | −1.18 |
| hsa-miR-130a | 8.83 | 9.48 | 7.95 | 7.52 | 0.65 | −1.53 | −0.43 | −1.31 |
| hsa-miR-100 | 8.00 | 7.55 | 6.29 | 6.52 | −0.46 | −1.25 | 0.22 | −1.49 |
| hsa-miR-193b | 8.62 | 7.95 | 6.76 | 6.69 | −0.67 | −1.19 | −0.07 | −1.93 |

On comparing the miRNAs that are found to be significantly modulated and expressed in at least one condition of cellular culture in high-throughput sequencing of miRNAs (HTS) or in Agilent® miRNA chips, a strong correlation is obtained between the results obtained with the two techniques, with a correlation coefficient r=0.9106 (see FIG. 4).

To summarize, 26 miRNAs were detected and selected in HTS in at least one of the culture conditions (with an abundance of expression above 1%) and 48 miRNAs on Agilent® miRNA chips (with a level of intensity of expression in log 2 above 8). Counting the common miRNAs obtained by the two techniques, this means 61 separate miRNAs significantly expressed in at least one of the conditions of differentiation of the epithelium (60 are shown in Table VI, to which hsa-miR-1975 must be added, see Table III).

The 22 miRNAs identified as significantly regulated and sufficiently abundant in HTS are also found to be modulated on Agilent® miRNA chips with varying significance and with various levels of intensity.

As described above, the miRNAs are synthesized in the form of precursors having a hairpin structure and then undergo a final maturation by the enzyme Dicer to give two small single-stranded RNAs (5p and 3p) of which one of the two strands called mature will interact with the RISC complex and exert its modulating function whereas the other complementary strand called star (designated mir-xy*) will be degraded. Accordingly, the inventors measured the two strands of each of the miRNAs systematically by means of the various techniques used (miRNA chips, sequencing, PCR). The inventors observed that for some of the miRNAs selected, the two strands (5p and 3p) are modulated, but only one of the two strands for a given selected miRNA is found to be expressed more abundantly.

TABLE VI

Comparison of the miRNAs modulated and expressed between Agilent ® miRNA chips and HTS

| Name | Modulation (ratio of the level of intensity of expression in log2 in two stages of differentiation) measured with the Agilent chips | | | | Modulation (ratio of the level of intensity of expression in log2 in two stages of differentiation) measured by high-throughput sequencing | | | | Level of intensity of expression in log2 measured with the Agilent chips | | | | Level of intensity of expression in log2 measured by high-throughput sequencing | | | |
|---|---|---|---|---|---|---|---|---|---|---|---|---|---|---|---|---|
| | D7 − D0 | FC − D7 | WD − FC | WD − D0 | D7 − D0 | FC − D7 | WD − FC | WD − D0 | D0 | D7 | FC | WD | D0 | D7 | FC | WD |
| hsa-let-7a | 1.62 | −0.69 | 0.08 | 1.01 | −0.64 | 0.28 | 0.88 | 0.51 | 11.54 | 13.16 | 12.47 | 12.55 | 3.80 | 3.16 | 3.43 | 4.31 |
| hsa-let-7b | 1.67 | −0.77 | 0.07 | 0.97 | −0.57 | −0.03 | 0.66 | 0.05 | 11.00 | 12.66 | 11.89 | 11.96 | 11.23 | 10.65 | 10.62 | 11.28 |
| hsa-let-7c | 1.61 | −0.71 | 0.14 | 1.05 | 0.14 | 0.21 | 0.55 | 0.90 | 9.10 | 10.71 | 10.00 | 10.15 | 6.96 | 7.10 | 7.31 | 7.86 |
| hsa-let-7e | 1.38 | −0.57 | 0.15 | 0.95 | 0.38 | −0.27 | 0.07 | 0.18 | 8.53 | 9.91 | 9.34 | 9.48 | 7.42 | 7.80 | 7.53 | 7.60 |
| hsa-let-7f | 1.63 | −0.73 | 0.17 | 1.08 | 0.22 | −0.56 | 0.45 | 0.11 | 11.11 | 12.75 | 12.01 | 12.19 | 5.24 | 5.46 | 4.90 | 5.35 |
| hsa-let-7g | 1.83 | −0.54 | 0.21 | 1.50 | −0.24 | −0.03 | 0.83 | 0.56 | 9.30 | 11.12 | 10.59 | 10.80 | 11.84 | 11.60 | 11.57 | 12.40 |
| hsa-miR-100 | −0.46 | −1.25 | 0.22 | −1.49 | −1.05 | −2.36 | 1.69 | −1.72 | 8.00 | 7.55 | 6.29 | 6.52 | 10.72 | 9.67 | 7.32 | 9.00 |
| hsa-miR-106b | 1.39 | −0.53 | −0.18 | 0.69 | 1.33 | −0.28 | −0.09 | 0.96 | 8.08 | 9.47 | 8.94 | 8.77 | 4.43 | 5.76 | 5.48 | 5.39 |
| hsa-miR-125a-5p | 1.29 | −0.46 | −0.04 | 0.79 | 0.64 | −0.27 | 0.79 | 1.16 | 7.37 | 8.66 | 8.20 | 8.15 | 12.92 | 13.55 | 13.29 | 14.08 |
| hsa-miR-130a | 0.65 | −1.53 | −0.43 | −1.31 | −1.40 | 0.19 | −0.73 | −1.94 | 8.83 | 9.48 | 7.95 | 7.52 | 13.91 | 12.51 | 12.71 | 11.98 |
| hsa-miR-140-3p | 1.54 | −0.08 | 0.06 | 1.52 | 0.33 | 0.37 | 0.04 | 0.73 | 3.55 | 5.09 | 5.01 | 5.07 | 12.39 | 12.72 | 13.08 | 13.12 |
| hsa-miR-141 | 2.16 | −0.28 | 0.00 | 1.88 | 1.17 | 0.37 | 0.17 | 1.70 | 11.15 | 13.31 | 13.03 | 13.03 | 8.05 | 9.22 | 9.58 | 9.75 |
| hsa-miR-148a | 2.06 | −0.50 | 0.04 | 1.60 | 1.31 | −0.28 | 0.91 | 1.93 | 7.35 | 9.41 | 8.91 | 8.95 | 7.04 | 8.34 | 8.06 | 8.97 |
| hsa-miR-151-5p | 1.83 | −0.37 | 0.00 | 1.46 | 1.13 | −0.02 | −0.09 | 1.02 | 6.71 | 8.54 | 8.17 | 8.17 | 9.20 | 10.33 | 10.31 | 10.22 |
| hsa-miR-15a | 2.36 | −0.39 | −0.10 | 1.87 | 1.41 | −0.19 | 0.35 | 1.57 | 7.74 | 10.10 | 9.71 | 9.61 | 6.11 | 7.52 | 7.33 | 7.68 |
| hsa-miR-16 | 2.07 | −0.36 | −0.11 | 1.59 | 2.01 | −1.17 | 1.38 | 2.22 | 9.47 | 11.54 | 11.18 | 11.06 | 3.13 | 5.14 | 3.97 | 5.35 |
| hsa-miR-17 | 0.31 | −1.14 | −0.39 | −1.22 | −0.17 | −0.87 | −0.20 | −1.24 | 9.03 | 9.34 | 8.19 | 7.81 | 12.85 | 12.68 | 11.81 | 11.61 |
| hsa-miR-181a | 1.41 | −0.84 | −0.37 | 0.20 | 0.00 | 0.00 | 0.00 | 0.00 | 7.05 | 8.47 | 7.62 | 7.25 | 0.01 | 0.01 | 0.01 | 0.01 |
| hsa-miR-191 | 2.32 | 0.29 | −0.30 | 2.31 | 0.90 | 0.84 | 0.42 | 2.15 | 0.64 | 2.97 | 3.25 | 2.95 | 14.67 | 15.57 | 16.40 | 16.82 |
| hsa-miR-193b | −0.67 | −1.19 | −0.07 | −1.93 | −1.17 | −0.90 | 0.48 | −1.60 | 8.62 | 7.95 | 6.76 | 6.69 | 13.26 | 12.09 | 11.19 | 11.67 |
| hsa-miR-200a | 1.94 | 0.20 | 0.06 | 2.20 | 1.00 | 0.67 | 0.54 | 2.20 | 8.64 | 10.58 | 10.79 | 10.84 | 9.02 | 10.01 | 10.68 | 11.22 |
| hsa-miR-200b | 2.01 | −0.07 | 0.17 | 2.11 | 0.76 | 0.56 | 1.03 | 2.36 | 9.93 | 11.94 | 11.87 | 12.04 | 8.60 | 9.37 | 9.93 | 10.96 |
| hsa-miR-200c | 1.82 | −0.47 | 0.09 | 1.44 | 0.78 | 0.46 | 1.05 | 2.29 | 10.20 | 12.01 | 11.54 | 11.64 | 8.35 | 9.13 | 9.59 | 10.64 |
| hsa-miR-203 | 0.97 | −0.67 | 0.13 | 0.44 | 0.11 | −0.21 | 1.18 | 1.08 | 10.64 | 11.61 | 10.95 | 11.08 | 13.50 | 13.60 | 13.39 | 14.57 |
| hsa-miR-205 | 1.00 | −0.72 | −0.39 | −0.11 | 0.62 | −1.12 | 0.44 | −0.06 | 13.18 | 14.18 | 13.46 | 13.07 | 14.61 | 15.23 | 14.11 | 14.55 |
| hsa-miR-21 | 1.56 | −0.69 | 0.06 | 0.93 | −0.74 | −1.16 | 0.74 | −1.16 | 14.27 | 15.83 | 15.15 | 15.20 | 16.40 | 15.66 | 14.50 | 15.24 |
| hsa-miR-21* | 1.21 | −0.74 | −0.29 | 0.18 | 0.44 | −0.62 | −0.07 | −0.25 | 7.28 | 8.49 | 7.75 | 7.46 | 8.34 | 8.78 | 8.16 | 8.09 |
| hsa-miR-210 | 0.18 | −0.63 | −0.11 | −0.56 | −0.96 | −0.74 | −0.10 | −1.80 | 9.08 | 9.25 | 8.63 | 8.52 | 12.29 | 11.33 | 10.60 | 10.49 |
| hsa-miR-22 | 1.09 | −0.66 | 0.05 | 0.48 | 0.80 | −1.14 | 0.73 | 0.40 | 10.67 | 11.75 | 11.10 | 11.15 | 8.89 | 9.69 | 8.55 | 9.29 |
| hsa-miR-224 | 2.55 | −0.87 | 0.00 | 1.68 | 1.52 | −0.72 | 0.83 | 1.63 | 6.84 | 9.40 | 8.52 | 8.52 | 9.59 | 11.12 | 10.39 | 11.22 |
| hsa-miR-23a | 0.78 | −0.94 | 0.02 | −0.14 | 0.06 | −0.80 | 0.43 | −0.31 | 11.72 | 12.50 | 11.56 | 11.58 | 14.42 | 14.47 | 13.67 | 14.10 |
| hsa-miR-23b | 1.96 | −0.27 | 0.04 | 1.72 | 1.30 | −0.17 | 0.16 | 1.29 | 8.92 | 10.88 | 10.61 | 10.64 | 14.06 | 15.35 | 15.18 | 15.35 |
| hsa-miR-25 | 1.35 | −0.65 | −0.05 | 0.66 | 0.66 | −0.03 | −0.39 | 0.24 | 7.15 | 8.50 | 7.85 | 7.80 | 9.11 | 9.77 | 9.74 | 9.35 |
| hsa-miR-26a | 2.20 | −0.11 | 0.06 | 2.15 | 1.31 | −0.98 | 2.90 | 3.22 | 8.50 | 10.70 | 10.59 | 10.65 | 0.30 | 1.61 | 0.62 | 3.52 |
| hsa-miR-26b | 1.94 | −0.37 | 0.08 | 1.65 | 0.09 | 0.05 | 0.78 | 0.92 | 7.97 | 9.91 | 9.54 | 9.62 | 6.84 | 6.93 | 6.97 | 7.75 |
| hsa-miR-27b | 1.77 | −0.47 | 0.05 | 1.36 | 0.64 | −0.69 | −0.06 | −0.11 | 9.26 | 11.03 | 10.57 | 10.62 | 6.92 | 7.57 | 6.88 | 6.81 |
| hsa-miR-29a | 0.17 | −0.71 | 0.16 | −0.38 | −1.34 | −0.11 | 0.02 | −1.43 | 11.23 | 11.40 | 10.69 | 10.85 | 16.24 | 14.90 | 14.79 | 14.81 |
| hsa-miR-29c | 1.61 | −0.28 | 0.24 | 1.57 | 0.82 | 0.02 | 0.03 | 0.87 | 9.04 | 10.66 | 10.38 | 10.62 | 13.66 | 14.48 | 14.50 | 14.53 |
| hsa-miR-30b | 2.36 | 0.05 | 0.15 | 2.55 | 0.83 | −0.27 | 0.68 | 1.24 | 7.62 | 9.98 | 10.03 | 10.17 | 8.50 | 9.33 | 9.06 | 9.74 |
| hsa-miR-30c | 1.97 | −0.34 | −0.12 | 1.51 | 0.32 | −0.33 | −0.39 | −0.40 | 7.80 | 9.77 | 9.43 | 9.31 | 0.42 | 0.73 | 0.41 | 0.01 |
| hsa-miR-30d | 1.88 | −0.06 | 0.05 | 1.86 | 0.64 | −0.09 | 1.20 | 1.75 | 7.06 | 8.94 | 8.88 | 8.92 | 9.12 | 9.76 | 9.67 | 10.87 |
| hsa-miR-30e | 2.76 | −0.25 | −0.13 | 2.38 | 1.27 | −0.02 | 0.46 | 1.71 | 6.73 | 9.50 | 9.25 | 9.12 | 7.04 | 8.31 | 8.30 | 8.76 |
| hsa-miR-31 | 0.77 | −1.16 | −0.15 | −0.54 | −0.37 | −0.91 | 0.34 | −0.95 | 10.13 | 10.90 | 9.74 | 9.59 | 13.69 | 13.31 | 12.40 | 12.74 |
| hsa-miR-31* | 0.43 | −1.10 | −0.10 | −0.77 | −0.65 | −1.31 | 0.24 | −1.73 | 9.00 | 9.42 | 8.33 | 8.22 | 13.56 | 12.91 | 11.60 | 11.83 |
| hsa-miR-34a | 2.31 | −0.54 | 0.13 | 1.91 | 1.46 | −1.04 | 0.45 | 0.88 | 8.58 | 10.89 | 10.35 | 10.49 | 10.31 | 11.77 | 10.73 | 11.18 |
| hsa-miR-34b | 2.88 | 4.48 | 0.81 | 8.17 | 1.25 | 4.17 | 1.32 | 6.74 | 0.77 | 3.65 | 8.13 | 8.94 | 7.01 | 8.26 | 12.43 | 13.75 |
| hsa-miR-34b* | 2.02 | 3.36 | 1.10 | 6.48 | 1.22 | 3.50 | 0.95 | 5.67 | 5.96 | 7.98 | 11.35 | 12.44 | 4.99 | 6.20 | 9.70 | 10.65 |
| hsa-miR-34c-5p | 2.35 | 4.27 | 0.82 | 7.44 | 1.33 | 4.02 | 1.06 | 6.41 | 3.94 | 6.29 | 10.56 | 11.39 | 7.88 | 9.21 | 13.23 | 14.29 |
| hsa-miR-365 | −0.02 | −1.21 | 0.05 | −1.18 | −0.39 | 0.00 | 0.00 | −0.39 | 8.44 | 8.41 | 7.21 | 7.25 | 0.41 | 0.01 | 0.01 | 0.01 |
| hsa-miR-374a | 1.41 | −0.54 | −0.08 | 0.79 | −0.33 | 1.74 | 0.74 | 2.16 | 7.04 | 8.45 | 7.91 | 7.83 | 0.62 | 0.30 | 2.04 | 2.78 |
| hsa-miR-378 | 3.23 | −0.81 | −0.26 | 2.16 | 2.15 | −0.26 | −0.39 | 1.50 | 4.38 | 7.61 | 6.80 | 6.54 | 10.37 | 12.53 | 12.26 | 11.87 |
| hsa-miR-425 | 1.59 | 0.19 | −0.21 | 1.57 | 0.42 | 0.74 | −0.04 | 1.12 | 6.61 | 8.21 | 8.39 | 8.18 | 10.58 | 11.01 | 11.75 | 11.70 |
| hsa-miR-429 | 1.71 | 0.14 | 0.10 | 1.95 | 0.42 | 0.14 | 0.74 | 1.30 | 7.97 | 9.68 | 9.82 | 9.93 | 8.23 | 8.65 | 8.79 | 9.53 |
| hsa-miR-449a | 6.53 | 5.70 | −0.15 | 12.08 | 5.21 | 5.21 | 0.21 | 10.63 | 1.47 | 8.00 | 13.70 | 13.54 | 4.48 | 9.69 | 14.90 | 15.11 |
| hsa-miR-449b | 2.61 | 6.25 | −0.22 | 8.64 | 3.32 | 5.40 | −0.12 | 8.60 | 0.47 | 3.08 | 9.33 | 9.11 | 3.64 | 6.96 | 12.36 | 12.24 |
| hsa-miR-574-3p | 1.69 | −0.46 | −0.18 | 1.04 | 0.48 | 0.12 | 0.32 | 0.92 | 4.73 | 6.42 | 5.96 | 5.77 | 13.64 | 14.12 | 14.24 | 14.56 |
| hsa-miR-92b | 0.48 | 4.21 | −0.29 | 4.39 | 1.21 | 4.12 | 0.60 | 5.93 | 0.10 | 0.57 | 4.78 | 4.49 | 7.49 | 8.70 | 12.82 | 13.42 |
| hsa-miR-939 | 1.40 | −0.63 | −0.07 | 0.70 | 0.13 | −0.13 | 0.00 | 0.00 | 6.64 | 8.04 | 7.41 | 7.34 | 0.01 | 0.15 | 0.01 | 0.01 |
| hsa-miR-96 | 1.19 | −0.50 | −0.04 | 0.64 | −0.08 | −0.71 | 0.81 | 0.02 | 8.52 | 9.71 | 9.21 | 9.16 | 5.41 | 5.33 | 4.62 | 5.43 |
| hsa-miR-99a | 2.33 | 0.77 | 0.19 | 3.28 | 1.43 | 0.77 | 0.69 | 2.88 | 5.02 | 7.35 | 8.12 | 8.31 | 9.77 | 11.19 | 11.96 | 12.65 |

It should be noted that mir-449a, mir-449b, mir-449b*, mir-34a, mir-34b (3p), mir-34b* (5p), mir-34c (5p) are found to be significantly modulated during differentiation and are therefore involved in initiating and maintaining the state of differentiation of the airway epithelium.

These five miRNAs: mir-449a, mir-449b, mir-34a, mir-34b, mir-34c are found to be strongly induced during differentiation, more particularly at the start of ciliogenesis. Once induced, their expression remains high and stable throughout differentiation including in the wholly differentiated epithelium. The completely differentiated repertoire of the miRNAs of the epithelium is characterized by a remarkable abundance of these 5 miRNAs which represent nearly 20% of the total number of all the miRNAs expressed in this tissue. Regarding mir-34a, however, it is induced less strongly than the other four miRNAs and is found earlier, at stage ALI-D7.

Interestingly, the 5p strands of each of the miRNAs mir-449a, mir-449b, mir-34a, mir-34b and mir-34c share a sequence homology at the level of their recognition sequence, suggesting that they target certain transcripts in common.

That is why the inventors then concentrated their efforts on these 5 miRNAs. The levels of regulation of these miRNAs as well as of mir-31 (which is found to be repressed during differentiation of the airway epithelium) were validated by a third approach, by quantitative PCR (see FIG. 5).

These 5 miRNAs that are overexpressed during differentiation of the airway epithelium belong to two separate miRNA families: mir-449 and mir-34. Moreover, the genomic localization of mir-449a and of mir-449b is identical: both are localized at the level of the second intron of the cdc20b gene, situated on human chromosome 5 (5q11.2, chr5:54456388-54504760). The mir-34 family is composed of mir-34a which is localized in an intergenic region of chromosome 1 whereas the miRNAs mir-34b and mir-34c belong to the same cluster and both are localized in an intergenic region of chromosome 11. The mir-34 family has been linked functionally to the p53 signalling pathway.

II-2.B. Ciliated Epidermal Cells of *Xenopus* Embryos

The results obtained for this model are presented in Table IIIB below and in FIG. 6, which also presents results for the HAEC cells.

These tests show that, once again, the microRNA family miR-449, and more particularly miR-449a, constitute by far the microRNAs most strongly induced during ciliogenesis.

TABLE IIIB miRNAs significantly expressed in the ciliated cells of the *Xenopus* embryo epidermis, comparison with non-ciliated cells

| xenopus miRNA | Log Ratio of expression of miR between ciliated-non-ciliated | % of miR non-ciliated cells | % of miR ciliated cells | sd non-ciliated | sd ciliated |
|---|---|---|---|---|---|
| miR-449a | 3.166507029 | 4.241910975 | 38.99145137 | 0.66831542 | 0.5580561 |
| miR-17-5p | 1.843961214 | 1.739241798 | 6.439037664 | 0.03088444 | 0.44692614 |
| miR-427 | −3.577711451 | 84.3912305 | 7.287645762 | 3.81200367 | 0.43536764 |
| miR-18a | 1.963297831 | 1.445998485 | 5.770842336 | 0.25353698 | 0.40662557 |
| miR-203 | 2.899525765 | 0.802824596 | 6.122022692 | 0.14427702 | 0.16748381 |
| miR-429 | 3.489311848 | 0.5611861 | 6.308452174 | 0.18811487 | 0.19190601 |
| miR-34b | 8.639233391 | 0.023309799 | 6.678155706 | 0.02362849 | 0.24212636 |
| miR-130c | 3.303007088 | 0.319262952 | 3.090857721 | 0.13938414 | 0.20761583 |
| miR-20b | 0.920427989 | 1.297427834 | 1.839130412 | 1.29177087 | 0.55721948 |
| miR-200a | 2.92597595 | 0.309242272 | 2.418052837 | 0.03713634 | 0.23727106 |
| miR-130b | 5.041603605 | 0.061086987 | 2.057820515 | 0.01136075 | 0.16380899 |
| miR-106 | 2.067406718 | 0.395322902 | 1.683867839 | 0.09703348 | 0.14099092 |
| miR-93b | 0.31478571 | 0.797852579 | 0.902730776 | 0.63514139 | 0.4494722 |
| miR-93a | 0.317106219 | 0.795629375 | 0.898232543 | 0.63828547 | 0.44663817 |
| miR-26 | 2.754387045 | 0.166267205 | 1.158759618 | 0.02096265 | 0.18818027 |
| miR-20a | 2.428912948 | 0.212684269 | 1.096366145 | 0.11342212 | 0.12723715 |
| miR-218 | 12.28452357 | 0.002273204 | 1.086641349 | 0.00307337 | 0.11041905 |
| miR-34a | 1.883909316 | 0.183851237 | 0.690835543 | 0.04597169 | 0.08895895 |

II-2.C. Discussion

Whereas the miR-449s represent less than 0.01% of all the sequences of microRNAs in the HAEC cells during their multiplication, these miR-449s represent more than 8% of the microRNAs expressed in the differentiated HAEC cells (see FIG. 6 graphs a and b). Moreover, miR-449a in the cells of *Xenopus* increases significantly during differentiation, representing up to 39% of all the sequences of microRNAs in ciliated cells of epidermal explants (see FIG. 6, graphs c-d).

As pointed out above, the miR-449s and the miR-34s belong to one and the same superfamily of microRNAs. Interestingly, it is noted that expression of the members of the miR-34 family was also induced during ciliogenesis in the two models (see FIG. 6, graphs a and b), even if to a lesser extent than that of the miR-449s.

The miR-449 family seems be conserved in vertebrates: investigation of the syntenic loci of Cdc20b (where the miR-449 cluster is located in humans and in the frog) revealed the existence of miR-449 in all the genomes of vertebrates fully or partially sequenced.

The differentiated HAEC cells and the ciliated cells of the epidermis of *Xenopus laevis* consist of a mixture of different cellular types, including basal cells, mucus-secreting cells and multiciliated cells.

Hybridization in situ on HAEC primary cultures (see micrographs a and c of FIG. 7) and on human bronchial tissue (see micrographs e and g of FIG. 7) revealed that the miR-449s were expressed in the multiciliated cylindrical cells but not in the basal cells (see micrograph a of FIG. 7) or in the muc5AC-positive secretory cells (see micrograph e of FIG. 7).

These results were confirmed by the tests of high-throughput sequencing on fractions enriched with cylindrical cells (mainly composed of multiciliated cells and some mucus-secreting cells) and with basal cells, derived from the epithelium of human respiratory passages.

Graph d in FIG. 7 shows an enrichment of the miR-449s in the fraction of ciliated cells, whereas the expression of the miR-34s that is observed is more uniform and was observed in both types of cells.

Finally, hybridization in situ on the cells of *Xenopus* embryos revealed that expression of the miR-449s was restricted to the ciliated cells, said cells being positive on labeling with acetylated tubulin (see micrographs h and l of FIG. 7).

All of these results show that the miR-449s are the most abundant microRNAs of the multiciliated cells of vertebrates.

III—Determination of the Specific Targets of the Selected miRNAs

III-1. Identification of the Specific Cellular Type of Each miRNA

Like the native airway epithelium, the model of differentiation in vitro used in these tests consists of basal cells, ciliated cells and mucus-secreting cells. In order to identify the repertoires of the miRNAs specific to each of the cellular types, the inventors used cell sorting by flow cytometry by means of specific markers (Hajj, R. et al. 2007). Using this technique, adult airway progenitor cells (corresponding a priori to basal cells) were isolated, selected and sorted (such cells appear doubly positive for tetraspanin CD151 and for the tissue factor) from the pyramidal cells (i.e. ciliated cells and mucus-secreting cells) which appear negative for these same markers. These were purified from polyps or from nasal conchae obtained from 3 separate donors.

After extracting the total RNAs, the expression profiles of the miRNAs were established by means of Agilent® commercial chips or by high-throughput sequencing (HTS). The two experimental approaches corroborate, for several miRNA selected including mir-449a, mir-449b, mir-34a, mir-34b, mir-34b* (mir-34b-5p), mir-34c and mir-34c* (mir-34c-3p), their specific expression in the epithelial ciliated cells. Moreover, this cell sorting experiment is able to show that the miRNAs repressed in cells in culture (e.g. mir-31, mir-31*, mir-205, mir-130a, mir-193b) are more specific to the basal cells (see FIG. 8 and Table VII). For the first time, the inventors thus attribute a repertoire of expression of the miRNAs specifically to separate cellular types of the airway epithelium during differentiation.

TABLE VII

Specific miRNAs of the basal cells or of the pyramidal cells (ciliated + secretory) identified by HTS and Agilent ® chips.

| Name | Modulation of expression of the miRNAs in pyramidal cells (323(−)) relative to basal cells 323(+) | Intensity of the level of expression in log2 in basal cells (323(+)) | Intensity of the level of expression in log2 in pyramidal cells (323(−)) |
|---|---|---|---|
| hsa-let-7a | −1.29 | 11.93 | 10.65 |
| hsa-let-7b | −1.96 | 12.20 | 10.24 |
| hsa-let-7c | −0.48 | 9.43 | 8.95 |
| hsa-let-7e | −1.42 | 8.24 | 6.82 |
| hsa-let-7f | −0.94 | 10.82 | 9.88 |
| hsa-let-7g | −0.15 | 8.37 | 8.22 |
| hsa-miR-100 | 1.62 | 3.28 | 4.90 |
| hsa-miR-106b | −2.05 | 7.22 | 5.16 |
| hsa-miR-125a-5p | −0.05 | 6.63 | 6.58 |
| hsa-miR-130a | −6.33 | 9.76 | 3.43 |
| hsa-miR-140-3p | 0.91 | 2.75 | 3.66 |
| hsa-miR-141 | −2.88 | 11.12 | 8.24 |
| hsa-miR-148a | −1.76 | 7.14 | 5.39 |
| hsa-miR-151-5p | −0.73 | 7.24 | 6.51 |
| hsa-miR-15a | −2.10 | 7.86 | 5.75 |
| hsa-miR-16 | −0.48 | 9.10 | 8.62 |
| hsa-miR-17 | −2.60 | 6.64 | 4.04 |
| hsa-miR-181a | −2.29 | 6.88 | 4.59 |
| hsa-miR-191 | 0.00 | 0.14 | 0.14 |
| hsa-miR-193b | −3.57 | 3.90 | 0.33 |
| hsa-miR-200a | −0.95 | 8.80 | 7.85 |
| hsa-miR-200b | −0.15 | 9.99 | 9.84 |
| hsa-miR-200c | −0.67 | 10.24 | 9.57 |
| hsa-miR-203 | −3.50 | 3.64 | 0.14 |
| hsa-miR-205 | −7.00 | 12.44 | 5.44 |
| hsa-miR-21 | −1.26 | 11.34 | 10.08 |
| hsa-miR-21* | −2.20 | 5.03 | 2.83 |
| hsa-miR-210 | −2.03 | 6.60 | 4.57 |
| hsa-miR-22 | −1.73 | 8.81 | 7.07 |
| hsa-miR-224 | −2.84 | 3.65 | 0.82 |
| hsa-miR-23a | −2.45 | 10.25 | 7.80 |
| hsa-miR-23b | −2.23 | 9.41 | 7.18 |
| hsa-miR-25 | −0.70 | 5.40 | 4.70 |
| hsa-miR-26a | −2.24 | 9.92 | 7.68 |
| hsa-miR-26b | −1.47 | 8.75 | 7.28 |
| hsa-miR-27b | −3.56 | 9.77 | 6.21 |
| hsa-miR-29a | −2.95 | 11.09 | 8.14 |
| hsa-miR-29c | −3.06 | 11.06 | 8.00 |
| hsa-miR-30b | −0.80 | 8.76 | 7.96 |
| hsa-miR-30c | −1.01 | 6.92 | 5.91 |
| hsa-miR-30d | −1.11 | 8.16 | 7.05 |
| hsa-miR-30e | −1.60 | 6.94 | 5.34 |
| hsa-miR-31 | −4.31 | 6.36 | 2.05 |
| hsa-miR-31* | −3.70 | 3.84 | 0.14 |
| hsa-miR-34a | 0.64 | 6.72 | 7.36 |
| hsa-miR-34b | 8.24 | 0.88 | 9.12 |
| hsa-miR-34b* | 6.05 | 5.48 | 11.52 |
| hsa-miR-34c-5p | 5.74 | 4.75 | 10.49 |
| hsa-miR-365 | −0.99 | 4.83 | 3.84 |
| hsa-miR-374a | −1.04 | 4.26 | 3.22 |
| hsa-miR-378 | −2.43 | 4.11 | 1.68 |
| hsa-miR-425 | 0.70 | 4.52 | 5.22 |
| hsa-miR-429 | −0.31 | 6.92 | 6.61 |
| hsa-miR-449a | 6.07 | 2.81 | 8.88 |
| hsa-miR-449b | 4.05 | 0.14 | 4.18 |
| hsa-miR-574-3p | 0.91 | 3.53 | 4.44 |
| hsa-miR-768-3p | −1.20 | 10.15 | 8.95 |
| hsa-miR-92b | 1.67 | 0.40 | 2.07 |
| hsa-miR-939 | 1.28 | 4.81 | 6.08 |
| hsa-miR-96 | −1.51 | 6.81 | 5.30 |
| hsa-miR-99a | 0.99 | 5.42 | 6.40 |

III-2. Identification of the Target mRNAs of the miRNAs Selected

A major challenge in miRNA biology is to be able to identify and characterize experimentally the target mRNAs that they regulate. With this objective, in silico approaches (bioinformatic software for predicting targets) were combined with experimental approaches (transcriptome chips, ectopic expression of miRNAs as well as of reporter vectors containing the 3'-UTR portion of the gene of interest fused to luciferase). Supplementary experiments used immunocytochemistry, video-microscopy and biochemistry approaches.

Several algorithms for predicting targets have been proposed. They are generally based on: i) the complementarity between the miRNA and the 3'UTR of the target mRNA in the 5' region of the miRNA (recognition sequence); ii) phylogenetic conservation of this sequence in the 3'UTR of the target mRNA.

In order to determine the target genes potentially regulated by these miRNAs of interest, the inventors established profiling of the mRNAs by expression chip (Affymetrix, human HuGene 1.0 ST microarrays). The samples analyzed are the same as those used for measurement of the miRNAs during differentiation. A supplementary approach consisted of evaluating the transcriptome of airway epithelial cells after manipulation of the level of expression of the miRNAs selected by transfection. Target genes were selected in relation to regeneration and differentiation of the epithelium by means of bioinformatic aids (Mediante, Ingenuity Pathway™). The inventors were thus able to establish a functional link between the miRNAs previously identified and a certain number of transcripts implicated in the regeneration and differentiation of the human airway epithelium. The results obtained show that 500-1000 transcripts are associated with differentiation (see FIG. 9).

Only the expression of some genes varies between ALI-FC and ALI-WD, indicating a stability of expression of the RNAs once ciliogenesis has been initiated.

III-3. Identification in Silico of the Putative Target Genes Common to the 5p Strands of the miRNAs mir-449a, mir-449b, mir-34a, mir-34b and mir-34c The predicted target genes were recovered for each of the 5p strands of the 5 selected miRNAs mir-449a, mir-449b and mir-34a, mir-34b-5p (mir-34b*) and mir-34c-5p which share a sequence homology at the level of their recognition sequence, using predictive bioinformatic tools (i.e. TargetScan, mirbase target, picTar and Microcible 2 to 8) accessible via the Mediante network interface (www.microarray.fr). The inventors first selected the predicted target genes common to the 5 miRNAs of interest, which were validated by the methodology detailed above. Out of nearly 3500 predicted targets for each of the miRNAs taken separately, 1229 targets are common to the 5 miRNAs selected. The 1229 predicted targets were then compared with those significantly repressed (about 1000, P<0.05) during differentiation more particularly between the wholly differentiated condition and the first step of undifferentiated proliferation (ALI-WD versus ALI-D0 (n=3 donors)). Thus, the results show 62 genes common to the 5 miRNAs selected that may play a key role in the regeneration of the airway epithelium (see Table VIII). Notably caveolin-1 is found among these genes. The results show that caveolin-1 is strongly inhibited throughout differentiation (see FIG. 8).

TABLE VIII

Lists of putative target genes of the selected microRNAs found to be inhibited during differentiation of the airway epithelium.

| Gene | Modulation of expression of the gene between the stages of differentiation WD and D0-ALI | Amean (of 3 donors) | Adjust. P. Value | Accession number of the gene |
|---|---|---|---|---|
| ABLIM3 | −1.4481743 | 7.524965 | 3.82E−04 | NM_014945 |
| ADAM19 | −1.1163435 | 6.14820233 | 5.45E−07 | NM_033274 |
| ADAMTSL4 | −1.1186815 | 7.2720022 | 4.62E−04 | NM_019032 |
| ADCY7 | −1.382631 | 7.6534838 | 2.38E−07 | NM_001114 |
| AMOTL1 | −1.7460034 | 8.6474232 | 2.94E−06 | NM_130847 |
| ARPP-19 | −1.0941527 | 8.8116738 | 1.22E−05 | NM_006628 |
| BMP1 | −0.9680967 | 8.6574928 | 1.38E−05 | NM_001199 |
| BTBD11 | −1.8490199 | 7.6618604 | 1.14E−05 | NM_001018072 |
| C12orf29 | −1.2553972 | 8.48381407 | 1.68E−04 | NM_001009894 |
| CAV1 | −2.368023 | 9.93025267 | 4.53E−06 | NM_001753 |
| CDA | −2.481947 | 6.80947653 | 2.94E−07 | NM_001785 |
| CDC25A | −1.3080745 | 6.28751913 | 4.79E−06 | NM_001789 |
| CDCA5 | −1.0540303 | 6.48987507 | 1.09E−04 | NM_080668 |
| COL7A1 | −1.6867157 | 8.59302327 | 1.04E−06 | NM_000094 |
| CPM | −1.4438189 | 8.6954668 | 9.13E−03 | NM_001005502 |
| CRABP2 | −1.4293157 | 9.39830873 | 6.87E−05 | NM_001878 |
| CTNNBIP1 | −1.0108869 | 9.35766273 | 2.86E−08 | NM_020248 |
| DKK1 | −2.5935028 | 7.03329227 | 4.98E−04 | NM_012242 |
| DLL1 | 0.2733639 | 7.4865392 |  | NM_005618 |
| DSC3 | −1.3986191 | 9.60600093 | 5.07E−03 | NM_024423 |
| EFNA3 | −1.0526506 | 7.54088253 | 1.52E−03 | NM_004952 |
| EFNB1 | −1.6142037 | 8.63543853 | 1.49E−05 | NM_004429 |
| EMP1 | −3.521182 | 8.67082233 | 5.65E−04 | NM_001423 |
| FSTL3 | −1.617425 | 8.44148553 | 2.91E−06 | NM_005860 |
| FUT11 | −1.0545791 | 8.3877732 | 3.81E−04 | NM_173540 |
| GLTP | −1.197381 | 10.2894117 | 5.63E−04 | NM_016433 |
| GPX3 | −1.483986 | 8.54605007 | 1.59E−04 | NM_002084 |
| IL1RN | −2.7062559 | 9.60439793 | 2.04E−05 | NM_173841 |
| IQGAP3 | −1.1769401 | 6.3339546 | 1.56E−03 | NM_178229 |
| IRAK2 | −1.1324037 | 7.05078867 | 1.95E−04 | NM_001570 |
| ITPR2 | −1.1585075 | 6.7519412 | 9.93E−05 | NM_002223 |
| JAG1 | −0.8238893 | 10.024193 |  | NM_00214 |
| KDELR3 | −1.604097 | 6.37016313 | 1.74E−07 | NM_006855 |
| LYPD3 | −1.9136232 | 9.53049673 | 1.19E−03 | NM_014400 |
| MAP4K4 | −1.3458818 | 9.26761513 | 5.77E−07 | NM_145686 |
| MY05A | −1.5881695 | 7.809912 | 3.04E−10 | NM_000259 |
| NDRG1 | −1.3955203 | 11.7800207 | 4.34E−03 | NM_006096 |
| NEDD4 | −1.8082366 | 7.2788706 | 7.67E−04 | NM_006154 |
| NOTCH1 | −0.5783195 | 8.7229346 | 0.0256397 | NM_017617 |
| PDLIM7 | −1.3596731 | 8.12085653 | 4.91E−06 | NM_005451 |
| PEA15 | −1.1301513 | 9.77535027 | 1.27E−03 | NM_003768 |

TABLE VIII-continued

Lists of putative target genes of the selected microRNAs found to be inhibited during differentiation of the airway epithelium.

| Gene | Modulation of expression of the gene between the stages of differentiation WD and D0-ALI | Amean (of 3 donors) | Adjust. P. Value | Accession number of the gene |
|---|---|---|---|---|
| PGAM4 | −1.1640039 | 10.9063747 | 6.86E−08 | NM_001029891 |
| PNPLA3 | −1.3599861 | 6.92883227 | 4.50E−06 | NM_025225 |
| PPL | −1.1742775 | 10.6121583 | 1.74E−03 | NM_002705 |
| PRELID2 | −1.2843971 | 6.360054 | 2.69E−08 | NM_182960 |
| PRKCA | −1.1283394 | 6.67201333 | 2.48E−04 | NM_002737 |
| RAET1L | −2.9534389 | 8.77895953 | 1.67E−06 | NM_130900 |
| RIN1 | −1.23138 | 7.72833807 | 2.35E−06 | NM_004292 |
| SC5DL | −1.1485737 | 9.615791 | 3.44E−06 | NM_006918 |
| SEMA4B | −1.1518643 | 9.4275898 | 3.23E−05 | NM_198925 |
| SERPINB2 | −1.398391 | 11.0805848 | 8.01E−05 | NM_002575 |
| SERPINE1 | −2.945564 | 9.083679 | 1.16E−02 | NM_000602 |
| SLC37A2 | −1.5591718 | 7.97890727 | 2.68E−06 | NM_198277 |
| SLC4A7 | −1.5922747 | 8.1975794 | 8.73E−10 | NM_003615 |
| SPARC | −2.1890128 | 6.9962164 | 3.28E−06 | NM_003118 |
| SYNC1 | −1.1653204 | 6.9710348 | 5.37E−05 | NM_030786 |
| TGFA | −2.1820264 | 8.82130713 | 1.10E−07 | NM_003236 |
| TGFBI | −1.3975298 | 9.96521733 | 1.62E−03 | NM_000358 |
| TGM2 | −2.4139445 | 8.10195833 | 7.22E−08 | NM_004613 |
| TMBIM1 | −1.2519402 | 11.9735373 | 2.56E−04 | NM_022152 |
| TMCC3 | −1.117217 | 7.91308893 | 1.99E−06 | NM_020698 |
| TMEFF1 | −1.3004997 | 6.23670373 | 3.30E−04 | NM_0JD03692 |
| TNS4 | −1.1104828 | 9.96975587 | 3.06E−06 | NM_032865 |
| UHRF2 | −1.1846124 | 8.1264516 | 1.95E−05 | NM_152896 |
| VAT1 | −1.2608379 | 9.68055807 | 6.22E−07 | NM_006373 |
| VSIG1 | −1.3975763 | 4.822476 | 6.93E−10 | NM_182607 |
| WNT4A | 0.9209719 | 8.8476432 | 0.0017319 | NM_030761 |
| WNT7A | −2.0382706 | 8.0121046 | 1.19E−08 | NM_004625 |

To this list of target genes of interest, we can add the genes Rfx2, Rfx3, FoxJ1 and STATH which are the targets predicted by bioinformatics of miR-31 and/or miR-130a.

IV—Validation of Caveolin-1 as Target of the miRNAs Selected

Caveolin-1 (Cav-1) is a membrane protein of 22 kDa essential for the formation of small invaginations of the plasma membrane called caveolae. The Cav-1 gene is expressed in the adherent cells (endothelial, epithelial, fibroblasts, smooth muscle cells).

More particularly, it has been shown that the caveolins are present on the membrane surface of the basal and ciliated epithelial cells, indicating a crucial role in these cellular types (Krasteva, G. et al. (2006) *Respir Res* 7, 108). Loss of expression of caveolin-1 can lead to defective epithelial proliferation and differentiation (Yang, G. et al. (2008) *Exp Mol Pathol* 84, 131-140).

Moreover, the caveolins have been implicated in various forms of susceptibility to respiratory diseases. For example, the caveolae contain a variety of receptors, and Cav-1 has been implicated in reduction of the number of receptors of transforming growth factor (TGF)-beta present on the cell surface. Earlier works emphasized the probable contribution of a deficiency of caveolin-1 in several respiratory diseases on account of disturbance of the TGF-beta pathway (Le Saux, C. J. et al. (2008) *J Biol Chem* 283, 5760-5768).

Furthermore, it has been shown that several microorganisms utilize the caveolae selectively for infecting cells (Norkin, L. C. et al. (2001) *Exp Cell Res* 266, 229-238). As these caveolae are localized on the basolateral surface of the ciliated cells of the airway epithelium, they might notably be involved in the endocytosis of infectious agents when there is an epithelial lesion (Krasteva, G. et al., 2006). In fact, the adenoviruses require a loss of integrity of the epithelium or of the tight junctions to gain access to the basolateral membrane of the ciliated cells in order to exert their pathogenic capacity (Walters, R. W. et al. (1999) *J Biol Chem* 274, 10219-10226). Finally, the basal cells would be more vulnerable to infections (Pickles, R. J. et al. (1996) *Hum Gene Ther* 7, 921-931 (1996). In agreement with this, it has been shown that the number of caveolae is greater for the basal cells than the ciliated cells (Krasteva, G. et al., 2006).

IV-1. Principle of the Tests

The MicroCible algorithm was used; it identifies 7 different sites of fixation for miR-34b-5p in the transcript of Cav-1, against 3 different sites of fixation for mir-34a/34c-5p, mir-449a/b. The inventors constructed an expression vector of a reporter gene in which the whole 3'-UTR portion of Cav-1 was inserted downstream of the luciferase coding sequence. Then, the HEK293T cells were co-transfected with this vector and each of the 5 miRNAs selected (mir34a/b-5p/c-5p/449a/b), independently in comparison with a negative control miRNA.

IV-2. Material and Methods

3'-UTR Expression Vectors and Measurement of Luciferase Activity

The complete sequence of the noncoding portion (3'-UTR) of caveolin (SEQ ID No. 178) is amplified by PCR and then cloned at the XhoI and NotI sites of the psiCheck2 vector (Promega).

The synthetic microRNAs of interest (miR-34a, miR-34b*, miR-34c-5p and the negative control miR (miR-Neg1)) were synthesized by the company Ambion (Applied Biosystems). Reverse transfection was performed on HEK293T cells (20000 cells per well) in a white 96-well plate with 100 ng of plasmid vector psiCheck2 and 5 nmol of synthetic miRNA using Lipofectamine 2000 (Invitrogen) as transfection agent. 48 hours after transfection, the activities of the luciferases renilla and firefly were evaluated with the Dual Glo Luciferase Assay System kit (Promega) and were measured by means of a luminometer (Luminoskan Ascent, Thermolab system).

Identification of Signalling Pathways

The software Ingenuity Pathway Analysis (IPA) (Ingenuity Systems, Mountain View, USA) was used for identifying networks of interaction between genes of interest and other functional groups. Genes having a ratio greater than 1 were selected. Thus, it is possible to associate biological functions and diseases with our experimental results.

IV-3. Results

The inventors showed that mir-34b-5p inhibited expression of the gene of luciferase significantly (P<0.01) when the latter is fused to the noncoding 3' portion of caveolin-1. These results, added to the fact that the inventors found caveolin-1 to be strongly inhibited during differentiation, indicate that Cav-1 is a specific target of mir-34b* (mir-34b-5p) involved in the process of differentiation of the airway epithelium (FIG. 11).

It seems probable that the miRNAs, mir-449a, mir-449b, mir-34a and mir-34b*, not repressing caveolin-1, act on the regulation of one or more other genes.

According to the same principle, the test conducted with caveolin was reproduced with other target genes of interest; the 3'-UTR sequence of the following genes was cloned AREG (SEQ ID No. 179), AURKA (SEQ ID No. 180), CAPN13 (SEQ ID No. 181), CCNB1 (SEQ ID No. 182), CCNE2 (SEQ ID No. 183), CDC6 (SEQ ID No. 184), CDC25A (SEQ ID No. 185), CENPK (SEQ ID No. 186), CEP55 (SEQ ID No. 187), CDC20B (SEQ ID No. 188), E2F7 (SEQ ID No. 189), FOXM1 (SEQ ID No. 190), STATH (SEQ ID No. 191) and TOP2A (SEQ ID No. 192).

TABLE IX list of the target genes validated by at least one of the miRNAs selected

| Targets of miR-449a/b or miR-34a, b, b*, c-3p, c-5p tested experimentally | Description of the gene | Accession number of the gene | Targets validated for at least one of the miRNAs |
| --- | --- | --- | --- |
| AREG (SEQ ID No. 179) | Homo sapiens amphiregulin (AREG), mRNA. | NM_001657 | miR-449a/b and miR-34a/c-5p |
| AURKA (SEQ ID No. 180) | Homo sapiens aurora kinase A (AURKA), transcript variant 1, mRNA. | NM_198433 | miR-34b |
| CCNB1 (SEQ ID No. 182) | Homo sapiens cyclin B1 (CCNB1), mRNA. | NM_031966 | miR-449a/b and miR-34a/c-5p |
| CCNE2 (SEQ ID No. 183) | Homo sapiens cyclin E2 (CCNE2), mRNA. | NM_057749 | miR-449a/b and miR-34a/c-5p |
| CDC25A (SEQ ID No. 185) | Homo sapiens cell division cycle 25 homolog A (S. pombe) (CDC25A), transcript variant 1, mRNA. | NM_001789 | miR-449a/b and miR-34a/c-5p |
| CEP55 (SEQ ID No. 187) | Homo sapiens centrosomal protein 55 kDa (CEP55), transcript variant 1, mRNA. | NM_018131 | miR-34b* |

A target is validated if its expression is inhibited by a miRNA.

V—Identification by DNA Chips (Affymetrix®) of the Targets of the miRNAs of Interest: mir-449a, mir-449b, mir-34a, mir-34b*, mir-34c-5p In order to determine the genes modulated specifically by the expression of a miRNA of interest, each miRNA, mir-449a, mir-449b, mir-34a, mir-34b* and mir-34c-5p, is transfected in primary cultures of undifferentiated airway epithelial cells (HAECs) and investigated by transcriptome chips (Affymetrix®), 48 h after transfection, for the genes that are differentially modulated.

Since mir-449a, mir-449b, mir-34a, mir-34b*, mir-34c-5p share the same "seed" (sequence 2-7), they are able to interact with common targets. Accordingly, 95 common genes were obtained as significantly modulated by these miRNAs.

Classically, it is assumed that a miRNA will act directly on its target mRNAs to repress their expression. FIG. 12 shows the enrichment of target genes containing the complementary region of the recognition sequence of these miRNAs of interest in response to 48 h of transfection of each of these miRNAs. We observed, for the 95 modulated genes, that 41 genes are significantly repressed (see Table X).

Of these 41 repressed genes, 18 genes are predicted targets (by analysis in silico) common to the 5 miRNAs selected (see Table XI) and whose regulation by said miRNAs might play a key role in differentiation of the airway epithelium and in implementation of a therapeutic strategy for respiratory diseases (mucoviscidosis, asthma, chronic obstructive pulmonary diseases, primary ciliary dyskinesia etc.).

TABLE IX 41 repressed genes common to the miRNAs mir-34a, mir-34b*, mir-34c-5p, mir-449a and mir-449b after transfection of each of the miRNAs of interest in HAECs.

|  | Gene Description | Level of intensity of expression in log2 | Modulation in the presence of mir34a | Modulation in the presence of mir34b-5p | Modulation in the presence of mir34c-5p | Modulation in the presence of mir449a | Modulation in the presence of mir449b |
|---|---|---|---|---|---|---|---|
| HIST1H3B | history cluster 1, H3b | 7.71 | −0.57 | −0.42 | −0.74 | −1.03 | −0.66 |
| CDC2 | cell division cycle 2, G1 to S and G2 to M | 5.59 | −0.57 | −0.29 | −0.64 | −1.00 | −0.67 |
| DTL | denticleless homolog (Drosophila) | 6.47 | −0.65 | −0.38 | −0.86 | −0.97 | −0.81 |
| KLRK1/KLRC4 | killer cell lectin-like receptor subfamily K, member 1/killer cell lectin-like receptor subfamily C, member 4 | 4.16 | −0.78 | −0.90 | −0.85 | −0.97 | −0.62 |
| KIAA0101 | KIAA0101 | 6.71 | −0.88 | −0.65 | −0.84 | −0.92 | −0.72 |
| NUF2 | NUF2, NDC80 kinetochore complex component, homolog (S. cerevisiae) | 6.20 | −0.91 | −0.55 | −0.68 | −0.92 | −0.75 |
| HIST1H2BM | histone cluster 1, H2bm | 8.72 | −0.44 | −0.59 | −0.69 | −0.92 | −0.66 |
| RAD51AP1 | RAD51 associated protein 1 | 5.42 | −1.03 | −0.60 | −0.92 | −0.87 | −0.65 |
| CENPK | centromere protein K | 6.38 | −0.89 | −0.60 | −0.74 | −0.83 | −0.65 |
| CCNB2 | cyclin B2 | 6.51 | −0.65 | −0.55 | −0.59 | −0.83 | −0.77 |
| KIF11 | kinesin family member 11 | 5.98 | −0.43 | −0.20 | −0.58 | −0.82 | −0.54 |
| NUSAP1 | nucleolar and spindle associated protein 1 | 6.73 | −0.49 | −0.30 | −0.45 | −0.82 | −0.51 |
| TOP2A | topoisomerase (DNA) II alpha 170 kDa | 7.06 | −0.70 | −0.21 | −0.63 | −0.80 | −0.52 |
| DEPDC1 | DEP domain containing 1 | 5.22 | −0.80 | −0.39 | −0.54 | −0.80 | −0.71 |
| ASPM | asp (abnormal spindle) homolog, microcephaly associated (Drosophila) | 5.73 | −0.59 | −0.32 | −0.62 | −0.77 | −0.67 |
| ARHGAP11B | Rho GTPase activating protein 11B | 4.69 | −0.82 | −0.75 | −0.71 | −0.76 | −0.84 |
| HELLS | helicase, lymphoid-specific | 5.95 | −0.78 | −0.55 | −0.69 | −0.74 | −0.79 |
| CENPI | centromere protein I | 6.39 | −0.54 | −0.67 | −0.69 | −0.73 | −0.91 |
| CENPF | centromere protein F, 350/400 ka (mitosin) | 6.61 | −0.64 | −0.34 | −0.57 | −0.72 | −0.51 |
| BUB1 | BUB1 budding uninhibited by benzimidazoles 1 homolog (yeast) | 6.49 | −0.54 | −0.25 | −0.54 | −0.72 | −0.60 |
| RRM2 | ribonucleotide reductase M2 polypeptide | 7.72 | −0.57 | −0.29 | −0.76 | −0.71 | −0.60 |
| TTK | TTK protein kinase | 5.11 | −0.50 | −0.39 | −0.81 | −0.69 | −0.67 |
| ARHGDIB | Rho GDP dissociation inhibitor (GDI) beta | 8.43 | −0.54 | −0.48 | −0.70 | −0.69 | −0.59 |
| CEP55 | centrosomal protein 55 kDa | 6.68 | −0.52 | −0.37 | −0.62 | −0.68 | −0.64 |
| TPX2 | TPX2, microtubule-associated, homolog (Xenopus laevis) | 6.89 | −0.69 | −0.42 | −0.61 | −0.68 | −0.60 |
| FOXM1 | forkhead box M1 | 6.22 | −0.64 | −0.37 | −0.38 | −0.66 | −0.56 |
| AURKA | aurora kinase A | 7.42 | −0.51 | −0.38 | −0.51 | −0.65 | −0.66 |
| CASC5 | cancer susceptibility candidate 5 | 6.03 | −0.47 | −0.14 | −0.45 | −0.63 | −0.59 |

TABLE IX-continued 41 repressed genes common to the miRNAs mir-34a, mir-34b*, mir-34c-5p, mir-449a and mir-449b after transfection of each of the miRNAs of interest in HAECs.

| | Gene Description | Level of intensity of expression in log2 | Modulation in the presence of mir34a | Modulation in the presence of mir34b-5p | Modulation in the presence of mir34c-5p | Modulation in the presence of mir449a | Modulation in the presence of mir449b |
|---|---|---|---|---|---|---|---|
| SPC25 | SPC25, NDC80 kinetochore complex component, homolog (*S. cerevisiae*) | 4.93 | −0.46 | −0.32 | −0.49 | −0.61 | −0.52 |
| PRC1 | protein regulator of cytokinesis 1 | 7.81 | −0.57 | −0.48 | −0.57 | −0.60 | −0.65 |
| ARHGAP11A | Rho GTPase activating protein 11A | 6.53 | −0.40 | −0.24 | −0.46 | −0.60 | −0.53 |
| CDC25A | cell division cycle 25 homolog A (*S. pombe*) | 6.33 | −0.60 | −0.46 | −0.54 | −0.59 | −0.55 |
| PRR11 | proline rich 11 | 6.92 | −0.59 | −0.40 | −0.69 | −0.58 | −0.67 |
| CDC6 | cell division cycle 6 homolog (*S. cerevisiae*) | 7.64 | −0.38 | −0.22 | −0.57 | −0.57 | −0.52 |
| FLJ27243 | FLJ27243 protein | 6.60 | −0.48 | −0.54 | −0.47 | −0.55 | −0.65 |
| LOC100130131 | similar to melanoma antigen | 6.14 | −0.32 | −0.44 | −0.34 | −0.54 | −0.51 |
| LOC100130131 | similar to melanoma antigen | 6.14 | −0.32 | −0.44 | −0.34 | −0.54 | −0.51 |
| DLGAP5 | discs, large (*Drosophila*) homolog-associated protein 5 | 6.64 | −0.68 | −0.09 | −0.48 | −0.52 | −0.50 |
| TRIP13 | thyroid hormone receptor interactor 13 | 7.35 | −0.54 | −0.57 | −0.58 | −0.51 | −0.55 |
| LOC253724 | hypothetical LOC253724 | 3.82 | −0.59 | −0.70 | −0.95 | −0.51 | −0.79 |
| PLK4 | polo-like kinase 4 (*Drosophila*) | 6.23 | −0.43 | −0.18 | −0.58 | −0.50 | −0.55 |

TABLE XI

Predicted targets repressed and common to mir-449a, mir-449b, mir-34a, mir-34b* and mir-34c-5p and repressed after transfection of each of the miRNAs selected in HAECs.

| Gene_Symbol | Gene Description | Level of intensity of expression in log2 | Modulation in presence of mir34a | Modulation in presence of mir34b* | Modulation in presence of mir34c-5p | Modulation in presence of mir449a | Modulation in presence of mir449b |
|---|---|---|---|---|---|---|---|
| DTL | denticleless homolog (*Drosophila*) | 6.47 | −0.65 | −0.38 | −0.86 | −0.97 | −0.81 |
| KLRK1//KLRC4 | killer cell lectin-like receptor subfamily K, member 1 | 4.16 | −0.78 | −0.90 | −0.85 | −0.97 | −0.62 |
| KIAA0101 | KIAA0101 | 6.71 | −0.88 | −0.65 | −0.84 | −0.92 | −0.72 |
| CENPK | centromere protein K | 6.38 | −0.89 | −0.60 | −0.74 | −0.83 | −0.65 |
| CCNB2 | cyclin B2 | 6.51 | −0.65 | −0.55 | −0.59 | −0.83 | −0.77 |
| KIF11 | kinesin family member 11 | 5.98 | −0.43 | −0.20 | −0.58 | −0.82 | −0.54 |
| NUSAP1 | nucleolar and spindle associated protein 1 | 6.73 | −0.49 | −0.30 | −0.45 | −0.82 | −0.51 |
| TOP2A | topoisomerase (DNA) II alpha 170 kDa | 7.06 | −0.70 | −0.21 | −0.63 | −0.80 | −0.52 |
| DEPDC1 | DEP domain containing 1 | 5.22 | −0.80 | −0.39 | −0.54 | −0.80 | −0.71 |
| RRM2 | ribonucleotide reductase M2 polypeptide | 7.72 | −0.57 | −0.29 | −0.76 | −0.71 | −0.60 |
| ARHGDIB | Rho GDP dissociation inhibitor (GDI) beta | 8.43 | −0.54 | −0.48 | −0.70 | −0.69 | −0.59 |
| CEP55 | centrosomal protein 55 kDa | 6.68 | −0.52 | −0.37 | −0.62 | −0.68 | −0.64 |
| TPX2 | TPX2, microtubule-associated, homolog (*Xenopus laevis*) | 6.89 | −0.69 | −0.42 | −0.61 | −0.68 | −0.60 |
| FOXM1 | forkhead box M1 | 6.22 | −0.64 | −0.37 | −0.38 | −0.66 | −0.56 |
| AURKA | aurora kinase A | 7.42 | −0.51 | −0.38 | −0.51 | −0.65 | −0.66 |
| PRC1 | protein regulator of cytokinesis 1 | 7.81 | −0.57 | −0.48 | −0.57 | −0.60 | −0.65 |
| CDC25A | cell division cycle 25 homolog A (*S. pombe*) | 6.33 | −0.60 | −0.46 | −0.54 | −0.59 | −0.55 |
| CDC6 | cell division cycle 6 homolog (*S. cerevisiae*) | 7.64 | −0.38 | −0.22 | −0.57 | −0.57 | −0.52 |

Bioinformatic analysis using the Ingenuity Pathway Analysis software (IPA) (Ingenuity Systems, Mountain View, USA) made it possible to identify networks of interaction between these genes and associate biological functions and diseases with the experimental results (see FIG. 13).

The pathways regulated by expression of the selected miRNAs are major pathways for regulation of the cell cycle.

VI—Investigation of the Functional Effect of Suppression of Expression of the miR-449s on Ciliogenesis The effect of extinction of expression of the miR-449s on ciliogenesis was then investigated.

VI-A. Material and Methods

HAEC Cells

Six independent cultures of HAEC cells were transfected with an oligonucleotide directed against the miR-449s and conjugated with a cholesterol molecule; ciliogenesis was evaluated during the regeneration time.

These tests use an antisense oligonucleotide of miR-449a (antagomir) bound at 3' by a 2'-O-methyl bond to a molecule of cholesterol and with the sequence: 5'-$a_s c_s c_s$agcuaacaaua-cacugc$_s c_s$a-Chol-3' (SEQ. ID. No. 207) (the phosphorothioate bonds are indicated by the subscript J (obtained according to Eurogentec (Seraing, Belgium).

This antagomir targets miR-449a of *Homo sapiens* (complete correspondence) and miR-449b with a mispairing.

The negative control used is Clear-miR™ of sequence: 5'-$c_s a_s$uscgucgaucguagcg$_s c_s$a-Chol-3' (SEQ. ID. No. 208) from Eurogentec.

The antagomir (100 µM) was preincubated in fetal calf serum (FCS) for 30 min RT. Then the antagomir-FCS mixture in a differentiation medium (20 µM of antagomir) is added on the apical face of the primary HAEC cells. After 2 h at 37° C., the mixture is withdrawn to restore the air-liquid interface.

Transfection is renewed every 5 days with a freshly prepared antagomir until the control cells have reached complete differentiation (generally after 21 days).

*Xenopus laevis*

The morpholino (MO) oligonucleotides directed against the miR-449s (GeneTools, LLC, Philomath, Oreg., USA) have the sequences:

```
MO-449a:
5'-ACCAGCTAACATTACACTGCCT-3'     (SEQ. ID. No. 209)

MO-449b:
5'-GCCAGCTAAAACTACACTGCCT-3'    (SEQ. ID. No. 210)

MO-449c:
5'-ACAGCCAGCTAGCAAGTGCACTGCC-3' (SEQ. ID. No. 211)
and the control MO:
5'-TGCACGTTTCAATACAGACCGT-3'    (SEQ. ID. No. 212)
```

The anti-DLL1 MO used is that described by Morichika et al. (*Dev Growth Differ* 52 (2), 235 (2010)).

VI-B. Results and Discussion

The miR-449 invalidated by its antagomir leads to a significant reduction in the number of ciliated HAEC cells at stage ALI-D21 (mean value of inhibition of ciliogenesis: 2.3±0.3, n=6, P<0.001) (see FIG. 14), in parallel with a reduction of the same order in the expression of miR-449 (FIG. 14, micrograph b).

MiR-449 was also invalidated in the cells of *Xenopus* embryos by epidermal injection of a mixture of morpholino oligonucleotides targeting the mature miR-449. The invalidation of miR-449 prevents multiciliogenesis, as revealed by staining with acetylated tubulin at the stage of embryonic development of the tail bud and in the tadpoles (n=112) (see FIG. 14, micrographs c to i).

Multiciliogenesis requires: (i) a definite end of the cell cycle, followed by (ii) centriologenesis characterized by multiplication of hundreds of basal bodies, derived from freshly synthesized centrioles; (iii) migration of the basal bodies to the apical membrane where they act as centers of organization of the microtubules and permit assembly of the mobile axonemes.

In the two models investigated, the ratio of tubulin-positive cells (staining of the cilia) and of centrin-2-positive cells (staining of the basal bodies) is not affected by suppression of the expression of miR-449, which suggests that miR-449 acts before formation of the centrioles.

It is interesting to note that whereas invalidation of miR-449 in the epidermis of *Xenopus* suppresses multiciliogenesis, it did not suppress the expression of the mRNAs of the markers of the ciliated cells including α-tubulin, Tex15 and the transcription factor Foxj1 (see FIG. 15). These data indicate that miR-449 is necessary for terminal differentiation, but not for specification of the multiciliated cells, thus confirming the role of miR-449 as principal regulator of ciliogenesis in vertebrates.

VII—Effect of Transfection of miR-449 on the Targets of miR-449

In order to evaluate the effect of miR-449 on ciliogenesis, it seemed desirable to verify that the targets of miR-449 were inhibited during terminal differentiation and after transfection of miR-449.

VII-A. Material and Methods

Analysis of the Cell Cycle by Flow Cytometry

The cell cycles of A549 cells of lung adenocarcinoma are synchronized by overnight culture by serum deficiency and then transfected with the microRNAs; the cells are then cultured in DMEM supplemented with L-glutamine and 10% FCS up to 30% confluence. The cells are collected 48 h later, fixed with 80% ethanol and stained with 0.1 ml of propidium iodide solution (37° C., 30 minutes) containing RNAse A (50 µg/ml).

The data are read on a FACScalibur flow cytometer (Becton-Dickinson). The percentages of cells in phase G1, S and G2+M were calculated with the Pro Cellquest software.

Construction of the Plasmids and Measurements of Luciferase Activity

Complete or partial sequences of the untranslated 3' region of Areg, Ccnb1, Ccne2, Cdc25a, Dll1 and Notch1 were amplified and cloned in the psiCheck2 vector (Promega).

The constructions of psiCheck vectors thus obtained were cotransfected with synthetic microRNAs or a negative control (Ambion, Applied System) in HEK293T cells. The luciferase activity is measured as described by Pottier et al. (*PLoS One* 4 (8), e6718 (2009)).

VII-B. Results

The targets of miR-449 were defined by analysis of the following expression profiles: (i) at four stages of regeneration of HAEC cells (ALI-D0, ALI-D7, ALI-D14, ALI-D21), (ii) with multiplying HAEC cells transfected with miR-449. Functional annotation of the mRNAs differentially expressed by Gene Set Enrichment Analysis (GSEA) (Edgar et al. *Nucleic Acids Res* 30 (1), 207 (2002)) reveals a significant increase in genes associated with the G2/M stage and with ciliogenesis (see FIG. 16).

The transcripts modulated by miR-449 are analyzed with tools for predicting targets of the microRNAs (http://www-.microarray.fr:8080/merge/index) leading to the identification of several potential targets of this microRNA, which were validated with a luciferase test (FIG. 17, micrographs a, c).

A first group of validated targets of miR-449a/b comprises amphiregulin (Areg), cyclin B1 (Ccnb1), cyclin E2 (Ccne2), and the cell division cycle 25 homolog A (Cdc25A), which code for proteins involved in regulation of the cell cycle. In fact, transfection of miR-449 leads to stoppage of the cell cycle in phase G1 (FIG. 17*b*), as reported by Feng, M. et al. (*Cell Cycle* (2), 213 (2010)), Lize et al. (*Cell Death Differ* (2009), Noonan et al. (*Oncogene* 28 (14), 1714 (2009)) and Yang, X. et al. (*Genes Dev* 23 (20), 2388 (2009)), and is a crucial step before initiation of centriogenesis.

A second group of validated targets of miR-449 is composed of Notch 1 and of the Notch ligand, DLL1 (FIG. 17*c*). Interestingly, blocking of the Notch signalling pathway with a γ-secretase antagonist (DCT, 10 μM) during regeneration of the HAEC cells potentiates ciliogenesis significantly (FIG. 17*d*), which is in agreement with the review of Tsao et al. (*Development* 136 (13), 2297 (2009)).

These results are consistent with the observation that the precursors of the ciliated cells of the *Xenopus* epidermis transiently express the ligand DII1 of Notch at the moment of their specialization and that expression of DII1 decreases rapidly with time in parallel with the accumulation of miR-449 in these progenitors (FIG. 17*e*).

As could be foreseen from this observation, endogenous expression of DII1 remained high in the precursors of the ciliated cells of the embryos modified with the MO miR-449 (FIG. 17 *e* and *f*) suggesting that miR-449 represses the expression of DII1.

VIII— Effect of the Sustained Activity of DII1 on Ciliogenesis

The consequences of sustained activity of DII1 on ciliogenesis were then evaluated.

Injection of a synthetic RNA of DII1 lacking a binding site to miR-449 results in (1) excessive specialization of the ciliated cells, (2) deficient ciliogenesis in the vast majority of these cells, a phenotype identical to that observed in embryos depleted of miR-449 (FIG. 17*g*).

Lateral inhibition by Notch signalling is known to suppress the identity of the multiciliated cell. The increase in specification of the ciliated cells observed after overexpression of DII1 is probably caused by inhibition of the activity of Notch, as reported by Deblandre et al. (*Development* 126 (21), 4715 (1999)).

In parallel, suppression of expression of endogenous DII1 by morpholino oligonucleotides led to excessive specification of the ciliated cells (FIG. 17*g*). Thus, miR-449 can trigger multiciliogenesis by repressing the expression of DII1. In support of this model, deficient multiciliogenesis caused by extinction of the expression of miR-449 is effectively restored by inhibition of the target of miR-449, DII1 (FIG. 17*g*).

Thus, these results show that repression of expression of DII1 is at the center of the mechanism of action of miR-449.

The invention claimed is:

1. A method for the treatment of a disorder associated with a dysfunction of the cilia of a ciliated epithelial tissue, the method comprising the step of administering to a subject in need thereof a miRNA selected from the group consisting of hsa-miR-34a (SEQ ID NO: 38), hsa-miR-34b (SEQ ID NO: 39), hsa-miR-34c-5p (SEQ ID NO: 40), hsa-miR-449a (SEQ ID NO: 46), hsa-miR-449b (SEQ ID NO: 47), and hsa-miR-449c (SEQ ID NO: 201), wherein the disorder is selected from the group consisting of primary ciliopathies, situs inversus, male and female infertility, Alstrom syndrome, Bardet-Biedl syndrome, Meckel-Gruber syndrome, retinal degeneration, Senior-Løken syndrome or secondary ciliopathies, chronic obstructive pulmonary disease (COPD), asthma, bronchiolitis, and respiratory infections of viral origin.

2. The method of claim 1, wherein said method comprises identifying said subject in need of treatment, said method further comprising the steps of:
   (i) quantitatively measuring a level of expression of the miRNAs by the cells of said ciliated epithelial tissue of a vertebrates subject;
   (ii) establishing an expression profile of the miRNAs of said ciliated epithelial tissue of said subject;
   (iii) comparing the expression profile of the miRNAs of said subject with the expression profile of the miRNAs of the ciliated epithelial tissue, in which the level of expression is expressed as the level of intensity of expression in log 2, of one or more other healthy subjects, shown in Table I below:

| Name of the miRNA | Sequence number of the miRNA (SEQ ID) | Level of intensity of expression in log2 At the differentiated stage (WD) measured in HTS |
|---|---|---|
| hsa-miR-34a | 38 | 13.75 |
| hsa-miR-34b | 39 | 10.65 |
| Hsa-miR-34b* | 91 | 14.29 |
| hsa-miR-34c-5p | 40 | 0.01 |
| hsa-miR-449a | 46 | 12.24 |
| hsa-miR-449b | 47 | 14.56 |
| hsa-miR-449c | 201 | 10.98; | and
 (iv) identifying said subject in need of treatment if at least one of the miRNAs, the level of expression of which by said subject is reduced by at least a factor of 2, i.e. by at least one unit of log 2, relative to the level of expression of the same miRNA by said other healthy subject(s).

3. The method of claim 1, wherein the disorder involves defective regeneration and/or differentiation of airway epithelium.

4. The method of claim 3, wherein said disorder is selected from the group consisting of COPD, mucoviscidosis, asthma, primary ciliary dyskinesia, chronic inflammation of the respiratory passages, chronic infection of the respiratory passages, and respiratory failure.

5. The method of claim 1, wherein the disorder is primary ciliary dyskinesia or Kartagener syndrome.

6. The method of claim 1, wherein the disorder is mucoviscidosis.

7. The method of claim 1, wherein the disorder is COPD.

8. The method of claim 1, wherein the disorder is asthma.

9. The method of claim 3, wherein the disorder is mucoviscidosis.

10. The method of claim 3, wherein the disorder is COPD.

11. The method of claim 3, wherein the disorder is asthma.

12. The method of claim 1, wherein the miRNA is hsa-miR-34a (SEQ ID NO: 38).

13. The method of claim 1, wherein the miRNA is hsa-miR-34b (SEQ ID NO: 39).

14. The method of claim 1, wherein the miRNA is hsa-miR-34c-5p (SEQ ID NO: 40).

15. The method of claim 1, wherein the miRNA is hsa-miR-449a (SEQ ID NO: 46).

16. The method of claim 1, wherein the miRNA is hsa-miR-449b (SEQ ID NO: 47).

17. The method of claim 1, wherein the miRNA is hsa-miR-449c (SEQ ID NO: 201).

18. The method of claim 3, wherein the miRNA is hsa-miR-34a (SEQ ID NO: 38).

19. The method of claim 3, wherein the miRNA is hsa-miR-34b (SEQ ID NO: 39).

20. The method of claim 3, wherein the miRNA is hsa-miR-34c-5p (SEQ ID NO: 40).

21. The method of claim 3, wherein the miRNA is hsa-miR-449a (SEQ ID NO: 46).

22. The method of claim 3, wherein the miRNA is hsa-miR-449b (SEQ ID NO: 47).

23. The method of claim 3, wherein the miRNA is hsa-miR-449c (SEQ ID NO: 201).

* * * * *

SEQUENCE LISTING

```
<160> NUMBER OF SEQ ID NOS: 212

<210> SEQ ID NO 1
<211> LENGTH: 22
<212> TYPE: RNA
<213> ORGANISM: Homo sapiens

<400> SEQUENCE: 1
aacccguaga uccgaacuug ug                                              22

<210> SEQ ID NO 2
<211> LENGTH: 21
<212> TYPE: RNA
<213> ORGANISM: Homo sapiens

<400> SEQUENCE: 2
uaaagugcug acagugcaga u                                               21

<210> SEQ ID NO 3
<211> LENGTH: 24
<212> TYPE: RNA
<213> ORGANISM: Homo sapiens

<400> SEQUENCE: 3
ucccugagac ccuuuaaccu guga                                            24

<210> SEQ ID NO 4
<211> LENGTH: 22
<212> TYPE: RNA
<213> ORGANISM: Homo sapiens

<400> SEQUENCE: 4
cagugcaaug uuaaaagggc au                                              22
```

```
<210> SEQ ID NO 5
<211> LENGTH: 21
<212> TYPE: RNA
<213> ORGANISM: Homo sapiens

<400> SEQUENCE: 5
uaccacaggg uagaaccacg g                                            21

<210> SEQ ID NO 6
<211> LENGTH: 22
<212> TYPE: RNA
<213> ORGANISM: Homo sapiens

<400> SEQUENCE: 6
uaacacuguc ugguaaagau gg                                           22

<210> SEQ ID NO 7
<211> LENGTH: 22
<212> TYPE: RNA
<213> ORGANISM: Homo sapiens

<400> SEQUENCE: 7
ucagugcacu acagaacuuu gu                                           22

<210> SEQ ID NO 8
<211> LENGTH: 21
<212> TYPE: RNA
<213> ORGANISM: Homo sapiens

<400> SEQUENCE: 8
ucgaggagcu cacagucuag u                                            21

<210> SEQ ID NO 9
<211> LENGTH: 22
<212> TYPE: RNA
<213> ORGANISM: Homo sapiens

<400> SEQUENCE: 9
uagcagcaca uaaugguuug ug                                           22

<210> SEQ ID NO 10
<211> LENGTH: 22
<212> TYPE: RNA
<213> ORGANISM: Homo sapiens

<400> SEQUENCE: 10
uagcagcacg uaaauauugg cg                                           22

<210> SEQ ID NO 11
<211> LENGTH: 23
<212> TYPE: RNA
<213> ORGANISM: Homo sapiens

<400> SEQUENCE: 11
caaagugcuu acagugcagg uag                                          23

<210> SEQ ID NO 12
<211> LENGTH: 23
<212> TYPE: RNA
<213> ORGANISM: Homo sapiens

<400> SEQUENCE: 12
```
aacauucaac gcugucggug agu                                              23

<210> SEQ ID NO 13
<211> LENGTH: 23
<212> TYPE: RNA
<213> ORGANISM: Homo sapiens

<400> SEQUENCE: 13
caacggaauc ccaaaagcag cug                                              23

<210> SEQ ID NO 14
<211> LENGTH: 22
<212> TYPE: RNA
<213> ORGANISM: Homo sapiens

<400> SEQUENCE: 14
aacuggcccu caaagucccg cu                                               22

<210> SEQ ID NO 15
<211> LENGTH: 25
<212> TYPE: RNA
<213> ORGANISM: Homo sapiens

<400> SEQUENCE: 15
cccccacaac cgcgcuugac uagcu                                            25

<210> SEQ ID NO 16
<211> LENGTH: 22
<212> TYPE: RNA
<213> ORGANISM: Homo sapiens

<400> SEQUENCE: 16
uaacacuguc ugguaacgau gu                                               22

<210> SEQ ID NO 17
<211> LENGTH: 22
<212> TYPE: RNA
<213> ORGANISM: Homo sapiens

<400> SEQUENCE: 17
uaauacugcc ugguaaugau ga                                               22

<210> SEQ ID NO 18
<211> LENGTH: 23
<212> TYPE: RNA
<213> ORGANISM: Homo sapiens

<400> SEQUENCE: 18
uaauacugcc ggguaaugau gga                                              23

<210> SEQ ID NO 19
<211> LENGTH: 22
<212> TYPE: RNA
<213> ORGANISM: Homo sapiens

<400> SEQUENCE: 19
gugaaauguu uaggaccacu ag                                               22

<210> SEQ ID NO 20
<211> LENGTH: 22
<212> TYPE: RNA
<213> ORGANISM: Homo sapiens

<400> SEQUENCE: 20
uccuucauuc caccggaguc ug					22

<210> SEQ ID NO 21
<211> LENGTH: 22
<212> TYPE: RNA
<213> ORGANISM: Homo sapiens

<400> SEQUENCE: 21
uagcuuauca gacugauguu ga					22

<210> SEQ ID NO 22
<211> LENGTH: 22
<212> TYPE: RNA
<213> ORGANISM: Homo sapiens

<400> SEQUENCE: 22
cugugcgugu gacagcggcu ga					22

<210> SEQ ID NO 23
<211> LENGTH: 22
<212> TYPE: RNA
<213> ORGANISM: Homo sapiens

<400> SEQUENCE: 23
aagcugccag uugaagaacu gu					22

<210> SEQ ID NO 24
<211> LENGTH: 21
<212> TYPE: RNA
<213> ORGANISM: Homo sapiens

<400> SEQUENCE: 24
caagucacua gugguuccgu u					21

<210> SEQ ID NO 25
<211> LENGTH: 21
<212> TYPE: RNA
<213> ORGANISM: Homo sapiens

<400> SEQUENCE: 25
aucacauugc cagggauuuc c					21

<210> SEQ ID NO 26
<211> LENGTH: 21
<212> TYPE: RNA
<213> ORGANISM: Homo sapiens

<400> SEQUENCE: 26
aucacauugc cagggauuac c					21

<210> SEQ ID NO 27
<211> LENGTH: 22
<212> TYPE: RNA
<213> ORGANISM: Homo sapiens

<400> SEQUENCE: 27
cauugcacuu gucucggucu ga					22

<210> SEQ ID NO 28
<211> LENGTH: 22
<212> TYPE: RNA
<213> ORGANISM: Homo sapiens

```
<400> SEQUENCE: 28
uucaaguaau ccaggauagg cu                                            22

<210> SEQ ID NO 29
<211> LENGTH: 21
<212> TYPE: RNA
<213> ORGANISM: Homo sapiens

<400> SEQUENCE: 29
uucaaguaau ucaggauagg u                                             21

<210> SEQ ID NO 30
<211> LENGTH: 21
<212> TYPE: RNA
<213> ORGANISM: Homo sapiens

<400> SEQUENCE: 30
uucacagugg cuaaguucug c                                             21

<210> SEQ ID NO 31
<211> LENGTH: 22
<212> TYPE: RNA
<213> ORGANISM: Homo sapiens

<400> SEQUENCE: 31
uagcaccauc ugaaaucggu ua                                            22

<210> SEQ ID NO 32
<211> LENGTH: 22
<212> TYPE: RNA
<213> ORGANISM: Homo sapiens

<400> SEQUENCE: 32
uagcaccauu ugaaaucggu ua                                            22

<210> SEQ ID NO 33
<211> LENGTH: 22
<212> TYPE: RNA
<213> ORGANISM: Homo sapiens

<400> SEQUENCE: 33
uguaaacauc cuacacucag cu                                            22

<210> SEQ ID NO 34
<211> LENGTH: 23
<212> TYPE: RNA
<213> ORGANISM: Homo sapiens

<400> SEQUENCE: 34
uguaaacauc cuacacucuc agc                                           23

<210> SEQ ID NO 35
<211> LENGTH: 22
<212> TYPE: RNA
<213> ORGANISM: Homo sapiens

<400> SEQUENCE: 35
uguaaacauc cccgacugga ag                                            22

<210> SEQ ID NO 36
<211> LENGTH: 22
<212> TYPE: RNA
<213> ORGANISM: Homo sapiens
```

```
<400> SEQUENCE: 36
uguaaacauc cuugacugga ag                                          22

<210> SEQ ID NO 37
<211> LENGTH: 21
<212> TYPE: RNA
<213> ORGANISM: Homo sapiens

<400> SEQUENCE: 37
aggcaagaug cuggcauagc u                                           21

<210> SEQ ID NO 38
<211> LENGTH: 22
<212> TYPE: RNA
<213> ORGANISM: Homo sapiens

<400> SEQUENCE: 38
uggcaguguc uuagcugguu gu                                          22

<210> SEQ ID NO 39
<211> LENGTH: 22
<212> TYPE: RNA
<213> ORGANISM: Homo sapiens

<400> SEQUENCE: 39
caaucacuaa cuccacugcc au                                          22

<210> SEQ ID NO 40
<211> LENGTH: 23
<212> TYPE: RNA
<213> ORGANISM: Homo sapiens

<400> SEQUENCE: 40
aggcagugua guuagcugau ugc                                         23

<210> SEQ ID NO 41
<211> LENGTH: 22
<212> TYPE: RNA
<213> ORGANISM: Homo sapiens

<400> SEQUENCE: 41
uaaugccccu aaaaauccuu au                                          22

<210> SEQ ID NO 42
<211> LENGTH: 22
<212> TYPE: RNA
<213> ORGANISM: Homo sapiens

<400> SEQUENCE: 42
uuauaauaca accugauaag ug                                          22

<210> SEQ ID NO 43
<211> LENGTH: 21
<212> TYPE: RNA
<213> ORGANISM: Homo sapiens

<400> SEQUENCE: 43
acuggacuug gagucagaag g                                           21

<210> SEQ ID NO 44
<211> LENGTH: 23
<212> TYPE: RNA
```

<213> ORGANISM: Homo sapiens

<400> SEQUENCE: 44
aaugacacga ucacucccgu uga                                    23

<210> SEQ ID NO 45
<211> LENGTH: 22
<212> TYPE: RNA
<213> ORGANISM: Homo sapiens

<400> SEQUENCE: 45
uaauacuguc ugguaaaacc gu                                     22

<210> SEQ ID NO 46
<211> LENGTH: 22
<212> TYPE: RNA
<213> ORGANISM: Homo sapiens

<400> SEQUENCE: 46
uggcagugua uuguuagcug gu                                     22

<210> SEQ ID NO 47
<211> LENGTH: 22
<212> TYPE: RNA
<213> ORGANISM: Homo sapiens

<400> SEQUENCE: 47
aggcagugua uuguuagcug gc                                     22

<210> SEQ ID NO 48
<211> LENGTH: 22
<212> TYPE: RNA
<213> ORGANISM: Homo sapiens

<400> SEQUENCE: 48
cacgcucaug cacacaccca ca                                     22

<210> SEQ ID NO 49
<211> LENGTH: 22
<212> TYPE: RNA
<213> ORGANISM: Homo sapiens

<400> SEQUENCE: 49
uauugcacuc gucccggccu cc                                     22

<210> SEQ ID NO 50
<211> LENGTH: 24
<212> TYPE: RNA
<213> ORGANISM: Homo sapiens

<400> SEQUENCE: 50 ugggagcug aggcucuggg ggug                                    24

<210> SEQ ID NO 51
<211> LENGTH: 23
<212> TYPE: RNA
<213> ORGANISM: Homo sapiens

<400> SEQUENCE: 51
uuuggcacua gcacauuuuu gcu                                    23

<210> SEQ ID NO 52
<211> LENGTH: 22

```
<212> TYPE: RNA
<213> ORGANISM: Homo sapiens

<400> SEQUENCE: 52
aacccguaga uccgaucuug ug                                              22

<210> SEQ ID NO 53
<211> LENGTH: 22
<212> TYPE: RNA
<213> ORGANISM: Homo sapiens

<400> SEQUENCE: 53
caagcuugua ucuauaggua ug                                              22

<210> SEQ ID NO 54
<211> LENGTH: 22
<212> TYPE: RNA
<213> ORGANISM: Homo sapiens

<400> SEQUENCE: 54
ccgcacugug gguacuugcu gc                                              22

<210> SEQ ID NO 55
<211> LENGTH: 22
<212> TYPE: RNA
<213> ORGANISM: Homo sapiens

<400> SEQUENCE: 55
acaggugagg uucuugggag cc                                              22

<210> SEQ ID NO 56
<211> LENGTH: 22
<212> TYPE: RNA
<213> ORGANISM: Homo sapiens

<400> SEQUENCE: 56
uucacauugu gcuacugucu gc                                              22

<210> SEQ ID NO 57
<211> LENGTH: 22
<212> TYPE: RNA
<213> ORGANISM: Homo sapiens

<400> SEQUENCE: 57
cagugguuuu acccuauggu ag                                              22

<210> SEQ ID NO 58
<211> LENGTH: 22
<212> TYPE: RNA
<213> ORGANISM: Homo sapiens

<400> SEQUENCE: 58
caucuuccag uacaguguug ga                                              22

<210> SEQ ID NO 59
<211> LENGTH: 22
<212> TYPE: RNA
<213> ORGANISM: Homo sapiens

<400> SEQUENCE: 59
aaaguucuga gacacuccga cu                                              22

<210> SEQ ID NO 60
```

-continued

<210> SEQ ID NO 60
<211> LENGTH: 21
<212> TYPE: RNA
<213> ORGANISM: Homo sapiens

<400> SEQUENCE: 60
cuagacugaa gcuccuugag g                                              21

<210> SEQ ID NO 61
<211> LENGTH: 22
<212> TYPE: RNA
<213> ORGANISM: Homo sapiens

<400> SEQUENCE: 61
caggccauau ugugcugccu ca                                             22

<210> SEQ ID NO 62
<211> LENGTH: 22
<212> TYPE: RNA
<213> ORGANISM: Homo sapiens

<400> SEQUENCE: 62
ccaguauuaa cugugcugcu ga                                             22

<210> SEQ ID NO 63
<211> LENGTH: 22
<212> TYPE: RNA
<213> ORGANISM: Homo sapiens

<400> SEQUENCE: 63
acugcaguga aggcacuugu ag                                             22

<210> SEQ ID NO 64
<211> LENGTH: 22
<212> TYPE: RNA
<213> ORGANISM: Homo sapiens

<400> SEQUENCE: 64
accaucgacc guugauugua cc                                             22

<210> SEQ ID NO 65
<211> LENGTH: 22
<212> TYPE: RNA
<213> ORGANISM: Homo sapiens

<400> SEQUENCE: 65
gcugcgcuug gauuucgucc cc                                             22

<210> SEQ ID NO 66
<211> LENGTH: 22
<212> TYPE: RNA
<213> ORGANISM: Homo sapiens

<400> SEQUENCE: 66
cgggguuuug agggcgagau ga                                             22

<210> SEQ ID NO 67
<211> LENGTH: 25
<212> TYPE: RNA
<213> ORGANISM: Homo sapiens

<400> SEQUENCE: 67 gggggguguug gcgcgaacug aucga                                         25

```
<210> SEQ ID NO 68
<211> LENGTH: 22
<212> TYPE: RNA
<213> ORGANISM: Homo sapiens

<400> SEQUENCE: 68
caucuuaccg gacagugcug ga                                              22

<210> SEQ ID NO 69
<211> LENGTH: 22
<212> TYPE: RNA
<213> ORGANISM: Homo sapiens

<400> SEQUENCE: 69
caucuuacug ggcagcauug ga                                              22

<210> SEQ ID NO 70
<211> LENGTH: 22
<212> TYPE: RNA
<213> ORGANISM: Homo sapiens

<400> SEQUENCE: 70
cgucuuaccc agcaguguuu gg                                              22

<210> SEQ ID NO 71
<211> LENGTH: 22
<212> TYPE: RNA
<213> ORGANISM: Homo sapiens

<400> SEQUENCE: 71
cacuuuacaa auccugguga uc                                              22

<210> SEQ ID NO 72
<211> LENGTH: 21
<212> TYPE: RNA
<213> ORGANISM: Homo sapiens

<400> SEQUENCE: 72
gauuucagug gagugaaguu c                                               21

<210> SEQ ID NO 73
<211> LENGTH: 21
<212> TYPE: RNA
<213> ORGANISM: Homo sapiens

<400> SEQUENCE: 73
caacaccagu cgaugggcug u                                               21

<210> SEQ ID NO 74
<211> LENGTH: 22
<212> TYPE: RNA
<213> ORGANISM: Homo sapiens

<400> SEQUENCE: 74
gacacgcaca cugucgccga cu                                              22

<210> SEQ ID NO 75
<211> LENGTH: 22
<212> TYPE: RNA
<213> ORGANISM: Homo sapiens

<400> SEQUENCE: 75
aguucuucag uggcaagcuu ua                                              22
```

```
<210> SEQ ID NO 76
<211> LENGTH: 23
<212> TYPE: RNA
<213> ORGANISM: Homo sapiens

<400> SEQUENCE: 76
aaaauggugc ccuagugacu aca                                          23

<210> SEQ ID NO 77
<211> LENGTH: 22
<212> TYPE: RNA
<213> ORGANISM: Homo sapiens

<400> SEQUENCE: 77
gggguuccug gggaugggau uu                                           22

<210> SEQ ID NO 78
<211> LENGTH: 22
<212> TYPE: RNA
<213> ORGANISM: Homo sapiens

<400> SEQUENCE: 78
uggguuccug gcaugcugau uu                                           22

<210> SEQ ID NO 79
<211> LENGTH: 21
<212> TYPE: RNA
<213> ORGANISM: Homo sapiens

<400> SEQUENCE: 79
aggcggagac uugggcaauu g                                            21

<210> SEQ ID NO 80
<211> LENGTH: 22
<212> TYPE: RNA
<213> ORGANISM: Homo sapiens

<400> SEQUENCE: 80
ccuauucuug guuacuugca cg                                           22

<210> SEQ ID NO 81
<211> LENGTH: 22
<212> TYPE: RNA
<213> ORGANISM: Homo sapiens

<400> SEQUENCE: 81
ccuguucucc auuacuuggc uc                                           22

<210> SEQ ID NO 82
<211> LENGTH: 22
<212> TYPE: RNA
<213> ORGANISM: Homo sapiens

<400> SEQUENCE: 82
agagcuuagc ugauugguga ac                                           22

<210> SEQ ID NO 83
<211> LENGTH: 22
<212> TYPE: RNA
<213> ORGANISM: Homo sapiens

<400> SEQUENCE: 83
acugauuucu uuugguguuc ag                                           22
```

<210> SEQ ID NO 84
<211> LENGTH: 22
<212> TYPE: RNA
<213> ORGANISM: Homo sapiens

<400> SEQUENCE: 84
ugaccgauuu cuccuggugu uc                                              22

<210> SEQ ID NO 85
<211> LENGTH: 22
<212> TYPE: RNA
<213> ORGANISM: Homo sapiens

<400> SEQUENCE: 85
cugggaggug gauguuuacu uc                                              22

<210> SEQ ID NO 86
<211> LENGTH: 22
<212> TYPE: RNA
<213> ORGANISM: Homo sapiens

<400> SEQUENCE: 86
cugggagaag gcuguuuacu cu                                              22

<210> SEQ ID NO 87
<211> LENGTH: 22
<212> TYPE: RNA
<213> ORGANISM: Homo sapiens

<400> SEQUENCE: 87
cuuucaguca gauguuugcu gc                                              22

<210> SEQ ID NO 88
<211> LENGTH: 22
<212> TYPE: RNA
<213> ORGANISM: Homo sapiens

<400> SEQUENCE: 88
cuuucagucg gauguuuaca gc                                              22

<210> SEQ ID NO 89
<211> LENGTH: 22
<212> TYPE: RNA
<213> ORGANISM: Homo sapiens

<400> SEQUENCE: 89
ugcuaugcca acauauugcc au                                              22

<210> SEQ ID NO 90
<211> LENGTH: 22
<212> TYPE: RNA
<213> ORGANISM: Homo sapiens

<400> SEQUENCE: 90
caaucagcaa guauacugcc cu                                              22

<210> SEQ ID NO 91
<211> LENGTH: 23
<212> TYPE: RNA
<213> ORGANISM: Homo sapiens

<400> SEQUENCE: 91
uaggcagugu cauuagcuga uug                                          23

<210> SEQ ID NO 92
<211> LENGTH: 22
<212> TYPE: RNA
<213> ORGANISM: Homo sapiens

<400> SEQUENCE: 92
aaucacuaac cacacggcca gg                                           22

<210> SEQ ID NO 93
<211> LENGTH: 22
<212> TYPE: RNA
<213> ORGANISM: Homo sapiens

<400> SEQUENCE: 93
agggacuuuc aggggcagcu gu                                           22

<210> SEQ ID NO 94
<211> LENGTH: 22
<212> TYPE: RNA
<213> ORGANISM: Homo sapiens

<400> SEQUENCE: 94
cuuaucagau uguauuguaa uu                                           22

<210> SEQ ID NO 95
<211> LENGTH: 22
<212> TYPE: RNA
<213> ORGANISM: Homo sapiens

<400> SEQUENCE: 95
cuccugacuc cagguccugu gu                                           22

<210> SEQ ID NO 96
<211> LENGTH: 22
<212> TYPE: RNA
<213> ORGANISM: Homo sapiens

<400> SEQUENCE: 96
aucgggaaug ucguguccgc cc                                           22

<210> SEQ ID NO 97
<211> LENGTH: 22
<212> TYPE: RNA
<213> ORGANISM: Homo sapiens

<400> SEQUENCE: 97
auuaugacag accauuuugg ca                                           22

<210> SEQ ID NO 98
<211> LENGTH: 22
<212> TYPE: RNA
<213> ORGANISM: Homo sapiens

<400> SEQUENCE: 98
accgucacau aacaaucgac ca                                           22

<210> SEQ ID NO 99
<211> LENGTH: 22
<212> TYPE: RNA
<213> ORGANISM: Homo sapiens

<400> SEQUENCE: 99

```
cagccacaac uacccugcca cu                                              22

<210> SEQ ID NO 100
<211> LENGTH: 23
<212> TYPE: RNA
<213> ORGANISM: Homo sapiens

<400> SEQUENCE: 100
ugagugugug ugugagug ugu                                               23

<210> SEQ ID NO 101
<211> LENGTH: 22
<212> TYPE: RNA
<213> ORGANISM: Homo sapiens

<400> SEQUENCE: 101
auaacgugag cagggccgga gg                                              22

<210> SEQ ID NO 102
<211> LENGTH: 24
<212> TYPE: RNA
<213> ORGANISM: Homo sapiens

<400> SEQUENCE: 102
accccucgac uccgagaccc ccac                                            24

<210> SEQ ID NO 103
<211> LENGTH: 22
<212> TYPE: RNA
<213> ORGANISM: Homo sapiens

<400> SEQUENCE: 103
aaucaugugc agugccaaua ug                                              22

<210> SEQ ID NO 104
<211> LENGTH: 22
<212> TYPE: RNA
<213> ORGANISM: Homo sapiens

<400> SEQUENCE: 104
caagcucgcu ucuauggguc ug                                              22

<210> SEQ ID NO 105
<211> LENGTH: 80
<212> TYPE: DNA
<213> ORGANISM: Homo sapiens

<400> SEQUENCE: 105
ccuguugcca caaacccgua gauccgaacu ugugguauua guccgcacaa gcuuguaucu      60
auagguaugu gucuguuagg                                                 80

<210> SEQ ID NO 106
<211> LENGTH: 82
<212> TYPE: DNA
<213> ORGANISM: Homo sapiens

<400> SEQUENCE: 106
ccugccgggg cuaaagugcu gacagugcag auagugguucc ucuccgugcu accgcacugu    60
ggguacuugc ugcuccagca gg                                              82

<210> SEQ ID NO 107
```

```
<211> LENGTH: 86
<212> TYPE: DNA
<213> ORGANISM: Homo sapiens

<400> SEQUENCE: 107
ugccagucuc uaggucccug agacccuuua accugugagg acauccaggg ucacagguga      60
gguucuuggg agccuggcgu cuggcc                                          86

<210> SEQ ID NO 108
<211> LENGTH: 89
<212> TYPE: DNA
<213> ORGANISM: Homo sapiens

<400> SEQUENCE: 108
ugcugcuggc cagagcucuu uucacauugu gcuacugucu gcaccuguca cuagcagugc      60
aauguuaaaa gggcauuggc cguguagug                                       89

<210> SEQ ID NO 109
<211> LENGTH: 100
<212> TYPE: DNA
<213> ORGANISM: Homo sapiens

<400> SEQUENCE: 109
ugugucucuc ucugugyccu gccagugguu uuacccuaug guagguuacg ucaugcuguu      60
cuaccacagg guagaaccac ggacaggaua ccggggcacc                           100

<210> SEQ ID NO 110
<211> LENGTH: 95
<212> TYPE: DNA
<213> ORGANISM: Homo sapiens

<400> SEQUENCE: 110
cggccggccc ugggccauc uuccaguaca guguuggaug gucuaauugu gaagcuccua      60
acacugucug guaaagaugg cucccggguc gguuc                                95

<210> SEQ ID NO 111
<211> LENGTH: 68
<212> TYPE: DNA
<213> ORGANISM: Homo sapiens

<400> SEQUENCE: 111
gaggcaaagu ucugagacac uccgacucug aguaugauag aagucagugc acuacagaac      60
uuugucuc                                                             68

<210> SEQ ID NO 112
<211> LENGTH: 90
<212> TYPE: DNA
<213> ORGANISM: Homo sapiens

<400> SEQUENCE: 112
uuuccugccc ucgaggagcu cacagucuag uaugucucau ccccuacuag acugaagcuc      60
cuugaggaca gggaugguca uacucaccuc                                      90

<210> SEQ ID NO 113
<211> LENGTH: 83
<212> TYPE: DNA
<213> ORGANISM: Homo sapiens

<400> SEQUENCE: 113
ccuuggagua aaguagcagc acauaauggu uuguggauuu ugaaaaggug caggccauau      60
```

```
ugugcugccu caaaaauaca agg                                          83

<210> SEQ ID NO 114
<211> LENGTH: 89
<212> TYPE: DNA
<213> ORGANISM: Homo sapiens

<400> SEQUENCE: 114
gucagcagug ccuuagcagc acguaaauau uggcguuaag auucuaaaau uaucuccagu  60
auuaacugug cugcugaagu aagguugac                                   89

<210> SEQ ID NO 115
<211> LENGTH: 84
<212> TYPE: DNA
<213> ORGANISM: Homo sapiens

<400> SEQUENCE: 115
gucagaauaa ugucaaagug cuuacagugc agguagugau augugcaucu acugcaguga  60
aggcacuugu agcauuaugg ugac                                        84

<210> SEQ ID NO 116
<211> LENGTH: 110
<212> TYPE: DNA
<213> ORGANISM: Homo sapiens

<400> SEQUENCE: 116
ugaguuuuga gguugcuuca gugaacauuc aacgcugucg gugaguuugg aauuaaaauc  60
aaaaccaucg accguugauu guacccuaug gcuaaccauc aucuacucca            110

<210> SEQ ID NO 117
<211> LENGTH: 92
<212> TYPE: DNA
<213> ORGANISM: Homo sapiens

<400> SEQUENCE: 117
cggcuggaca gcgggcaacg gaaucccaaa agcagcuguu gucccagag cauuccagcu   60 gcgcuuggau uucguccccu gcucuccugc cu                               92

<210> SEQ ID NO 118
<211> LENGTH: 83
<212> TYPE: DNA
<213> ORGANISM: Homo sapiens

<400> SEQUENCE: 118
guggucucag aaucggggguu uugagggcga gaugaguuua guuuuauccc aacuggcccu  60
caaagucccg cuuuuggggu cau                                         83

<210> SEQ ID NO 119
<211> LENGTH: 75
<212> TYPE: DNA
<213> ORGANISM: Homo sapiens

<400> SEQUENCE: 119 aguuggucccg aguguugugg guuauuguua aguugauuua acauugucuc ccccacaac  60 cgcgcuugac uagcu                                                  75

<210> SEQ ID NO 120
<211> LENGTH: 90
<212> TYPE: DNA
```

<213> ORGANISM: Homo sapiens

<400> SEQUENCE: 120
ccgggcuccu gugagcaucu uaccggacag ugcuggauuu cccagcuuga cucuaacacu      60
gucugguaac gauguucaaa ggugacccgc                                      90

<210> SEQ ID NO 121
<211> LENGTH: 95
<212> TYPE: DNA
<213> ORGANISM: Homo sapiens

<400> SEQUENCE: 121
ccagcucggg cagccguggc caucuuacug ggcagcauug gauggaguca ggucucuaau      60
acugccuggu aaugaugacg gcggagcccu gcacg                                95

<210> SEQ ID NO 122
<211> LENGTH: 68
<212> TYPE: DNA
<213> ORGANISM: Homo sapiens

<400> SEQUENCE: 122
cccucgucuu acccagcagu guuggggugc gguugggagu cucuaauacu gccggguaau      60
gauggagg                                                              68

<210> SEQ ID NO 123
<211> LENGTH: 110
<212> TYPE: DNA
<213> ORGANISM: Homo sapiens

<400> SEQUENCE: 123
guguugggga cucgcgcgcu gggucccagug guucuuaaca guucaacagu ucuguagcgc     60
aauugugaaa uguuuaggac cacuagaccc ggcgggcgcg gcgacagcga                110

<210> SEQ ID NO 124
<211> LENGTH: 110
<212> TYPE: DNA
<213> ORGANISM: Homo sapiens

<400> SEQUENCE: 124
aaagauccuc agacaaucca ugugcuucuc uugccuuca uuccaccgga gucugucuca      60
uacccaacca gauuucagug gagugaaguu caggaggcau ggagcugaca              110

<210> SEQ ID NO 125
<211> LENGTH: 72
<212> TYPE: DNA
<213> ORGANISM: Homo sapiens

<400> SEQUENCE: 125
ugucggguag cuuaucagac ugauguugac uguugaaucu cauggcaaca ccagucgaug      60
ggcugucuga ca                                                         72

<210> SEQ ID NO 126
<211> LENGTH: 110
<212> TYPE: DNA
<213> ORGANISM: Homo sapiens

<400> SEQUENCE: 126
acccggcagu gccuccaggc gcagggcagc cccugcccac cgcacacugc gcugcccag       60 acccacugug cgugugacag cggcugaucu gugccugggc agcgcgaccc              110

```
<210> SEQ ID NO 127
<211> LENGTH: 85
<212> TYPE: DNA
<213> ORGANISM: Homo sapiens

<400> SEQUENCE: 127
ggcugagccg caguaguucu ucaguggcaa gcuuuauguc cugacccagc uaaagcugcc      60
aguugaagaa cuguugcccu cugcc                                           85

<210> SEQ ID NO 128
<211> LENGTH: 81
<212> TYPE: DNA
<213> ORGANISM: Homo sapiens

<400> SEQUENCE: 128
gggcuuucaa gucacuagug guuccguuua guagaugauu gugcauuguu ucaaaauggu     60
gcccuaguga cuacaaagcc c                                               81

<210> SEQ ID NO 129
<211> LENGTH: 73
<212> TYPE: DNA
<213> ORGANISM: Homo sapiens

<400> SEQUENCE: 129
ggccggcugg gguuccuggg daugggauuu gcuuccuguc acaaaucaca uugccaggga    60
uuuccaaccg acc                                                        73

<210> SEQ ID NO 130
<211> LENGTH: 97
<212> TYPE: DNA
<213> ORGANISM: Homo sapiens

<400> SEQUENCE: 130
cucaggugcu cuggcugcuu ggguuccugg caugcugauu ugugacuuaa gauuaaaauc     60
acauugccag ggauuaccac gcaaccacga ccuuggc                              97

<210> SEQ ID NO 131
<211> LENGTH: 84
<212> TYPE: DNA
<213> ORGANISM: Homo sapiens

<400> SEQUENCE: 131 ggccagguguu gagaggcgga dacuuggggca auugcuggac gcugcccugg gcauugcacu   60
ugucucgguc ugacagugcc ggcc                                            84

<210> SEQ ID NO 132
<211> LENGTH: 77
<212> TYPE: DNA
<213> ORGANISM: Homo sapiens

<400> SEQUENCE: 132
guggccucgu ucaaguaauc caggauaggc ugugcagguc ccaaugggcc uauucuuggu     60
uacuugcacg gggacgc                                                    77

<210> SEQ ID NO 133
<211> LENGTH: 77
<212> TYPE: DNA
<213> ORGANISM: Homo sapiens
```

-continued

<400> SEQUENCE: 133
ccgggaccca guucaaguaa uucaggauag guugugugcu guccagccug uucuccauua    60
cuuggcucgg ggaccgg    77

<210> SEQ ID NO 134
<211> LENGTH: 97
<212> TYPE: DNA
<213> ORGANISM: Homo sapiens

<400> SEQUENCE: 134
accucucuaa caaggugcag agcuuagcug auuggugaac agugauuggu uccgcuuug    60 uucacagugg cuaaguucug caccugaaga gaaggug    97

<210> SEQ ID NO 135
<211> LENGTH: 64
<212> TYPE: DNA
<213> ORGANISM: Homo sapiens

<400> SEQUENCE: 135
augacugauu ucuuuggug uucagaguca auauaauuuu cuagcaccau cugaaaucgg    60
uuau    64

<210> SEQ ID NO 136
<211> LENGTH: 88
<212> TYPE: DNA
<213> ORGANISM: Homo sapiens

<400> SEQUENCE: 136
aucucuuaca caggcugacc gauuucuccu gguguucaga gucuguuuuu gucuagcacc    60
auuugaaauc gguuaugaug uaggggga    88

<210> SEQ ID NO 137
<211> LENGTH: 88
<212> TYPE: DNA
<213> ORGANISM: Homo sapiens

<400> SEQUENCE: 137
accaaguuuc aguucaugua aacauccuac acucagcugu aauacaugga uuggcuggga    60
gguggauguu uacuucagcu gacuugga    88

<210> SEQ ID NO 138
<211> LENGTH: 89
<212> TYPE: DNA
<213> ORGANISM: Homo sapiens

<400> SEQUENCE: 138
accaugcugu agugugugua aacauccuac acucucagcu gugagcucaa gguggcuggg    60 agagguugu uuacuccuuc ugccaugga    89

<210> SEQ ID NO 139
<211> LENGTH: 70
<212> TYPE: DNA
<213> ORGANISM: Homo sapiens

<400> SEQUENCE: 139
guuguuguaa acauccccga cuggaagcug uaagacacag cuaagcuuuc agucagaugu    60
uugcugcuac    70

```
<210> SEQ ID NO 140
<211> LENGTH: 92
<212> TYPE: DNA
<213> ORGANISM: Homo sapiens

<400> SEQUENCE: 140
gggcagucuu ugcuacugua aacauccuug acuggaagcu guaaggueguu cagaggagcu    60 uucagucgga uguuuacagc ggcaggcugc ca                                  92

<210> SEQ ID NO 141
<211> LENGTH: 71
<212> TYPE: DNA
<213> ORGANISM: Homo sapiens

<400> SEQUENCE: 141
ggagaggagg caagaugcug gcauagcugu ugaacuggga accugcuaug ccaacauauu    60
gccaucuuuc c                                                         71

<210> SEQ ID NO 142
<211> LENGTH: 110
<212> TYPE: DNA
<213> ORGANISM: Homo sapiens

<400> SEQUENCE: 142
ggccagcugu gaguguuucu uuggcagugu cuuagcuggu uguugugagc aauaguaagg    60
aagcaaucag caaguauacu gcccuagaag ugcugcacgu ugggggccc               110

<210> SEQ ID NO 143
<211> LENGTH: 84
<212> TYPE: DNA
<213> ORGANISM: Homo sapiens

<400> SEQUENCE: 143
gugcucgguu uguaggcagu gucauuagcu gauuguacug uggugguuac aaucacuaac    60
uccacugcca ucaaaacaag gcac                                           84

<210> SEQ ID NO 144
<211> LENGTH: 77
<212> TYPE: DNA
<213> ORGANISM: Homo sapiens

<400> SEQUENCE: 144
agucuaguua cuaggcagug uaguuagcug auugcuaaua guaccaauca cuaaccacac    60
ggccagguaa aaagauu                                                   77

<210> SEQ ID NO 145
<211> LENGTH: 87
<212> TYPE: DNA
<213> ORGANISM: Homo sapiens

<400> SEQUENCE: 145
accgcaggga aaaugaggga cuuuuggggg cagaugugu uccauccac uaucauaaug      60 ccccuaaaaa uccuuauugc ucuugca                                        87

<210> SEQ ID NO 146
<211> LENGTH: 72
<212> TYPE: DNA
<213> ORGANISM: Homo sapiens

<400> SEQUENCE: 146
```

```
uacaucggcc auuauaauac aaccugauaa guguuauagc acuuaucaga uuguauugua    60 auugucgugug ua                                                       72

<210> SEQ ID NO 147
<211> LENGTH: 66
<212> TYPE: DNA
<213> ORGANISM: Homo sapiens

<400> SEQUENCE: 147
agggcuccug acuccagguc cuguguguua ccuagaaaua gcacuggacu uggagucaga    60
aggccu                                                               66

<210> SEQ ID NO 148
<211> LENGTH: 87
<212> TYPE: DNA
<213> ORGANISM: Homo sapiens

<400> SEQUENCE: 148
gaaagcgcuu uggaaugaca cgaucacucc cguugagugg gcacccgaga agccaucggg    60
aaugucgugu ccgcccagug cucuuuc                                        87

<210> SEQ ID NO 149
<211> LENGTH: 83
<212> TYPE: DNA
<213> ORGANISM: Homo sapiens

<400> SEQUENCE: 149
cgccggccga ugggcgucuu accagacaug guuagaccug gcccucuguc uaauacuguc    60
ugguaaaacc guccauccgc ugc                                            83

<210> SEQ ID NO 150
<211> LENGTH: 91
<212> TYPE: DNA
<213> ORGANISM: Homo sapiens

<400> SEQUENCE: 150
cuguguguga ugagcuggca guguauuguu agcugguuga auaugugaau ggcaucggcu    60
aacaugcaac ugcugucuua uugcauauac a                                   91

<210> SEQ ID NO 151
<211> LENGTH: 97
<212> TYPE: DNA
<213> ORGANISM: Homo sapiens

<400> SEQUENCE: 151
ugaccugaau cagguaggca guguauuguu agcggcugc uugggucaag ucagcagcca     60
caacuacccu gccacuugcu ucuggauaaa uucuucu                             97

<210> SEQ ID NO 152
<211> LENGTH: 96
<212> TYPE: DNA
<213> ORGANISM: Homo sapiens

<400> SEQUENCE: 152
gggaccugcg ugggugcggg cgugugagug ugugugugug agugugeguc gcuccgggc     60 cacgcucaug cacacaccca cacgcccaca cucagg                              96

<210> SEQ ID NO 153
<211> LENGTH: 96
```

-continued

<212> TYPE: DNA
<213> ORGANISM: Homo sapiens

<400> SEQUENCE: 153
cgggccccgg gcgggcggga gggacgggac gcggugcagu guuguuuuuu cccccgccaa    60
uauugcacuc gucccggccu ccggcccccc cggccc                              96

<210> SEQ ID NO 154
<211> LENGTH: 82
<212> TYPE: DNA
<213> ORGANISM: Homo sapiens

<400> SEQUENCE: 154
ugugggcagg gcccugggga gcugaggcuc uggggguggc cggggcugac ccugggccuc    60 ugcucccccag ugucugaccg cg                                            82

<210> SEQ ID NO 155
<211> LENGTH: 78
<212> TYPE: DNA
<213> ORGANISM: Homo sapiens

<400> SEQUENCE: 155
uggccgauuu uggcacuagc acauuuuugc uugugucucu ccgcucugag caaucaugug    60
cagugccaau augggaaa                                                  78

<210> SEQ ID NO 156
<211> LENGTH: 81
<212> TYPE: DNA
<213> ORGANISM: Homo sapiens

<400> SEQUENCE: 156
cccauuggca uaaacccgua gauccgaucu gugguugaag uggaccgcac aagcucgcuu    60
cuaugggucu gugucagugu g                                              81

<210> SEQ ID NO 157
<211> LENGTH: 22
<212> TYPE: RNA
<213> ORGANISM: Homo sapiens

<400> SEQUENCE: 157
ugagguagua gguuguauag uu                                             22

<210> SEQ ID NO 158
<211> LENGTH: 22
<212> TYPE: RNA
<213> ORGANISM: Homo sapiens

<400> SEQUENCE: 158
ugagguagua gguugugugg uu                                             22

<210> SEQ ID NO 159
<211> LENGTH: 22
<212> TYPE: RNA
<213> ORGANISM: Homo sapiens

<400> SEQUENCE: 159
ugagguagua gguuguaugg uu                                             22

<210> SEQ ID NO 160
<211> LENGTH: 22
<212> TYPE: RNA

```
<213> ORGANISM: Homo sapiens

<400> SEQUENCE: 160
ugagguagga gguuguauag uu                                              22

<210> SEQ ID NO 161
<211> LENGTH: 22
<212> TYPE: RNA
<213> ORGANISM: Homo sapiens

<400> SEQUENCE: 161
ugagguagua gauuguauag uu                                              22

<210> SEQ ID NO 162
<211> LENGTH: 22
<212> TYPE: RNA
<213> ORGANISM: Homo sapiens

<400> SEQUENCE: 162
ugagguagua guuuguacag uu                                              22

<210> SEQ ID NO 163
<211> LENGTH: 21
<212> TYPE: RNA
<213> ORGANISM: Homo sapiens

<400> SEQUENCE: 163
cuauacaauc uacugucuuu c                                               21

<210> SEQ ID NO 164
<211> LENGTH: 22
<212> TYPE: RNA
<213> ORGANISM: Homo sapiens

<400> SEQUENCE: 164
cuauacaacc uacugccuuc cc                                              22

<210> SEQ ID NO 165
<211> LENGTH: 22
<212> TYPE: RNA
<213> ORGANISM: Homo sapiens

<400> SEQUENCE: 165
uagaguuaca cccugggagu ua                                              22

<210> SEQ ID NO 166
<211> LENGTH: 22
<212> TYPE: RNA
<213> ORGANISM: Homo sapiens

<400> SEQUENCE: 166
cuauacggcc uccuagcuuu cc                                              22

<210> SEQ ID NO 167
<211> LENGTH: 22
<212> TYPE: RNA
<213> ORGANISM: Homo sapiens

<400> SEQUENCE: 167
cuauacaauc uauugccuuc cc                                              22

<210> SEQ ID NO 168
<211> LENGTH: 21
```

-continued

```
<212> TYPE: RNA
<213> ORGANISM: Homo sapiens

<400> SEQUENCE: 168 cguacaggc cacugccuug c                                              21

<210> SEQ ID NO 169
<211> LENGTH: 80
<212> TYPE: DNA
<213> ORGANISM: Homo sapiens

<400> SEQUENCE: 169
ugggaugagg uaguagguug uauaguuuua gggucacacc caccacuggg agauaacuau   60
acaaucuacu gucuuuccua                                               80

<210> SEQ ID NO 170
<211> LENGTH: 83
<212> TYPE: DNA
<213> ORGANISM: Homo sapiens

<400> SEQUENCE: 170
cggggugagg uaguagguug uggguuuca gggcagugau guugcccuc ggaagauaac     60 uauacaaccu acugccuucc cug                                           83

<210> SEQ ID NO 171
<211> LENGTH: 84
<212> TYPE: DNA
<213> ORGANISM: Homo sapiens

<400> SEQUENCE: 171
gcauccgggu ugagguagua gguuguaugg uuuagaguua cacccuggga guuaacugua   60
caaccuucua gcuuuccuug gagc                                          84

<210> SEQ ID NO 172
<211> LENGTH: 79
<212> TYPE: DNA
<213> ORGANISM: Homo sapiens

<400> SEQUENCE: 172
cccgggcuga gguaggaggu uguauaguug aggaggacac ccaaggagau cacuauacgg   60
ccuccuagcu uuccccagg                                                79

<210> SEQ ID NO 173
<211> LENGTH: 87
<212> TYPE: DNA
<213> ORGANISM: Homo sapiens

<400> SEQUENCE: 173
ucagagugag guaguagauu guauaguugu ggguaguga uuuuacccug uucaggagau    60
aacuauacaa ucuauugccu ucccuga                                       87

<210> SEQ ID NO 174
<211> LENGTH: 84
<212> TYPE: DNA
<213> ORGANISM: Homo sapiens

<400> SEQUENCE: 174
aggcugaggu aguaguuugu acaguuugag ggucuaugau accacccggu acaggagaua   60
acuguacagg ccacugccuu gcca                                          84
```

<210> SEQ ID NO 175
<211> LENGTH: 7
<212> TYPE: DNA
<213> ORGANISM: Homo sapiens

<400> SEQUENCE: 175 ggcagug                                                                    7

<210> SEQ ID NO 176
<211> LENGTH: 7
<212> TYPE: RNA
<213> ORGANISM: Homo sapiens

<400> SEQUENCE: 176 aaucacu                                                                    7

<210> SEQ ID NO 177
<211> LENGTH: 7
<212> TYPE: RNA
<213> ORGANISM: Homo sapiens

<400> SEQUENCE: 177 aucacua                                                                    7

<210> SEQ ID NO 178
<211> LENGTH: 1889
<212> TYPE: DNA
<213> ORGANISM: Homo sapiens

<400> SEQUENCE: 178

```
atgacatttc aaggatagaa gtatacctga ttttttttcc ttttaatttt cctggtgcca       60
atttcaagtt ccaagttgct aatacagcaa caatttatga attgaattat cttggttgaa      120
aataaaaaga tcactttctc agttttcata agtattatgt ctcttctgag ctatttcatc      180
tattttggc agtctgaatt tttaaaaccc atttaaattt ttttccttac ctttttattt       240
gcatgtggat caaccatcgc tttattggct gagatatgaa catattgttg aaaggtaatt      300
tgagagaaat atgaagaact gaggaggaaa aaaaaaaaaa agaaaagaac caacaacctc      360
aactgcctac tccaaaatgt tggtcatttt atgttaaggg aagaattcca gggtatggcc      420
atggagtgta caagtatgtg gcagattttc agcaaactc ttttcccact gtttaaggag       480
ttagtggatt actgccattc acttcataat ccagtaggat ccagtgatcc ttacaagtta      540
gaaaacataa tcttctgcct tctcatgatc caactaatgc cttactcttc ttgaaatttt      600
aacctatgat attttctgtg cctgaatatt tgttatgtag ataacaagac ctcagtgcct      660
tcctgttttt cacattttcc ttttcaaata gggtctaact cagcaactcg ctttaggtca      720
gcagcctccc tgaagaccaa aattagaata tccatgacct agttttccat gcgtgtttct      780
gactctgagc tacagagtct ggtgaagctc acttctgggc ttcatctggc aacatcttta      840
tccgtagtgg gtatggttga cactagccca atgaaatgaa ttaaagtgga ccaatagggc      900
tgagctctct gtgggctggc agtcctggaa gccagctttc cctgcctctc atcaactgaa      960
tgaggtcagc atgtctattc agcttcgttt attttcaaga ataatcacgc tttcctgaat     1020
ccaaactaat ccatcaccgg ggtggtttag tggctcaaca ttgtgttccc atttcagctg     1080
atcagtgggc ctccaaggag gggctgtaaa atggaggcca ttgtgtgagc ctatcagagt     1140
tgctgcaaac ctgaccctg ctcagtaaag cacttgcaac cgtctgttat gctgtgacac      1200
atggcccctc cccctgccag gagctttgga cctaatccaa gcatcccttt gcccagaaag     1260
```

```
aagatggggg aggaggcagt aataaaaaga ttgaagtatt ttgctggaat aagttcaaat    1320
tcttctgaac tcaaactgag gaatttcacc tgtaaacctg agtcgtacag aaagctgcct    1380
ggtatatcca aaagcttttt attcctcctg ctcatattgt gattctgcct ttggggactt    1440
ttcttaaacc ttcagttatg atttttttt catacactta ttggaactct gcttgatttt     1500
tgcctcttcc agtcttcctg acactttaat taccaacctg ttacctactt tgactttttg    1560
catttaaaac agacactggc atggatatag ttttactttt aaactgtgta cataactgaa    1620
aatgtgctat actgcatact ttttaaatgt aaagatattt ttatctttat atgaagaaaa    1680
tcacttagga aatggctttg tgattcaatc tgtaaactgt gtattccaag acatgtctgt    1740
tctacataga tgcttagtcc ctcatgcaaa tcaattactg gtccaaaaga ttgctgaaat    1800
tttatatgct tactgatata ttttacaatt ttttatcatg catgtcctgt aaaggttaca    1860
agcctgcaca ataaaaatgt ttaacggtt                                     1889

<210> SEQ ID NO 179
<211> LENGTH: 301
<212> TYPE: DNA
<213> ORGANISM: Homo sapiens

<400> SEQUENCE: 179
ctgaagataa aattacagga tatcacattg gagtcactgc caagtcatag ccataaatga    60
tgagtcggtc ctcttccag tggatcataa gacaatggac cctttttgtt atgatggttt     120
taaactttca attgtcactt tttatgctat ttctgtatat aaaggtgcac gaaggtaaaa    180 agtattttt caagttgtaa ataatttatt taatatttaa tggaagtgta tttattttac     240
agctcattaa acttttttaa ccaaacagaa aaaaaaaaa aaaaaaaaa aaaaaaaaa       300 a                                                                    301

<210> SEQ ID NO 180
<211> LENGTH: 776
<212> TYPE: DNA
<213> ORGANISM: Homo sapiens

<400> SEQUENCE: 180
gaatcgtgca ggggagaaa tccttgagcc agggctgcca tataacctga caggaacatg      60
ctactgaagt ttatttacc attgactgct gccctcaatc tagaacgcta cacaagaaat      120
atttgtttta ctcagcaggt gtgccttaac ctccctattc agaaagctcc acatcaataa    180
acatgacact ctgaagtgaa agtagccacg agaattgtgc tacttatact ggttcataat    240
ctggaggcaa ggttcgactg cagccgcccc gtcagcctgt gctaggcatg gtgtcttcac    300
aggaggcaaa tccagagcct ggctgtgggg aaagtgacca ctctgccctg accccgatca    360
gttaaggagc tgtgcaataa ccttcctagt acctgagtga gtgtgtaact tattgggttg    420
gcgaagcctg gtaaagctgt tggaatgagt atgtgattct ttttaagtat gaaaataaag    480
atatatgtac agacttgtat tttttctctg gtggcattcc tttaggaatg ctgtgtgtct    540
gtccggcacc ccggtaggcc tgattgggtt tctagtcctc cttaaccact tatctcccat    600
atgagagtgt gaaaaatagg aacacgtgct ctacctccat ttagggatt gcttgggata     660 cagaagaggc catgtgtctc agagctgtta agggcttatt ttttaaaac attggagtca     720 tagcatgtgt gtaaacttta aatatgcaaa taaataagta tctatgtcta aaaaaa        776

<210> SEQ ID NO 181
```

```
<211> LENGTH: 504
<212> TYPE: DNA
<213> ORGANISM: Homo sapiens

<400> SEQUENCE: 181
agcaaagagg aaagcagacc catggctcag acaagctcc cagtgatcac tcaagaatct     60
ggctctcatt ctaagaggct gtgctgccca gtatggtggt tgtgataaat ctaaaccagc   120
cctgcatgaa acagagtcca agctgtctcc aacagcctg ggttcggtcc ttggctggcc    180
caggcccagt taagcctgtg ccaccaagc agctcatctg agcactttgg gatgtattca    240
gcctacgttg ccctggaaaa ggaagcagga gatgtctccc tgtgggaaag gagaagagaa   300
gttgtctctg agtcccctgt caccagttgg attcattct tggaagagcc agaatgagcc    360
actttgacca ccctcgggtg ctatgggtga acaagagct gtccactggg tgtttgcaga    420
ataattacac tatcttatgt ctggatcctg atgatttcac agctaaatgg caaaaataaa    480
acatgtttcc cataaaaaaa aaaa                                          504

<210> SEQ ID NO 182
<211> LENGTH: 622
<212> TYPE: DNA
<213> ORGANISM: Homo sapiens

<400> SEQUENCE: 182
cttgtaaact tgagttggag tactatattt acaaataaaa ttggcaccat gtgccatctg     60
tacatattac tgttgcattt acttttaata aagcttgtgg ccccttttac ttttttatag   120
cttaactaat ttgaatgtgg ttacttccta ctgtagggta gcggaaaagt tgtcttaaaa   180
ggtatggtgg ggatatttt aaaaactcct tttggtttac ctgggatcc aattgatgta     240
tatgttata tactgggttc ttgttttata tacctggctt ttactttatt aatatgagtt    300
actgaaggtg atggaggtat ttgaaaattt tacttccata ggacatactg catgtaagcc   360
aagtcatgga gaatctgctg catagctcta ttttaaagta aaagtctacc accgaatccc   420
tagtccccct gttttctgtt tcttcttgtg attgctgcca taattctaag ttatttactt   480
ttaccactat ttaagttatc aactttagct agtatcttca aactttcact ttgaaaaatg   540
agaattttat attctaagcc agttttcatt ttggttttgt gttttggtta ataaaacaat   600
actcaaatac aaaaaaaaaa aa                                            622

<210> SEQ ID NO 183
<211> LENGTH: 1424
<212> TYPE: DNA
<213> ORGANISM: Homo sapiens

<400> SEQUENCE: 183
agaagataac taagcaaaca agttggaatt caccaagatt gggtagaact ggtatcactg     60
aactactaaa gttttacaga aagtagtgct gtgattgatt gccctagcca attcacaagt    120
tacactgcca ttctgatttt aaaacttaca attggcacta agaatacat ttaattattt     180
cctatgttag ctgttaaaga aacagcagga cttgtttaca agatgtctt cattcccaag     240
gttactggat agaagccaac cacagtctat accatagcaa tgttttttcct ttaatccagt   300
gttactgtgt ttatcttgat aaactaggaa ttttgtcact ggagttttgg actggataag   360
tgctacctta aagggtatac taagtgatac agtactttga atctagttgt tagattctca   420
aaattcctac actcttgact agtgcaattt ggttcttgaa aattaaattt aaacttgttt   480
acaaaggttt agttttgtaa taaggtgact aatttatcta tagctgctat agcaagctat   540
```

```
tataaaactt gaatttctac aaatggtgaa atttaatgtt ttttaaacta gtttatttgc    600
cttgccataa cacatttttt aactaataag gcttagatga acatggtgtt caacctgtgc    660
tctaaacagt gggagtacca aagaaattat aaacaagata aatgctgtgg ctccttccta    720
actgggcctt tcttgacatg taggttgctt ggtaataacc tttttgtata tcacaatttg    780
ggtgaaaaac ttaagtaccc tttcaaacta tttatatgag gaagtcactt tactactcta    840
agatatccct aaggaatttt ttttttttaat ttagtgtgac taaggcttta tttatgtttg   900
tgaaactgtt aaggtccttt ctaaattcct ccattgtgag ataaggacag tgtcaaagtg    960
ataaagctta acacttgacc taaacttcta ttttcttaag gaagaagagt attaaatata   1020
tactgactcc tagaaatcta tttattaaaa aaagacatga aaacttgctg tacataggct   1080
agctatttct aaatatttta aattagcttt tctaaaaaaa aaatccagcc tcataaagta   1140
gattagaaaa ctagattgct agtttatttt gttatcagat atgtgaatct cttctcccttt  1200 tgaagaaact atacatttat tgttacggta tgaagtcttc tgtatagttt gtttttaaac   1260
taatatttgt ttcagtattt tgtctgaaaa gaaaacacca ctaattgtgt acatatgtat   1320
tatataaact taacctttta atactgttta tttttagccc attgtttaaa aaataaaagt   1380
taaaaaaatt taactgctta aaagtaaaaa aaaaaaaaaa aaaa                    1424

<210> SEQ ID NO 184
<211> LENGTH: 1160
<212> TYPE: DNA
<213> ORGANISM: Homo sapiens

<400> SEQUENCE: 184
attcttctct tacaccccac ccgaaagtat tcagctggca tttagagagc tacagtcttc     60
attttagtgc tttacacatt cgggcctgaa aacaaatatg acctttttta cttgaagcca    120 atgaattttta atctatagat tcttttaatat tagcacagaa taatatcttt gggtcttact   180 attttaccc ataaaagtga ccaggtagac ccttttaat tacattcact acttctacca      240
cttgtgtatc tctagccaat gtgcttgcaa gtgtacagat ctgtgtagag gaatgtgtgt    300 atatttaccct cttcgtttgc tcaaacatga gtgggtattt ttttgtttgt ttttttttgtt  360 gttgttgttt tgaggcgcg tctcaccctg ttgcccaggc tggagtgcaa tggcgcgttc     420
tctgctcact acagcacccg cttcccaggt tgaagtgatt ctcttgcctc agcctcccga    480
gtagctggga ttacaggtgc ccaccaccgc gcccagctaa tttttttaatt tttagtagag   540 acagggtttt accatgttgg ccaggctggt cttgaactcc tgaccctcaa gtgatctgcc    600
caccttggcc tccctaagtg ctgggattat aggcgtgagc caccatgctc agccattaag    660
gtattttgtt aagaacttta agtttagggt aagaagaatg aaaatgatcc agaaaaatgc    720
aagcaagtcc acatggagat ttggaggaca ctggttaaag aatttatttc tttgtatagt    780
atactatgtt catggtgcag atactacaac attgtggcat tttagactcg ttgagtttct    840
tgggcactcc caagggcgtt ggggtcataa ggagactata actctacaga ttgtgaatat    900
atttattttc aagttgcatt cttttgtcttt ttaagcaatc agatttcaag agagctcaag   960 cttttcagaag tcaatgtgaa aattccttcc taggctgtcc cacagtcttt gctgccctta  1020
gatgaagcca cttgtttcaa gatgactact ttggggttgg gttttcatct aaacacattt   1080
ttccagtctt attagataaa ttagtccata tggttggtta atcaagagcc ttctgggttt   1140
ggtttggtgg cattaaatgg                                               1160
```

<210> SEQ ID NO 185
<211> LENGTH: 1778
<212> TYPE: DNA
<213> ORGANISM: Homo sapiens

<400> SEQUENCE: 185

```
gggcggcagg accagccagc agcagcccaa gcttccctcc atccccettt accctctttg      60
ctgcagagaa acttaagcaa aggggacagc tgtgtgacat ttggagaggg ggcctgggac     120
ttccatgcct taaacctacc tcccacactc ccaaggttgg agcccagggc atcttgctgg     180
ctacgcctct tctgtccctg ttagacgtcc tccgtccata tcagaactgt gccacaatgc     240
agttctgagc accgtgtcaa gctgctctga gccacagtgg gatgaaccag ccggggcctt     300
atcgggctcc agccatctca tgaggggaga ggagacggag gggagtagag aagttacaca     360
gaaatgctgc tggccaaata gcaaagacaa cctgggaagg aaaggtcttt gtgggataat     420
ccatatgttt aatttattca acttcatcaa tcactttatt ttatttttttt ttctaactcc     480
tggagactta ttttactgct tcattaggtt gaaatactgc cattctaggt agggttttat     540
tatcccaggg actacctcgg cttttaattt aaaaaaaaaa aagaagtggg taagaaaatg     600
caaacctgtt ataagttatc ggacagaaag ctaggtgctc tgtcaccccc aggaggcgct     660
gtggtactgg ggctgctgct atttaagcca agaactgagg tcctggtgag agcgttggac     720
ccaggcttgg ctgcctgaca taagctaaat ctcccagacc caccactggc taccgatatc     780
tatttggtgg gaggtgtggc cctgttcttc ctcaccccag ttccatgaca ttggctggta     840
taggagccac agtcaggaaa gcacttgagg cagcatctgt tgggccaccc ccggctcagt     900
gctggaatgt tgcagtgtag gtttcccagg aagggggggt ggggtaggt gggctccaca     960
ggatggggga ggagcatgtc cactgagtat cttccttatg ttgctgtgat attgatagct    1020
tttatttttct aattttttaaa aaatggtcat attatgagtc aaagagtatc aaatcagtgt    1080
tggatggacc acccaagggt gaggagaggg gctggaagcc ctgggcatta ggagaaggga    1140
gtgggtgctg gcatggacat gactggatag aattttctca ggagggagct tggtggattt    1200
tgaaggtaaa actttctggg tttatcatgt tttaattttta gagacaggga gtgatgaatc    1260
atcaccggtt gtccccttat ctaactccat aaaagtggga atttcaaaag aacacctcat    1320
ccaaggagct ggggcagact tcattgattc tagagagacc tgtttcagtg cctactcatc    1380
cctgccctct ggtgccagcc tccttaccat cacggcttca ctgaggtgta ggtgggtttt    1440
tcttaaacag agacagtct ctcccctctt acctcaactt cttggggtgg aatcagtga    1500
tactggagat ggctagttgc tgtgttacgg gtttgagtta catttggcta taaaacaatc    1560
ttgttgggaa aaatgtgggg gagaggactt cttcctacac gcgcattgag acagattcca    1620
actggttaat gatattgttt gtaagaaaga gattctgttg gttgactgcc taaagagaaa    1680
ggtgggatgg ccttcagatt ataccagctt agctagcatt actaaccaac tgttggaagc    1740
tctgaaaata aagatcttg aacccataaa aaaaaaaa                             1778
```

<210> SEQ ID NO 186
<211> LENGTH: 759
<212> TYPE: DNA
<213> ORGANISM: Homo sapiens

<400> SEQUENCE: 186

```
aaggatgttt tcttttttca cacagtaaaa attcttatca ttcaaggata ttggaaccac      60
aggactattt ggataaaaaa cattatttgc aaattaatgc gcataggcca tcttactttt     120
```

```
attgcaaaat ggcatgtgct gccatctatt attcattttt aaatggtcat ttcttattca    180
gtgagtgctt tagtgtttta aactatatgg ataagaatgc aggtagataa tattctaggc    240
ataaaacatt taatgtacct tacctcatgc aatattcttt ggattctttg ttgatttatg    300
atattgctaa tataatattt tcttaaaata tataacaata tcttttatgc attttgagtt    360
ccagctggtg cttctttata tttagaaatt ataatgggaa ggtcatttaa tttacagatg    420
gttttaaaat tgaggtaata tctgaggtgg cataatttaa aaatatttag caaatttgtt    480
tcatatatac tgtcttattt ctagatttgt ttaaaattgg aatatgaaaa actaatggat    540
aaagctagca taaaattgat attttagttt gtattattaa tatatcatgt taccttatat    600
attaatctac tcttgattct gctaattatt accaacaaaa ttgtattcat gacattttat    660
taatcctctg tgaattttct gtaaataaaa ttatttctga aatctctaa aaaaaaaaaa    720 aaaaaaaaaa agaaaaaaaa aaaaaaaaaa aaaaaaaa                            759
```

<210> SEQ ID NO 187
<211> LENGTH: 956
<212> TYPE: DNA
<213> ORGANISM: Homo sapiens

<400> SEQUENCE: 187

```
caaaataagt atttgttttg atattaaaag attcaatact gtattttctg ttagcttgtg     60
ggcattttga attatatatt tcacattttg cataaaactg cctatctacc tttgacactc    120
cagcatgcta gtgaatcatg tatcttttag gctgctgtgc atttctcttg gcagtgatac    180
ctccctgaca tggttcatca tcaggctgca atgacagaat gtggtgagca gcgtctactg    240
agactactaa cattttgcac tgtcaaaata cttggtgagg aaaagatagc tcaggttatt    300
gctaatgggt taatgcacca gcaagcaaaa tattttatgt tttgggggtt tgaaaaatca    360
aagataatta accaaggatc ttaactgtgt tcgcattttt tatccaagca cttagaaaac    420
ctacaatcct aattttgatg tccattgtta agaggtggtg atagatacta ttttttttt     480 catattgtat agcggttatt agaaaagttg gggattttct tgatctttat tgctgcttac    540
cattgaaact taacccagct gtgttcccca actctgttct gcgcacgaaa cagtatctgt    600
ttgaggcata atcttaagtg gccacacaca atgttttctc ttatgttatc tggcagtaac    660
tgtaacttga attacattag cacattctgc ttagctaaaa ttgttaaaat aaactttaat    720
aaacccatgt agccctctca tttgattgac agtatttag ttattttggg cattcttaaa    780
gctgggcaat gtaatgatca gatctttgtt tgtctgaaca ggtattttta tacatgctt     840 ttgtaaacca aaaacttta aatttcttca ggttttctaa catgcttacc actgggctac    900
tgtaaatgag aaaagaataa aattatttaa tgtttttaaaa aaaaaaaaaa aaaaaa       956
```

<210> SEQ ID NO 188
<211> LENGTH: 1223
<212> TYPE: DNA
<213> ORGANISM: Homo sapiens

<400> SEQUENCE: 188

```
cacccagccc ctctaggttt cagtttcctt atttctgagt gaagatgatg atgttggcta     60
tgtcttctcc atggggtttt tatgagtatc aaacaagttg aaatactctt cttgatgtga    120
atgcctgttc tcctgttctt cttttgcaga ttgctttact tgctctgctt cccagagatc    180
cgcttctttt cttctctgct ttcttctttc tgcccctctt cctccccctc ctcttcttcc    240
```

```
tcccattctt accccttcct agagattcat tttcactact ttattcagaa taacatctat      300
agcaaagatt tctacttctt tcccgtatga ctttctccc cagctccaaa cctcatattt       360
ctgattgcct caggatagtt cccttttgag atactttcct gtctttagct caatctcaac      420
acattgaaaa cacaactcat tcacttgaaa aacacttact aaaatctcac tatatgctag      480
gcagtatgtt aagcatgcat attgctctct ctaaaaatca gttctgtagg aatccctttc      540
ccctcctgat ggtctcatcc ttatcctggt ctcccactca gggaacctcc tgattattct      600
gctctgtgct tcctcagttc acctttgct ctcttttctt ttgcttcacc tagtcacatc       660
ctgtgtgcct gacagccagt ctgctgtaat tgtcttagaa ctgatcctct tgactccaca      720
ccactgctag gttgaacatc taaaagtcct gtgctgatcc tctcagtccc ctgctcatca      780
actctcaagg acaacctatt accaaacacc tttgacctca acctctggag tcctcagccc      840
aggacttgaa gttaggagat cttttttgc cttggctctg ccataaatac accctgtaac      900
cttggatgtg ttgcaacatc tgcaaggata ggaatttgat cactgctaag gttccttcaa      960
acttgatcag ttcgctgttc tgtcttttgg atgttaattc acattcatct cctatattaa     1020
gactttggct aagtcttgtg atttcttgcc ttattggagc ttttcttcta atctgaattc     1080
ttgcttctct ctccttttcc tttacacacc cacacaagtc ctaacctctc caggaagtgt     1140
tttgaaatga tgttacctgg gtttgagttc ttggcattag cctgtatcat ctatttggta     1200
ttattatact attatagctg ttt                                              1223

<210> SEQ ID NO 189
<211> LENGTH: 2770
<212> TYPE: DNA
<213> ORGANISM: Homo sapiens

<400> SEQUENCE: 189
cctgccgctt tgccaggtgg gggtgggatc aaacgccctg agagtcccgg atgtccgagg       60
cgggatgcaa accatcccgt cctgagcacg ggtccttcct ctctctttca tccacacttc      120
tgttaacttc ccaccaccat caatcatctg atttcctgaa agtaattaat tgtgcattta      180
ataccagtta gagttccgac tctgcatggt gtcacagtga aagcgccgac tgacttatgg      240
ttttgattca agaatcgtct tattctggaa gtagatctga ataggctacc ggagccttgt      300 tttctaaag gggggcgctg tctagcactt aactagggta agcattctta acatgtattt      360
ccacttgccc tgagtaaatc tgtggtgaga gaagcttcct ttctgcagtt taaaaagct       420 actgcttcct taggcttcat caggaagcca ccttcagttg tgaatcctat ggtgttattt      480 atttgttcc tgaaatggga tttagtgcaa aaagtttaca actacagtct ttaacacatt      540
tttttcaggg tatgacgact tgaatgttta tacttttatt ctataatttg ccctgcactt      600 atttacaac ctagtaataa tgtggataaa tgtatctaca tgacacatgt caagaccaaa      660
ataactgtga atgacacacc ttgctgtaaa tgaactgtgc taaccctgac tgtgggcttg      720
agaacaaaga tgaactctag aactctagca gcctaactgc tgcttctcaa ataactgtgt      780
gaacagtgag atattactgt ttgtttctaa aaatcctact gtgcccagtt tccttcacta      840
catgccctgc attttttatt taaatattta gctgtagcgc catcagatat ggatgccttc      900
taacaattgc tgtttgtaaa ataaatcagg atggtagaaa gtgattatat ggaaaattgg      960
aacctggatg agacctttc gttgaattct gaagagtaat gatgtgaaaa ttgatacagg     1020
gcaagagatg attcttttgt ttttcttcta cttcatgtcc agaagagtaa gagggaaaat     1080
ggacatatgt ttcatatcca agggtattca aactgtagtt agttggtacc tctgaaaaat     1140
```

-continued

| | |
|---|---|
| gagaatggtg agcgcacggg ttggttgttc tagcatgaat acaattctgg aaactgttat | 1200 |
| gcaatttccc ttttttaacc cacattactt tagggggtgca ttaagtcgcc aaactatact | 1260 |
| agttctttgt attcctagac ttgctgatat ttacctctct cttgtctctt cagagtaaat | 1320 |
| ggttcccttc tttccttcct actttccttc attctctctt ccttccctcc ttcctacttc | 1380 |
| ttttcttcct tcctcttcct ctcttaaaac tatcttagat gtagaatcct ggtgtagggt | 1440 |
| tttattttat ttttatttt tgacccaata aaatgttata tgaaagaatg aaatattaa | 1500 |
| tttaagagac tctgggagtc tgaataaagt agctttatat taactacagg ataatattag | 1560 |
| ccttattacc cccacaagat tttttaaaac ttgaggtagg tagctacatt aaataaattt | 1620 |
| gctacttata taaaaatttt tatcaacact aaacttttaa agtttacaag tttttttttt | 1680 |
| cttttttaca gtcttctata gagttaggtt aaaaatgtgg ttctaaccat caacaattgc | 1740 |
| atggttaaat gaccctgaac taaaactgat gggttcccta tcaaaacaaa taaaaatata | 1800 |
| ccttttttcag gtttcaatct gtgcagggta tatgcatgtt aattctacca tgcttaagaa | 1860 |
| cttccacaaa atatttcatg gagaggtctg catttagacg gaaacagaaa ttgcttttcc | 1920 |
| cctcactgtt cctgaatgct ctatacttgt tttaacattt ttgctatctt tttttattat | 1980 |
| tctgatcatg atatgaccat ttaacctcag aattcataat tcctgagggg tgttaagaag | 2040 |
| cagtcccatt ggtgaggata ttatgacttg gtgaccattc ttaggagtag aaaaccaagg | 2100 |
| acaattgctt ctgtattcag tatccacttc ttaatgtggc tttatatgta aaaataataa | 2160 |
| tgcagtggtt gtttctgtca ggaaaataaa tcttacagaa caactggtgg aattgaagct | 2220 |
| gctgcgctag acttggatat tttgggtagt gaagaagcaa tggcaatctt gagtctatta | 2280 |
| ttgtataatt tagtaaaaga aaaaaataat cgttggtggt cctactaaga gaatgcagct | 2340 |
| tttttgagtt gtcacagagg ctgtgtgtgc cctacactga ccagggtttg taaaacccctt | 2400 |
| tcattctggt acaagagtcg ggggtataac ttttatactt gaatctacct accaagttta | 2460 |
| catttctcaa ttcctttttg taaggtgcta tttctgtatt taaataactt tcttttaacg | 2520 |
| taaagctgct ttctgcttat cttattgcac tgctagttgt atgtaggtat taattttatt | 2580 |
| gctgcttact gcttttgttt tcttattatt tagctctgct cttttttccta atggctatat | 2640 |
| tatctatagc tatttacttg taactgtact acatgtaaac tgattttttg ttctgatttt | 2700 |
| ttttctaata tttttaggaa aatattaagc tttataaaat agcaataaaa aataattcat | 2760 |
| ttaagaagaa | 2770 |

<210> SEQ ID NO 190
<211> LENGTH: 970
<212> TYPE: DNA
<213> ORGANISM: Homo sapiens

<400> SEQUENCE: 190

| | |
|---|---|
| agccctgccc ttgcccctgt gctcaagctg tccaccatcc cgggcactcc aaggctcagt | 60 |
| gcaccccaag cctctgagtg aggacagcag gcagggactg ttctgctcct catagctccc | 120 |
| tgctgcctga ttatgcaaaa gtagcagtca caccctagcc actgctggga ccttgtgttc | 180 |
| cccaagagta tctgattcct ctgctgtccc tgccaggagc tgaagggtgg gaacaacaaa | 240 |
| ggcaatggtg aaaagagatt aggaaccccc cagcctgttt ccattctctg cccagcagtc | 300 |
| tcttaccttc cctgatcttt gcagggtggt ccgtgtaaat agtataaatt ctccaaatta | 360 |
| tcctctaatt ataaatgtaa gcttattcc ttagatcatt atccagagac tgccagaagg | 420 |

```
tgggtaggat gacctggggt tcaattgac ttctgttcct tgcttttagt tttgatagaa    480
gggaagacct gcagtgcacg gtttcttcca ggctgaggta cctggatctt gggttcttca    540
ctgcagggac ccagacaagt ggatctgctt gccagagtcc ttttttgcccc tccctgccac   600
ctccccgtgt ttccaagtca gctttcctgc aagaagaaat cctggttaaa aaagtctttt    660
gtattgggtc aggagttgaa tttggggtgg gaggatggat gcaactgaag cagagtgtgg    720
gtgcccagat gtgcgctatt agatgtttct ctgataatgt ccccaatcat accagggaga    780
ctggcattga cgagaactca ggtggaggct tgagaaggcc gaaagggccc ctgacctgcc    840
tggcttcctt agcttgcccc tcagctttgc aaagagccac cctaggcccc agctgaccgc    900
atgggtgtga gccagcttga aacactaac tactcaataa aagcgaaggt ggacaaaaaa     960
aaaaaaaaaa                                                            970

<210> SEQ ID NO 191
<211> LENGTH: 309
<212> TYPE: DNA
<213> ORGANISM: Homo sapiens

<400> SEQUENCE: 191
tatcatcagt aactgcagga catgattatt gaggcttgat tggcaaatac gacttctaca     60
tccatattct catctttcat accatatcac actactacca cttttgaag atcatcaaa     120
gagcaatgca aatgaaaaac actataattt actgtatact ctttgtttca ggatacttgc    180
cttttcaatt gtcacttgat gatataattg caatttaaac tgttaagctg tgttcagtac    240
tgtttctgaa aatagaaat cacttctcta aaagcaataa atttcaagca cattttaca     300
taaaaaaaa                                                            309

<210> SEQ ID NO 192
<211> LENGTH: 976
<212> TYPE: DNA
<213> ORGANISM: Homo sapiens

<400> SEQUENCE: 192
aatgtgaggc gattattta agtaattatc ttaccaagcc caagactggt tttaaagtta     60
cctgaagctc ttaacttcct cccctctgaa tttagtttgg ggaaggtgtt tttagtacaa    120
gacatcaaag tgaagtaaag cccaagtgtt ctttagcttt ttataatact gtctaaatag    180
tgaccatctc atgggcattg ttttcttctc tgctttgtct gtgttttgag tctgctttct    240
tttgtcttta aaacctgatt tttaagttct tctgaactgt agaaatagct atctgatcac    300
ttcagcgtaa agcagtgtgt ttattaacca tccactaagc taaaactaga gcagtttgat    360
ttaaaagtgt cactcttcct cctttttctac tttcagtaga tatgagatag agcataatta    420
tctgttttat cttagtttta tacataattt accatcagat agaactttat ggttctagta    480
cagatactct actacactca gcctcttatg tgccaagttt ttctttaagc aatgagaaat    540
tgctcatgtt cttcatcttc tcaaatcatc agaggccaaa gaaaaacact ttggctgtgt    600
ctataacttg acacagtcaa tagaatgaag aaaattagag tagttatgtg attatttcag    660
ctcttgacct gtcccctctg gctgcctctg agtctgaatc tcccaaagag agaaaccaat    720
ttctaagagg actggattgc agaagactcg gggacaacat ttgatccaag atcttaaatg    780
ttatattgat aaccatgctc agcaatgagc tattagattc attttgggaa atctccataa    840
tttcaatttg taaactttgt taagacctgt ctacattgtt atatgtgtgt gacttgagta    900
atgttatcaa cgttttttgta aatatttact atgtttttct attagctaaa ttccaacaat    960
```

| | |
|---|---|
| tttgtactتt aataaa | 976 |

<210> SEQ ID NO 193
<211> LENGTH: 81
<212> TYPE: DNA
<213> ORGANISM: Homo sapiens

<400> SEQUENCE: 193

| | |
|---|---|
| guuccacucu agcagcacgu aaauauuggc guagugaaau auauauuaaa caccaauauu | 60 |
| acugugcugc uuuaguguga c | 81 |

<210> SEQ ID NO 194
<211> LENGTH: 110
<212> TYPE: DNA
<213> ORGANISM: Homo sapiens

<400> SEQUENCE: 194

| | |
|---|---|
| agaagggcua ucaggccagc cuucagagga cuccaaggaa cauucaacgc ugucggugag | 60 |
| uuugggauuu gaaaaaacca cugaccguug acuguaccuu ggggucucua | 110 |

<210> SEQ ID NO 195
<211> LENGTH: 84
<212> TYPE: DNA
<213> ORGANISM: Homo sapiens

<400> SEQUENCE: 195

| | |
|---|---|
| ggcuguggcu ggauucaagu aauccaggau aggcuguuuc caucugugag gccuauucuu | 60 |
| gauuacuugu uucuggaggc agcu | 84 |

<210> SEQ ID NO 196
<211> LENGTH: 72
<212> TYPE: DNA
<213> ORGANISM: Homo sapiens

<400> SEQUENCE: 196

| | |
|---|---|
| agauacugua aacauccuac acucucagcu guggaaagua agaaagcugg gagaaggcug | 60 |
| uuuacucuuu cu | 72 |

<210> SEQ ID NO 197
<211> LENGTH: 111
<212> TYPE: DNA
<213> ORGANISM: Homo sapiens

<400> SEQUENCE: 197

| | |
|---|---|
| agaguguuca aggacagcaa gaaaaaugag ggacuuucag gggcagcugu guuucugac | 60 |
| ucagucauaa ugccccuaaa aauccuuauu guucuugcag ugugcaucgg g | 111 |

<210> SEQ ID NO 198
<211> LENGTH: 72
<212> TYPE: DNA
<213> ORGANISM: Homo sapiens

<400> SEQUENCE: 198

| | |
|---|---|
| agguugaggu aguagguugu auaguuuaga auuacaucaa gggagauaac uguacagccu | 60 |
| ccuagcuuuc cu | 72 |

<210> SEQ ID NO 199
<211> LENGTH: 74
<212> TYPE: DNA

<213> ORGANISM: Homo sapiens

<400> SEQUENCE: 199
gggugaggua guagguugua aguuugggg cucugcccug cuaugggaua acuauacaau    60
cuacugucuu uccu    74

<210> SEQ ID NO 200
<211> LENGTH: 83
<212> TYPE: DNA
<213> ORGANISM: Homo sapiens

<400> SEQUENCE: 200 uguggauga gguaguagau uguauaguuu uagggucaua ccccaucuug gagauaacua    60
uacagucuac ugucuuuccc acg    83

<210> SEQ ID NO 201
<211> LENGTH: 25
<212> TYPE: RNA
<213> ORGANISM: Homo sapiens

<400> SEQUENCE: 201
uaggcagugu auugcuagcg gcugu    25

<210> SEQ ID NO 202
<211> LENGTH: 23
<212> TYPE: RNA
<213> ORGANISM: homo sapiens

<400> SEQUENCE: 202
uugcuaguug cacuccucuc ugu    23

<210> SEQ ID NO 203
<211> LENGTH: 92
<212> TYPE: DNA
<213> ORGANISM: homo sapiens

<400> SEQUENCE: 203
gcugggaugu gucagguagg caguguauug cuagcggcug uuaaugauuu uaacaguugc    60
uaguugcacu ccucucuguu gcauucagaa gc    92

<210> SEQ ID NO 204
<211> LENGTH: 20
<212> TYPE: DNA
<213> ORGANISM: Homo sapiens

<400> SEQUENCE: 204
ccagctaaca atacactgcc    20

<210> SEQ ID NO 205
<211> LENGTH: 21
<212> TYPE: DNA
<213> ORGANISM: homo sapiens

<400> SEQUENCE: 205
agctatgcca gcatcttgcc t    21

<210> SEQ ID NO 206
<211> LENGTH: 22
<212> TYPE: DNA
<213> ORGANISM: homo sapiens

<400> SEQUENCE: 206

```
gtgtaacacg tctatacgcc ca                                               22

<210> SEQ ID NO 207
<211> LENGTH: 22
<212> TYPE: DNA
<213> ORGANISM: Homo sapiens

<400> SEQUENCE: 207
accagcuaac aauacacugc ca                                               22

<210> SEQ ID NO 208
<211> LENGTH: 20
<212> TYPE: DNA
<213> ORGANISM: Homo sapiens

<400> SEQUENCE: 208
causcgucga ucguagcgca                                                  20

<210> SEQ ID NO 209
<211> LENGTH: 22
<212> TYPE: DNA
<213> ORGANISM: xenopus laevis

<400> SEQUENCE: 209
accagctaac attacactgc ct                                               22

<210> SEQ ID NO 210
<211> LENGTH: 25
<212> TYPE: DNA
<213> ORGANISM: xenopus laevis

<400> SEQUENCE: 210
acagccagct agcaagtgca ctgcc                                            25

<210> SEQ ID NO 211
<211> LENGTH: 25
<212> TYPE: DNA
<213> ORGANISM: xenopus laevis

<400> SEQUENCE: 211
acagccagct agcaagtgca ctgcc                                            25

<210> SEQ ID NO 212
<211> LENGTH: 22
<212> TYPE: DNA
<213> ORGANISM: xenopus laevis

<400> SEQUENCE: 212
tgcacgtttc aatacagacc gt                                               22
```